United States Patent
Schnall-Levin et al.

(10) Patent No.: US 11,636,921 B2
(45) Date of Patent: Apr. 25, 2023

(54) SYSTEMS AND METHODS FOR INFERRING CELL STATUS

(71) Applicant: 10X Genomics, Inc., Pleasanton, CA (US)

(72) Inventors: Michael Schnall-Levin, San Francisco, CA (US); Rajiv Bharadwaj, Pleasanton, CA (US); Zahra Kamila Belhocine, Fremont, CA (US); Andrew D. Price, Hayward, CA (US); Yifeng Yin, Elk Grove, CA (US); Vijay Kumar Sreenivasa Gopalan, Santa Clara, CA (US); Zeljko Jovan Dzakula, San Diego, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 662 days.

(21) Appl. No.: 16/698,612

(22) Filed: Nov. 27, 2019

(65) Prior Publication Data
US 2020/0168297 A1    May 28, 2020

Related U.S. Application Data

(60) Provisional application No. 62/771,980, filed on Nov. 27, 2018.

(51) Int. Cl.
*G16B 30/00*    (2019.01)
*G16H 10/40*    (2018.01)
*G16H 20/00*    (2018.01)

(52) U.S. Cl.
CPC ............. *G16B 30/00* (2019.02); *G16H 10/40* (2018.01); *G16H 20/00* (2018.01)

(58) Field of Classification Search
CPC ......... G16B 30/00; G16H 10/40; G16H 20/00
See application file for complete search history.

(56) References Cited

U.S. PATENT DOCUMENTS

2015/0376609 A1    12/2015  Hindson et al.
2020/0005899 A1*    1/2020  Nicula ................... G16B 25/10
(Continued)

FOREIGN PATENT DOCUMENTS

WO    2017004153 A1    1/2017

OTHER PUBLICATIONS

International Search Report and Written Opinion for International application No. PCT/US2019/063719 dated Apr. 1, 2020, 17 pages.
(Continued)

*Primary Examiner* — Reginald R Reyes

(57) ABSTRACT

Systems and methods for inferring a status of a cell population are provided. Described techniques allow deconvolving a first clonal population comprising a first plurality of cells of a species, wherein nucleic acid sequence reads from each cell in the first plurality of cells are obtained. The nucleic acid sequence reads are mapped into bins representing portions of a reference genome, and a pattern of sequence read counts for each cell across the multiple bins is used to assign a cell to a group, thereby inferring a mitotic status of the cell. The assignment of nucleic acid sequence reads into bins is also be used for segregating cells into classes based on a status of a certain biological marker in each cell. Comparison of sequence read counts for a subset of bins across the cell classes allows evaluating effect of a compound on a cell status.

22 Claims, 24 Drawing Sheets

(56) References Cited

U.S. PATENT DOCUMENTS

2021/0398617 A1* 12/2021 Finkle .................... G16B 40/20
2022/0336046 A1* 10/2022 Zhu ........................ G16B 30/10

OTHER PUBLICATIONS

Krajcovic & Overholtzer, 2012, "Mechanisms of ploidy increase in human cancers: a new role for cell cannibalism," Cancer Research, 72(7), pp. 1596-1601.
Nickoloff et al., 2017, "Drugging the Cancers Addicted to DNA Repair," J. Natl. Cancer Inst. 109(11).
Shaheen et al., 2011, "Synthetic lethality: exploiting the addiction of cancer to DNA repair," Blood 117(23), pp. 6074-6082.
Kelley et al., 2014, "Targeting DNA repair pathways for cancer treatment: what's new?", Future Oncol. 10(7), pp. 1215-1237.
Zheng et al., 2016, "Halotyping germline and cancer genomes with high-throughput linked-read sequencing", Nat Biotchnol. 34(3): 303-311.
Chromium, Single Cell 3' Reagent Kits v2. User Guide, 2017, 10X Genomics, Pleasanton, California, Rev. B, p. 2.
Narasimhan et al., 2016, "Health and population effects of rare gene knockouts in adult humans with related parents," Science 352, pp. 474-477 (2016).
Mostovoy et al., 2016, "A hybrid approach for de novo human genome sequence assembly and phasing," Nat. Methods 13, 587-590.
Ji et al., "Phosphorylated fraction of H2AX as a measurement for DNA damage in cancer cells and potential applications of a novel assay", 2017, PLoS ONE 12(2): e0171582. doi:10.1371/journal.pone.0171582.

* cited by examiner

202 A computer system 100 having one or more processors 102 and memory 104 storing one or more programs for execution by the one or more processors. The one or more programs comprise instructions for performing the following method of deconvolving a first clonotype population comprising a first plurality of cells of a species.

204 Obtain a set of nucleic acid sequence reads 122 from each cell in the first plurality of cells of the first clonotype population through a single cell sequencing process, thereby obtaining a first plurality of sets of nucleic acid sequence reads. Each respective set of nucleic acid sequence reads in the first plurality of sets of nucleic acid sequence reads is from a single cell in the first plurality of cells.

206 The single cell sequence process is a single cell DNA sequence process and each nucleic acid sequence read in each set in the plurality of sets of nucleic acid sequence reads is a DNA sequence.

208 The single cell sequence process is a single cell RNA sequence process and each nucleic acid sequence read in each set in the plurality of sets of nucleic acid sequence reads is an RNA sequence.

210 Expose the first plurality of cells to a perturbation prior to the obtaining step.

212 The first plurality of cells are exposed to the perturbation for at least one hour prior to performing the obtaining step.

214 The perturbation is a compound.

216 The compound is an organic compound having a molecular weight of less than 2000 Daltons, the compound is an organic compound that satisfies the Lipinski rule of five criteria, or the compound is an organic compound that satisfies at least three criteria of the Lipinski rule of five criteria.

218 The compound is a checkpoint blockade immunotherapy.

220 The the checkpoint blockade immunotherapy is an anti-CTLA-4, anti-PD1, anti-PD-L1, anti-LAG3, anti-TIM-3, anti-GITR, anti-OX40, anti-CD40, anti-TIGIT, anti4-1BB, anti-B7-H3, anti-B7-H4, or anti-BTLA compound.

222 The first plurality of cells is heterogeneous.

224 The first plurality of cells is from a tumor biopsy.

Fig. 2A (A)

226 Map a nucleic acid sequence of each respective sequence read in each respective set of sequence reads onto a corresponding bin 124 in a plurality of bins. Each respective bin in the plurality of bins represents a different portion of a reference genome of the species, thereby obtaining a nucleic acid sequence read count for each respective bin in the plurality of bins for each respective cell in the first plurality of cells.

228 The species is human. Each bin in the plurality of bins is the same size and the plurality of bins collectively encompass at least three percent of the entire human genome, and
the plurality of bins consists of between one hundred and two thousand bins.

230 For each respective cell in the first plurality of cells, assign the respective cell into one of a plurality of groups 126 based upon a pattern of sequence read counts of the respective cell across the plurality of bins. A first group in the plurality of groups represents a first mitotic stage. A second group in the plurality of groups represents a non-mitotic stage. The assigning determines whether the respective cell is to be assigned to the first group by applying a first mitotic filter to the nucleic acid read count of respective bins in the plurality of bins obtained for the respective cell, thereby deconvolving the first clonotype population.

232 The mapping normalizes the nucleic acid sequence read count for each respective bin in the plurality of bins for each respective cell in the first plurality of cells. The first mitotic filter is a first predetermined pattern of read counts across a first subset of the plurality of bins that has been previously associated with the first mitotic stage. A respective cell in the first plurality of cells is assigned to the first group when the predetermined pattern of read counts across the first subset of the bins of the first mitotic filter is exhibited by the normalized nucleic acid sequence read counts for the respective cell across the first subset of the plurality of bins.

234 A third group in the plurality of groups represents a second mitotic stage. The assigning determines whether the respective cell is to be assigned to the third group by applying a second mitotic filter to the nucleic acid read count of respective bins in the plurality of bins obtained for the respective cell. The second mitotic filter is a second predetermined pattern of read counts across a second subset of the plurality of bins that has been previously associated with the second mitotic stage. The respective cell in the first plurality of cells is assigned to the second group when the predetermined pattern of read counts across the subset of the bins of the second mitotic filter is exhibited by the normalized nucleic acid sequence read counts for the respective cell across the second subset of the plurality of bins.

236 Obtain a set of nucleic acid sequence reads from each cell in a second clonotype population comprising a second plurality of cells of the species through a single cell sequencing process, thereby obtaining a second plurality of sets of nucleic acid sequence reads, wherein each respective set of nucleic acid sequence reads in the second plurality of sets of nucleic acid sequence reads is from a single cell in the second plurality of cells.

Map a nucleic acid sequence of each respective sequence read in each respective set of sequence reads in the second plurality of sets of nucleic acid sequence reads onto a corresponding bin in the plurality of bins.

For each respective cell in the second plurality of cells, assign the respective cell into one of the plurality of groups based upon a pattern of sequence read count of the respective cell across the plurality of bins, wherein the assigning determines whether the respective cell is to be assigned to the first group by applying the first mitotic filter to the nucleic acid read count of respective bins in the plurality of bins obtained for the respective cell.

Compare a relative assignment of cells in (i) the first plurality of cells and (ii) the second plurality of cells to individual groups in the first plurality of groups.

Fig. 2C

302 A computer system 100 having one or more processors 102 and memory 104 storing one or more programs for execution by the one or more processors. The one or more programs comprising instructions for performing the following method of deconvolving a heterogeneous population of cells comprising a first plurality of cells.

↓

304 Obtain a set of nucleic acid sequence reads from each cell in the first plurality of cells through a single cell sequencing process. In this way a first plurality of sets of nucleic acid sequence reads is obtained, where each respective set of nucleic acid sequence reads in the first plurality of sets of nucleic acid sequence reads is from a single cell in the first plurality of cells. The first plurality of cells is from an organism of a species that has been exposed to a DNA repair inhibitor.

↓

306 Map a nucleic acid sequence of each respective sequence read in each respective set of sequence reads onto a corresponding bin 124 in a plurality of bins. Each respective bin in the plurality of bins represents a different portion of a reference genome of the species. In this way a nucleic acid sequence read count is obtained for each respective bin in the plurality of bins for each respective cell in the first plurality of cells.

↓

308 Independently segregate each respective cell in the first plurality of cells into one of a plurality of cell classes 130 based on a presence, absence, or amount of a marker or a marker set in the respective cell.

↓

310 For each respective cell class in the plurality of classes, evaluate an average sequence read count for a predetermined subset of the plurality of bins across the cells of the respective cell class in the first plurality of cells.

↓

312 Compare the average sequence read count for the predetermined subset of the plurality of bins across the plurality of cell classes identified by the evaluating, thereby evaluating the DNA repair inhibitor.

Fig. 2D

402 A computer system 100 having one or more processors 102 and memory 104 storing one or more programs for execution by the one or more processors. The one or more programs comprising instructions for performing the following method of evaluating a DNA repair inhibitor.

404 Obtain a set of nucleic acid sequence reads from each cell in a first plurality of cells through a single cell sequencing process. The first plurality of cells is from an organism of a species that has been exposed to the DNA repair inhibitor. In this way, a first plurality of sets of nucleic acid sequence reads is obtained, where each respective set of nucleic acid sequence reads in the first plurality of sets of nucleic acid sequence reads is from a single cell in the first plurality of cells.

406 Map a nucleic acid sequence of each respective sequence read in each respective set of sequence reads onto a corresponding bin 124 in a plurality of bins. Each respective bin in the plurality of bins represents a different portion of a reference genome of the species. In this way, a nucleic acid sequence read count is obtained for each respective bin in the plurality of bins for each respective cell in the first plurality of cells.

408 Independently segregate each respective cell in the first plurality of cells into one of a plurality of cell classes 130 based on a presence, absence, or amount of a marker or a marker set in the respective cell.

410 For each respective cell in each respective cell class in the plurality of cell classes, assign the respective cell into one of a plurality of groups based upon a pattern of sequence read count of the respective cell across the plurality of bins. A first group in the plurality of groups represents a first mitotic stage, and a second group in the plurality of groups represents a non-mitotic stage. In this way it is determined whether the respective cell is to be assigned to the first group by applying a first mitotic filter to the nucleic acid read count of respective bins in the plurality of bins obtained for the respective cell.

412 Compare a proportion of cells in each cell class in the plurality of cell classes that are in the first mitotic stage.

502 Sequencing nucleic acids from a first plurality of cells in a first clonal population, by single cell sequencing, thereby generating a set of nucleic acid sequence reads from each cell in the first plurality of cells of the first clonal population

504 Deconvolving a mitotic profile for the first clonal population comprising the first plurality of cells from a first tumor biopsy from the subject by:

506 Obtaining a set of nucleic acid sequence reads from each cell in the first plurality of cells of the first clonal population through a single cell sequencing process, thereby obtaining a first plurality of sets of nucleic acid sequence reads, wherein each respective set of nucleic acid sequence reads in the first plurality of sets of nucleic acid sequence reads is from a single cell in the first plurality of cells

508 Mapping a nucleic acid sequence of each respective sequence read in each respective set of sequence reads onto a corresponding bin in a plurality of bins, wherein each respective bin in the plurality of bins represents a different portion of a reference genome of the species, thereby obtaining a nucleic acid sequence read count for each respective bin in the plurality of bins for each respective cell in the first plurality of cells

510 Assigning, for each respective cell in the first plurality of cells, the respective cell into one of a plurality of groups based upon a pattern of sequence read counts of the respective cell across the plurality of bins, wherein
     a first group in the plurality of groups represents a first mitotic stage,
     a second group in the plurality of groups represents a non-mitotic stage, and
     the assigning determines whether the respective cell is to be assigned to the first group by applying a first mitotic filter to the nucleic acid read count of respective bins in the plurality of bins obtained for the respective cell, thereby deconvolving the mitotic profile for the first clonal population

512 Determining whether the deconvolved mitotic profile for the first clonal population resembles a mitotic profile associated with a first cancer state or a mitotic state associated with a second cancer state 514 When the deconvolved mitotic profile for the first clonal population resembles a mitotic profile associated with a first cancer state, administering a therapy for treatment of the first cancer state to the subject 516 When the deconvolved mitotic profile for the first clonal population resembles a mitotic profile associated with a second cancer state, administering a second therapy for treatment of the second cancer state to the subject

Fig. 2F

```
                                    600
┌─────────────────────────────────────────────────────────────────────────────┐
│ 602 Sequencing nucleic acids from a first plurality of cells in a first     │
│ clonal population, by single cell sequencing, thereby generating a set of   │
│ nucleic acid sequence reads from each cell in the first plurality of cells  │
│ of the first clonal population                                              │
└─────────────────────────────────────────────────────────────────────────────┘
                                     ▼
┌─────────────────────────────────────────────────────────────────────────────┐
│ 604 Deconvolving a mitotic profile for the first clonal population          │
│ comprising the first plurality of cells from a first tumor biopsy from the  │
│ subject by:                                                                 │
│ ┌─────────────────────────────────────────────────────────────────────────┐ │
│ │ 606 Obtaining a set of nucleic acid sequence reads from each cell in    │ │
│ │ the first plurality of cells of the first clonal population through a   │ │
│ │ single cell sequencing process, thereby obtaining a first plurality of  │ │
│ │ sets of nucleic acid sequence reads, wherein each respective set of     │ │
│ │ nucleic acid sequence reads in the first plurality of sets of nucleic   │ │
│ │ acid sequence reads is from a single cell in the first plurality of     │ │
│ │ cells                                                                   │ │
│ └─────────────────────────────────────────────────────────────────────────┘ │
│                                     ▼                                       │
│ ┌─────────────────────────────────────────────────────────────────────────┐ │
│ │ 608 Mapping a nucleic acid sequence of each respective sequence read    │ │
│ │ in each respective set of sequence reads onto a corresponding bin in a  │ │
│ │ plurality of bins, wherein each respective bin in the plurality of      │ │
│ │ bins represents a different portion of a reference genome of the        │ │
│ │ species, thereby obtaining a nucleic acid sequence read count for each  │ │
│ │ respective bin in the plurality of bins for each respective cell in     │ │
│ │ the first plurality of cells                                            │ │
│ └─────────────────────────────────────────────────────────────────────────┘ │
│                                     ▼                                       │
│ ┌─────────────────────────────────────────────────────────────────────────┐ │
│ │ 610 Assigning, for each respective cell in the first plurality of       │ │
│ │ cells, the respective cell into one of a plurality of groups based      │ │
│ │ upon a pattern of sequence read counts of the respective cell across    │ │
│ │ the plurality of bins, wherein                                          │ │
│ │       a first group in the plurality of groups represents a first       │ │
│ │ mitotic stage,                                                          │ │
│ │       a second group in the plurality of groups represents a            │ │
│ │ non-mitotic stage, and                                                  │ │
│ │       the assigning determines whether the respective cell is to be     │ │
│ │ assigned to the first group by applying a first mitotic filter to the   │ │
│ │ nucleic acid read count of respective bins in the plurality of bins     │ │
│ │ obtained for the respective cell, thereby deconvolving the mitotic      │ │
│ │ profile for the first clonal population                                 │ │
│ └─────────────────────────────────────────────────────────────────────────┘ │
│                                     ▼                                       │
│ ┌─────────────────────────────────────────────────────────────────────────┐ │
│ │ 612 Determining whether the deconvolved mitotic profile for the first   │ │
│ │ clonal population resembles a mitotic profile for a population of       │ │
│ │ cancerous cells that are sensitive to a first type of therapy           │ │
│ └─────────────────────────────────────────────────────────────────────────┘ │
│ ┌─────────────────────────────────────────────────────────────────────────┐ │
│ │ 614 When the deconvolved mitotic profile for the first clonal           │ │
│ │ population resembles a mitotic profile for a population of cancerous    │ │
│ │ cells that are sensitive to a first type of therapy, administering the  │ │
│ │ first type of therapy to the subject                                    │ │
│ └─────────────────────────────────────────────────────────────────────────┘ │
│ ┌─────────────────────────────────────────────────────────────────────────┐ │
│ │ 616 When the deconvolved mitotic profile for the first clonal           │ │
│ │ population does not resemble a mitotic profile for a population of      │ │
│ │ cancerous cells that are sensitive to a first type of therapy,          │ │
│ │ administering a second type of therapy to the subject                   │ │
│ └─────────────────────────────────────────────────────────────────────────┘ │
└─────────────────────────────────────────────────────────────────────────────┘
```

702 Sequencing nucleic acids from a first plurality of cells in a first clonal population, by single cell sequencing, thereby generating a set of nucleic acid sequence reads from each cell in the first plurality of cells of the first clonal population

704 Deconvolving a mitotic profile for the first clonal population comprising the first plurality of cells from a first tumor biopsy from a subject being treated for cancer with a first type of therapy:

706 Obtaining a set of nucleic acid sequence reads from each cell in the first plurality of cells of the first clonal population through a single cell sequencing process, thereby obtaining a first plurality of sets of nucleic acid sequence reads, wherein each respective set of nucleic acid sequence reads in the first plurality of sets of nucleic acid sequence reads is from a single cell in the first plurality of cells

708 Mapping a nucleic acid sequence of each respective sequence read in each respective set of sequence reads onto a corresponding bin in a plurality of bins, wherein each respective bin in the plurality of bins represents a different portion of a reference genome of the species, thereby obtaining a nucleic acid sequence read count for each respective bin in the plurality of bins for each respective cell in the first plurality of cells

710 Assigning, for each respective cell in the first plurality of cells, the respective cell into one of a plurality of groups based upon a pattern of sequence read counts of the respective cell across the plurality of bins, wherein
    a first group in the plurality of groups represents a first mitotic stage,
    a second group in the plurality of groups represents a non-mitotic stage, and
    the assigning determines whether the respective cell is to be assigned to the first group by applying a first mitotic filter to the nucleic acid read count of respective bins in the plurality of bins obtained for the respective cell, thereby deconvolving the mitotic profile for the first clonal population

712 Comparing the deconvolved mitotic profile for the first clonal population to a deconvolved mitotic profile for a second clonal population comprising a second plurality of cells from a second tumor biopsy obtained from the subject prior to being treated for cancer with the first type of therapy

714 When a change in the deconvolved mitotic profile for the first clonal population, relative to the deconvolved mitotic profile for the second clonal population, indicates that the first type of therapy is not producing at least a threshold level of efficacy, administering a second type of therapy to the subject

716 When a change in the deconvolved mitotic profile for the first clonal population, relative to the deconvolved mitotic profile for the second clonal population, indicates that the first type of therapy is producing at least a threshold level of efficacy, continue administering the first type of therapy to the subject

Fig. 2H

SYSTEMS AND METHODS FOR INFERRING CELL STATUS

CROSS REFERENCE TO RELATED APPLICATIONS

This application claims priority to U.S. Provisional Patent Application No. 62/771,980 entitled "Systems and Methods for Inferring Cell Status," filed Nov. 27, 2018, which is hereby incorporated by reference.

TECHNICAL FIELD

This specification describes technologies relating to inferring cell status. In particular, a sequencing of cells in a biological sample is followed by identifying and characterizing each cell and thereby inferring a cell status of the sample.

BACKGROUND

Advances in genetic amplification technologies and nucleic acid sequencing technologies has led to various discoveries in medicine, biotechnology, and forensics. The techniques facilitate a number of technical applications such as the discovery of changes in cell characteristics, which may allow diagnosing a disease and selecting an appropriate treatment. For instance, in the biological arts, advances in RNA-extraction protocols and associated methodologies has led to the ability to perform whole transcriptome shotgun sequencing that quantifies gene expression in biological samples in counts of transcript reads mapped to genes. This has given rise to high throughput transcript generation and the quantification of gene expression for hundreds or even thousands of individual cells in a single dataset. Thus, large datasets of gene/transcript reads can be generated. To use this data in biotechnology and medical applications, for example, for diagnosing and treating cancer, technologies are required to determine and interpret variations within this data, and to relate the sequencing data to underlying biological processes.

SUMMARY

Technical solutions (e.g., systems and methods) for addressing the above identified problems by assigning meaning to variations in a heterogeneous cell population are provided in the present disclosure. The technical solutions include characterizing, or deconvolving, a heterogeneous cell population, where a cell status (e.g., a mitotic status) of the cell population and its cell sub-populations can be identified. The technical solutions also include inferring a mutational status of a heterogeneous cell population, which can be used to, for example, evaluate a compound or other form of perturbation to which the cell population or a portion thereof has been exposed.

The DNA replication status among cells in a clone can be used to indicate the cell cycle status of each of those cells. The collective distribution of these cell cycle statuses allows for the inference of characteristics of the cellular replication of these cell populations (for example, what fraction are replicating, how this is impacted by treatments, etc.).

The following presents a summary of the invention in order to provide a basic understanding of some of the aspects of the invention. This summary is not an extensive overview of the invention. It is not intended to identify key/critical elements of the invention or to delineate the scope of the invention. Its sole purpose is to present some of the concepts of the invention in a simplified form as a prelude to the more detailed description that is presented later.

An aspect of the disclosure provides a method of deconvolving a first clonal population comprising a first plurality of cells of a species. The method includes, at a computer system having one or more processors, and memory storing one or more programs for execution by the one or more processors, obtaining a set of nucleic acid sequence reads from each cell in the first plurality of cells of the first clonal population through a single cell sequencing process, thereby obtaining a first plurality of sets of nucleic acid sequence reads. Each respective set of nucleic acid sequence reads in the first plurality of sets of nucleic acid sequence reads is from a single cell in the first plurality of cells. The method further includes mapping a nucleic acid sequence of each respective sequence read in each respective set of sequence reads onto a corresponding bin in a plurality of bins, where each respective bin in the plurality of bins represents a different portion of a reference genome of the species, thereby obtaining a nucleic acid sequence read count for each respective bin in the plurality of bins for each respective cell in the first plurality of cells. For each respective cell in the first plurality of cells, the method further comprises assigning the respective cell into one of a plurality of groups based upon a pattern of sequence read counts of the respective cell across the plurality of bins. A first group in the plurality of groups represents a first mitotic stage, and a second group in the plurality of groups represents a non-mitotic stage. The assigning determines whether the respective cell is to be assigned to the first group by applying a first mitotic filter to the nucleic acid read count of respective bins in the plurality of bins obtained for the respective cell, thereby deconvolving the first clonal population.

The method can vary in different ways. For example, the single cell sequencing process can be a single cell DNA sequencing process and each nucleic acid sequence read in each set in the plurality of sets of nucleic acid sequence reads is a DNA sequence. As another example, the single cell sequencing process is a single cell RNA sequencing process and each nucleic acid sequence read in each set in the plurality of sets of nucleic acid sequence reads is an RNA sequence.

In some embodiments, the mapping normalizes the nucleic acid sequence read count for each respective bin in the plurality of bins for each respective cell in the first plurality of cells, the first mitotic filter is a first predetermined pattern of read counts across a first subset of the plurality of bins that has been previously associated with the first mitotic stage, and a respective cell in the first plurality of cells is assigned to the first group when the predetermined pattern of read counts across the first subset of the bins of the first mitotic filter is exhibited by the normalized nucleic acid sequence read counts for the respective cell across the first subset of the plurality of bins.

In some embodiments, a third group in the plurality of groups represents a second mitotic stage, and the assigning determines whether the respective cell is to be assigned to the third group by applying a second mitotic filter to the nucleic acid read count of respective bins in the plurality of bins obtained for the respective cell. In such embodiments the second mitotic filter is a second predetermined pattern of read counts across a second subset of the plurality of bins that has been previously associated with the second mitotic stage. A respective cell in the first plurality of cells is assigned to the second group when the predetermined pattern of read counts across the subset of the bins of the second mitotic filter is exhibited by the normalized nucleic acid sequence read counts for the respective cell across the second subset of the plurality of bins.

The species can be any suitable organism, and the bins of a certain size can be defined within the species' genome in any suitable way. For example, in some embodiments, the species is human, each bin in the plurality of bins is the same size, the plurality of bins collectively encompass at least three percent of the entire human genome, and the plurality of bins consists of between one hundred and two thousand bins. In other embodiments, bins can have different sizes. As another variation, the plurality of bins can consist of fewer than hundred or greater than two thousand bins.

In some embodiments, the first plurality of cells is exposed to a perturbation prior to the obtaining step. The first plurality of cells can be exposed to the perturbation for at least one hour prior to performing the obtaining, or other suitable amounts of time such as two to three hours, six or more hours, etc.

The perturbation can be a compound of any suitable type. For example, in some embodiments, the compound is an organic compound having a molecular weight of less than 2000 Daltons. In some embodiments, the compound is an organic compound that satisfies the Lipinski rule of five criteria. In some embodiments, the compound is an organic compound that satisfies at least three criteria of the Lipinski rule of five criteria. In some embodiments, the compound is a checkpoint blockade immunotherapy. The checkpoint blockade immunotherapy can be, for example, one or more of an anti-CTLA-4, anti-PD1, anti-PD-L1, anti-LAG3, anti-TIM-3, anti-GITR, anti-OX40, anti-CD40, anti-TIGIT, anti4-1BB, anti-B7-H3, anti-B7-H4, or anti-BTLA compound.

In some embodiments, the method of deconvolving the first clonal population comprising the first plurality of cells includes obtaining a set of nucleic acid sequence reads from each cell in a second clonal population comprising a second plurality of cells of the species through a single cell sequencing process, thereby obtaining a second plurality of sets of nucleic acid sequence reads, where each respective set of nucleic acid sequence reads in the second plurality of sets of nucleic acid sequence reads is from a single cell in the second plurality of cells. In such embodiments the method further comprises mapping a nucleic acid sequence of each respective sequence read in each respective set of sequence reads in the second plurality of sets of nucleic acid sequence reads onto a corresponding bin in the plurality of bins. For each respective cell in the second plurality of cells, the method in such embodiments further comprises assigning the respective cell into one of the plurality of groups based upon a pattern of sequence read counts of the respective cell across the plurality of bins, where the assigning determines whether the respective cell is to be assigned to the first group by applying the first mitotic filter to the nucleic acid read count of respective bins in the plurality of bins obtained for the respective cell. In such embodiments, the method further comprises comparing a relative assignment of cells in (i) the first plurality of cells and (ii) the second plurality of cells to individual groups in the first plurality of groups.

The first plurality of cells can be heterogeneous. The first plurality of cells can be acquired from any suitable source. For example, in certain embodiments, the first plurality of cells is from a tumor biopsy.

In some embodiments, a computer system is provided that has one or more processors and memory storing one or more programs for execution by the one or more processors, the one or more programs comprising instructions for performing the method of deconvolving the first clonal population comprising the first plurality of cells in accordance with certain embodiments of the present disclosure.

In some embodiments, a non-transitory computer readable storage medium is provided, where the non-transitory computer readable storage medium stores instructions, which, when executed by a computer system, cause the computer system to perform the method of deconvolving the first clonal population comprising the first plurality of cells in accordance with certain embodiments of the present disclosure.

An aspect of the present disclosure provides a method of evaluating a DNA repair inhibitor that includes, at a computer system having one or more processors, and memory storing one or more programs for execution by the one or more processors, obtaining a set of nucleic acid sequence reads from each cell in a first plurality of cells through a single cell sequencing process, where the first plurality of cells is from an organism of a species that has been exposed to the DNA repair inhibitor, thereby obtaining a first plurality of sets of nucleic acid sequence reads, where each respective set of nucleic acid sequence reads in the first plurality of sets of nucleic acid sequence reads is from a single cell in the first plurality of cells. The method further comprises mapping a nucleic acid sequence of each respective sequence read in each respective set of sequence reads onto a corresponding bin in a plurality of bins, where each respective bin in the plurality of bins represents a different portion of a reference genome of the species, thereby obtaining a nucleic acid sequence read count for each respective bin in the plurality of bins for each respective cell in the first plurality of cells. The method further comprises independently segregating each respective cell in the first plurality of cells into one of a plurality of cell classes based on a presence, absence, or amount of a marker or a marker set in the respective cell; for each respective cell class in the plurality of classes. The method further comprises evaluating an average sequence read count for a predetermined subset of the plurality of bins across the cells of the respective cell class in the first plurality of cells. The method further comprises comparing an average sequence read count for the predetermined subset of the plurality of bins across the plurality of cell classes identified by the evaluating, thereby evaluating the DNA repair inhibitor.

The method of evaluating a DNA repair inhibitor can have variations. For example, the single cell sequencing process can be a single cell DNA sequencing process and each nucleic acid sequence read in each set in the first plurality of sets of nucleic acid sequence reads is a DNA sequence. As another example, the single cell sequencing process can be a single cell RNA sequencing process and each nucleic acid sequence read in each set in the first plurality of sets of nucleic acid sequence reads is an RNA sequence.

In some embodiments, the marker or the marker set comprises a predetermined genetic mutation and the segregating determines whether the respective cell includes the predetermined genetic mutation, where, when the respective cell includes the predetermined genetic mutation the respective cell is deemed to belong to a first class in the plurality of cell classes and when the respective cell does not include the predetermined genetic mutation, the respective cell is deemed to belong in a class in the plurality of cell classes other than the first class.

In some embodiments, the predetermined genetic mutation is a single nucleotide polymorphism, an insertion, a deletion, or an inversion.

In some embodiments, the marker or the marker set is a plurality of predetermined genetic mutations and the segregating determines whether the respective cell includes each predetermined genetic mutation in the plurality of predetermined genetic mutations, where, when the respective cell includes each predetermined genetic mutation in the plurality of predetermined genetic mutations, the respective cell is deemed to belong to a first class in the plurality of cell classes and when the respective cell does not include each predetermined genetic mutation in the plurality of predetermined genetic mutations the respective cell is deemed to belong in a class in the plurality of cell classes other than the first class. Each predetermined genetic mutation in the plurality of predetermined genetic mutations can be a single nucleotide polymorphism, an insertion, a deletion, or an inversion.

In some embodiments, the marker is a threshold number of genetic mutations mapping to one or more predetermined portions of the reference genome and the segregating determines whether the respective cell includes the threshold number of genetic mutations, where, when the respective cell includes the threshold number of genetic mutations, the respective cell is deemed to belong to a first class in the plurality of cell classes and when the respective cell does not include the threshold number of genetic mutations, the respective cell is deemed to belong in a class in the plurality of cell classes other than the first class.

The threshold number of genetic mutations can be determined in various ways. For example, in some embodiments, the threshold number is determined by evaluating an average number and standard deviation of the average number of mutations in the one or more predetermined portions of the reference genome across a population of cells of the species that have not been exposed to the DNA repair inhibitor. In some embodiments, the threshold number is determined by evaluating an average number and standard deviation of the average number of mutations in the one or more predetermined portions of the reference genome across the first plurality of cells. In some embodiments, each genetic mutation mapping to the one or more predetermined portions of the reference genome is a single nucleotide polymorphism, an insertion, a deletion, or an inversion in the one or more predetermined portions of the reference genome. In some embodiments, the one or more predetermined portions of the reference genome consists of the X-Ray Repair Cross Complementing 2 (XRCC2) gene, the X-Ray Repair Cross Complementing 3 (XRCC3) gene, the RAD54 gene, the H2AX gene, the phosphatase and tensin homolog gene, and/or the ATM gene.

In some embodiments, the species is human, each bin in the plurality of bins is the same size and the plurality of bins collectively encompass at least three percent of the entire human genome, and the plurality of bins consists of between one hundred and two thousand bins.

In some embodiments, the organism is exposed to the DNA repair inhibitor for at least one hour prior to performing the obtaining step. The DNA repair inhibitor can be a compound. In some embodiments, the compound is an organic compound having a molecular weight of less than 2000 Daltons. In some embodiments, the compound is an organic compound that satisfies the Lipinski rule of five criteria or at least three criteria of the Lipinski rule of five criteria. In some embodiments, the compound is a poly ADP ribose polymerase (PARP) inhibitor.

In some embodiments, a method of deconvolving a first clonal population comprises a first plurality of cells in accordance with certain embodiments of the present disclosure further includes obtaining a set of nucleic acid sequence reads from each cell in a second plurality of cells of the species through a single cell sequencing process, thereby obtaining a second plurality of sets of nucleic acid sequence reads. Each respective set of nucleic acid sequence reads in the second plurality of sets of nucleic acid sequence reads is from a single cell in the second plurality of cells. The method further comprises mapping a nucleic acid sequence of each respective sequence read in each respective set of sequence reads in the second plurality of sets of nucleic acid sequence reads onto a corresponding bin in the plurality of bins. For each respective cell in the second plurality of cells, the method further comprises independently segregating the respective cell into one of the plurality of cell classes based on the presence, absence, or amount of the marker or the marker set in the respective cell. For each respective cell class in the plurality of classes, the method further comprises evaluating an average sequence read count for a predetermined subset of the plurality of bins across the cells of the respective cell class in the second plurality of cells. The method further comprises comparing, for each respective cell class in the plurality of cell classes, an average sequence read count for the respective cell class for the predetermined subset of the plurality of bins obtained from the first plurality of cells versus the second plurality of cells. The first plurality of cells can be heterogeneous. In some embodiments, the first plurality of cells is from a tumor biopsy.

An aspect of the present disclosure provides a method of deconvolving a heterogeneous population of cells comprising a first plurality of cells that includes, at a computer system having one or more processors, and memory storing one or more programs for execution by the one or more processors, obtaining a set of nucleic acid sequence reads from each cell in the first plurality of cells through a single cell sequencing process, thereby obtaining a first plurality of sets of nucleic acid sequence reads, where each respective set of nucleic acid sequence reads in the first plurality of sets of nucleic acid sequence reads is from a single cell in the first plurality of cells. The method further comprises mapping a nucleic acid sequence of each respective sequence read in each respective set of sequence reads onto a corresponding bin in a plurality of bins, where each respective bin in the plurality of bins represents a different portion of a reference genome of the species, thereby obtaining a nucleic acid sequence read count for each respective bin in the plurality of bins for each respective cell in the first plurality of cells. The method further comprises independently segregating each respective cell in the first plurality of cells into one of a plurality of cell classes based on a presence, absence, or amount of a marker or a marker set in the respective cell; for each respective cell in each respective cell class in the plurality of cell classes. The method further comprises assigning the respective cell into one of a plurality of groups based upon a pattern of sequence read counts of the respective cell across the plurality of bins, where a first group in the plurality of groups represents a first mitotic stage, a second group in the plurality of groups represents a non-mitotic stage. This assigning determines whether the respective cell is to be assigned to the first group by applying a first mitotic filter to the nucleic acid read count of respective bins in the plurality of bins obtained for the respective cell. The method further comprises comparing a proportion of cells in each cell class in the plurality of cell classes that are in the first mitotic stage.

The method of deconvolving the heterogeneous population of cells can vary in different ways. For example, in some embodiments, the single cell sequencing process is a single cell DNA sequencing process and each nucleic acid sequence read in each set in the first plurality of sets of nucleic acid sequence reads is a DNA sequence. In other embodiments, the single cell sequencing process is a single cell RNA sequencing process and each nucleic acid sequence read in each set in the first plurality of sets of nucleic acid sequence reads is an RNA sequence.

In some embodiments, the marker or the marker set comprises a predetermined genetic mutation and the segregating determines whether the respective cell includes the predetermined genetic mutation, where, when the respective cell includes the predetermined genetic mutation the respective cell is deemed to belong to a first class in the plurality of cell classes and when the respective cell does not include the predetermined genetic mutation, the respective cell is deemed to belong in a class in the plurality of cell classes other than the first class.

In some embodiments, the marker or marker set is a plurality of predetermined genetic mutations and the segregating determines whether the respective cell includes each predetermined genetic mutation in the plurality of predetermined genetic mutations, where, when the respective cell includes each predetermined genetic mutation in the plurality of predetermined genetic mutations, the respective cell is deemed to belong to a first class in the plurality of cell classes and when the respective cell does not include each predetermined genetic mutation in the plurality of predetermined genetic mutations the respective cell is deemed to belong in a class in the plurality of cell classes other than the first class.

In some embodiments, the predetermined genetic mutation, or each predetermined genetic mutation in the plurality of predetermined genetic mutations, is a single nucleotide polymorphism, an insertion, a deletion, or an inversion.

In some embodiments, the marker is a threshold number of genetic mutations mapping to one or more predetermined portions of the reference genome and the segregating determines whether the respective cell includes the threshold number of genetic mutations, where, when the respective cell includes the threshold number of genetic mutations, the respective cell is deemed to belong to a first class in the plurality of cell classes and when the respective cell does not include the threshold number of genetic mutations, the respective cell is deemed to belong in a class in the plurality of cell classes other than the first class. In some embodiments, the threshold number is determined by evaluating an average number and standard deviation of the average number of mutations in the one or more predetermined portions of the reference genome across the first plurality of cells. Each genetic mutation mapping to the one or more predetermined portions of the reference genome can be, for example, is a single nucleotide polymorphism, an insertion, a deletion, or an inversion in the one or more predetermined portions of the reference genome. In some embodiments, the one or more predetermined portions of the reference genome consists of the X-Ray Repair Cross Complementing 2 (XRCC2) gene, the X-Ray Repair Cross Complementing 3 (XRCC3) gene, the RAD54 gene, the H2AX gene, the phosphatase and tensin homolog gene, and/or the ATM gene.

In some embodiments, the species is human, each bin in the plurality of bins is the same size and the plurality of bins collectively encompass at least three percent of the entire human genome, and the plurality of bins consists of between one hundred and two thousand bins.

In some embodiments, the method of deconvolving the heterogeneous population of cells includes obtaining a set of nucleic acid sequence reads from each cell in a second plurality of cells of the species through a single cell sequencing process, thereby obtaining a second plurality of sets of nucleic acid sequence reads, where each respective set of nucleic acid sequence reads in the second plurality of sets of nucleic acid sequence reads is from a single cell in the second plurality of cells and the second plurality of cells has been exposed to a compound. In such embodiments the method further comprises mapping a nucleic acid sequence of each respective sequence read in each respective set of sequence reads in the second plurality of sets of nucleic acid sequence reads onto a corresponding bin in the plurality of bins. The method further comprises, for each respective cell in the second plurality of cells, independently segregating the respective cell into one of the plurality of cell classes based on the presence, absence, or amount of the marker or the marker set in the respective cell. For each respective cell in each respective cell class in the plurality of cell classes for the second plurality of cells, the method further comprises assigning the respective cell into one of the plurality of groups based upon a pattern of sequence read counts of the respective cell across the plurality of bins by applying the first mitotic filter to the nucleic acid read count of respective bins in the plurality of bins obtained for the respective cell; and comparing a proportion of cells in each cell class in the plurality of cell classes that are in the first mitotic stage between the first plurality of cells and the second plurality of cells.

In some embodiments, the second plurality of cells is exposed to the compound for at least one hour prior to performing the obtaining. The compound can be, for example, a DNA repair inhibitor. In some embodiments, the compound is an organic compound having a molecular weight of less than 2000 Daltons. In some embodiments, the compound is an organic compound that satisfies the Lipinski rule of five criteria or at least three criteria of the Lipinski rule of five criteria. In some embodiments, the compound is a poly ADP ribose polymerase (PARP) inhibitor. The first plurality of cells can be heterogeneous. In some embodiments, the first plurality of cells is from a tumor biopsy.

In one aspect, the disclosure provides a method for diagnosing a disease state, e.g., a cancer state, of a subject based on the mitotic profile of a clonal population of cells, as determined using single cell sequencing. In some embodiments, the method includes deconvolving a mitotic profile for a first clonal population comprising a first plurality of cells from a first biological sample, e.g., a tumor biopsy, from the subject. The deconvolving includes obtaining a set of nucleic acid sequence reads from each cell in the first plurality of cells of the first clonal population through a single cell sequencing process, thereby obtaining a first plurality of sets of nucleic acid sequence reads, wherein each respective set of nucleic acid sequence reads in the first plurality of sets of nucleic acid sequence reads is from a single cell in the first plurality of cells. The deconvolving then includes mapping a nucleic acid sequence of each respective sequence read in each respective set of sequence reads onto a corresponding bin in a plurality of bins, wherein each respective bin in the plurality of bins represents a different portion of a reference genome of the species, thereby obtaining a nucleic acid sequence read count for each respective bin in the plurality of bins for each respective cell in the first plurality of cells. The deconvolving then includes for each respective cell in the first plurality of cells, assigning the respective cell into one of a plurality of groups based upon a pattern of sequence read counts of the respective cell across the plurality of bins, wherein a first group in the plurality of groups represents a first mitotic stage, a second group in the plurality of groups represents a non-mitotic stage, and the assigning determines whether the respective cell is to be assigned to the first group by applying a first mitotic filter to the nucleic acid read count of respective bins in the plurality of bins obtained for the respective cell, thereby deconvolving the mitotic profile for the first clonal population. The method then includes determining whether the deconvolved mitotic profile for the first clonal population resembles a mitotic profile associated with a first cancer state or a mitotic state associated with a second cancer state.

In one aspect, the disclosure provides a method for treating a disease state, e.g., a cancer state, of a subject based on the mitotic profile of a clonal population of cells, as determined using single cell sequencing. In some embodiments, the method includes deconvolving a mitotic profile for a first clonal population comprising a first plurality of cells from a first biological sample, e.g., a tumor biopsy, from the subject. The deconvolving includes obtaining a set of nucleic acid sequence reads from each cell in the first plurality of cells of the first clonal population through a single cell sequencing process, thereby obtaining a first plurality of sets of nucleic acid sequence reads, wherein each respective set of nucleic acid sequence reads in the first plurality of sets of nucleic acid sequence reads is from a single cell in the first plurality of cells. The deconvolving then includes mapping a nucleic acid sequence of each respective sequence read in each respective set of sequence reads onto a corresponding bin in a plurality of bins, wherein each respective bin in the plurality of bins represents a different portion of a reference genome of the species, thereby obtaining a nucleic acid sequence read count for each respective bin in the plurality of bins for each respective cell in the first plurality of cells. The deconvolving then includes for each respective cell in the first plurality of cells, assigning the respective cell into one of a plurality of groups based upon a pattern of sequence read counts of the respective cell across the plurality of bins, wherein a first group in the plurality of groups represents a first mitotic stage, a second group in the plurality of groups represents a non-mitotic stage, and the assigning determines whether the respective cell is to be assigned to the first group by applying a first mitotic filter to the nucleic acid read count of respective bins in the plurality of bins obtained for the respective cell, thereby deconvolving the mitotic profile for the first clonal population. The method then includes determining whether the deconvolved mitotic profile for the first clonal population resembles a mitotic profile associated with a first cancer state or a mitotic state associated with a second cancer state. When the deconvolved mitotic profile for the first clonal population resembles a mitotic profile associated with a first cancer state, the method optionally includes assigning and/or administering a therapy for treatment of the first cancer state to the subject. When the deconvolved mitotic profile for the first clonal population resembles a mitotic profile associated with a second cancer state, the method optionally includes assigning and/or administering a second therapy for treatment of the second cancer state to the subject.

In one aspect, the disclosure provides a method for providing a prognosis for a disease state, e.g., a cancer state, of a subject based on the mitotic profile of a clonal population of cells, as determined using single cell sequencing. In some embodiments, the method includes deconvolving a mitotic profile for a first clonal population comprising a first plurality of cells from a first biological sample, e.g., a tumor biopsy, from the subject. The deconvolving includes obtaining a set of nucleic acid sequence reads from each cell in the first plurality of cells of the first clonal population through a single cell sequencing process, thereby obtaining a first plurality of sets of nucleic acid sequence reads, wherein each respective set of nucleic acid sequence reads in the first plurality of sets of nucleic acid sequence reads is from a single cell in the first plurality of cells. The deconvolving then includes mapping a nucleic acid sequence of each respective sequence read in each respective set of sequence reads onto a corresponding bin in a plurality of bins, wherein each respective bin in the plurality of bins represents a different portion of a reference genome of the species, thereby obtaining a nucleic acid sequence read count for each respective bin in the plurality of bins for each respective cell in the first plurality of cells. The deconvolving then includes for each respective cell in the first plurality of cells, assigning the respective cell into one of a plurality of groups based upon a pattern of sequence read counts of the respective cell across the plurality of bins, wherein a first group in the plurality of groups represents a first mitotic stage, a second group in the plurality of groups represents a non-mitotic stage, and the assigning determines whether the respective cell is to be assigned to the first group by applying a first mitotic filter to the nucleic acid read count of respective bins in the plurality of bins obtained for the respective cell, thereby deconvolving the mitotic profile for the first clonal population. The method then includes determining whether the deconvolved mitotic profile for the first clonal population resembles a mitotic profile for a population of cancerous cells that are sensitive to a first type of therapy.

In one aspect, the disclosure provides a method for treating a disease state, e.g., a cancer state, of a subject based on the mitotic profile of a clonal population of cells, as determined using single cell sequencing. In some embodiments, the method includes deconvolving a mitotic profile for a first clonal population comprising a first plurality of cells from a first biological sample, e.g., a tumor biopsy, from the subject. The deconvolving includes obtaining a set of nucleic acid sequence reads from each cell in the first plurality of cells of the first clonal population through a single cell sequencing process, thereby obtaining a first plurality of sets of nucleic acid sequence reads, wherein each respective set of nucleic acid sequence reads in the first plurality of sets of nucleic acid sequence reads is from a single cell in the first plurality of cells. The deconvolving then includes mapping a nucleic acid sequence of each respective sequence read in each respective set of sequence reads onto a corresponding bin in a plurality of bins, wherein each respective bin in the plurality of bins represents a different portion of a reference genome of the species, thereby obtaining a nucleic acid sequence read count for each respective bin in the plurality of bins for each respective cell in the first plurality of cells. The deconvolving then includes for each respective cell in the first plurality of cells, assigning the respective cell into one of a plurality of groups based upon a pattern of sequence read counts of the respective cell across the plurality of bins, wherein a first group in the plurality of groups represents a first mitotic stage, a second group in the plurality of groups represents a non-mitotic stage, and the assigning determines whether the respective cell is to be assigned to the first group by applying a first mitotic filter to the nucleic acid read count of respective bins in the plurality of bins obtained for the respective cell, thereby deconvolving the mitotic profile for the first clonal population. The method then includes determining whether the deconvolved mitotic profile for the first clonal population resembles a mitotic profile for a population of cancerous cells that are sensitive to a first type of therapy. When the deconvolved mitotic profile for the first clonal population resembles a mitotic profile for a population of cancerous cells that are sensitive to a first type of therapy, the method optionally includes assigning and/or administering the first type of therapy to the subject. When the deconvolved mitotic profile for the first clonal population does not resemble a mitotic profile for a population of cancerous cells that are sensitive to a first type of therapy, the method optionally includes assigning and/or administering a second type of therapy to the subject.

In one aspect, the disclosure provides a method for monitoring efficacy of a therapy for a disease state, e.g., a cancer state, of a subject based on the mitotic profile of a clonal population of cells, as determined using single cell sequencing. In some embodiments, the method includes deconvolving a mitotic profile for a first clonal population comprising a first plurality of cells from a first biological sample, e.g., a tumor biopsy, from a subject being treated for a disease state, e.g., cancer, with a first type of therapy. The deconvolving includes obtaining a set of nucleic acid sequence reads from each cell in the first plurality of cells of the first clonal population through a single cell sequencing process, thereby obtaining a first plurality of sets of nucleic acid sequence reads, wherein each respective set of nucleic acid sequence reads in the first plurality of sets of nucleic acid sequence reads is from a single cell in the first plurality of cells. The deconvolving then includes mapping a nucleic acid sequence of each respective sequence read in each respective set of sequence reads onto a corresponding bin in a plurality of bins, wherein each respective bin in the plurality of bins represents a different portion of a reference genome of the species, thereby obtaining a nucleic acid sequence read count for each respective bin in the plurality of bins for each respective cell in the first plurality of cells. The deconvolving then includes for each respective cell in the first plurality of cells, assigning the respective cell into one of a plurality of groups based upon a pattern of sequence read counts of the respective cell across the plurality of bins, wherein a first group in the plurality of groups represents a first mitotic stage, a second group in the plurality of groups represents a non-mitotic stage, and the assigning determines whether the respective cell is to be assigned to the first group by applying a first mitotic filter to the nucleic acid read count of respective bins in the plurality of bins obtained for the respective cell, thereby deconvolving the mitotic profile for the first clonal population. The method then includes comparing the deconvolved mitotic profile for the first clonal population to a deconvolved mitotic profile for a second clonal population comprising a second plurality of cells from a second tumor biopsy obtained from the subject prior to being treated for cancer with the first type of therapy.

In one aspect, the disclosure provides a method for treating a disease state, e.g., a cancer state, of a subject based on the mitotic profile of a clonal population of cells, as determined using single cell sequencing. In some embodiments, the method includes deconvolving a mitotic profile for a first clonal population comprising a first plurality of cells from a first biological sample, e.g., a tumor biopsy, from a subject being treated for a disease state, e.g., cancer, with a first type of therapy. The deconvolving includes obtaining a set of nucleic acid sequence reads from each cell in the first plurality of cells of the first clonal population through a single cell sequencing process, thereby obtaining a first plurality of sets of nucleic acid sequence reads, wherein each respective set of nucleic acid sequence reads in the first plurality of sets of nucleic acid sequence reads is from a single cell in the first plurality of cells. The deconvolving then includes mapping a nucleic acid sequence of each respective sequence read in each respective set of sequence reads onto a corresponding bin in a plurality of bins, wherein each respective bin in the plurality of bins represents a different portion of a reference genome of the species, thereby obtaining a nucleic acid sequence read count for each respective bin in the plurality of bins for each respective cell in the first plurality of cells. The deconvolving then includes for each respective cell in the first plurality of cells, assigning the respective cell into one of a plurality of groups based upon a pattern of sequence read counts of the respective cell across the plurality of bins, wherein a first group in the plurality of groups represents a first mitotic stage, a second group in the plurality of groups represents a non-mitotic stage, and the assigning determines whether the respective cell is to be assigned to the first group by applying a first mitotic filter to the nucleic acid read count of respective bins in the plurality of bins obtained for the respective cell, thereby deconvolving the mitotic profile for the first clonal population. The method then includes comparing the deconvolved mitotic profile for the first clonal population to a deconvolved mitotic profile for a second clonal population comprising a second plurality of cells from a second tumor biopsy obtained from the subject prior to being treated for cancer with the first type of therapy. When a change in the deconvolved mitotic profile for the first clonal population, relative to the deconvolved mitotic profile for the second clonal population, indicates that the first type of therapy is not producing at least a threshold level of efficacy, the method optionally includes assigning and/or administering a second type of therapy to the subject. When a change in the deconvolved mitotic profile for the first clonal population, relative to the deconvolved mitotic profile for the second clonal population, indicates that the first type of therapy is producing at least a threshold level of efficacy, the method optionally includes assigning and/or administering continued administration of the first type of therapy to the subject.

In one aspect, the disclosure provides a method for providing a prognosis for a disease state, e.g., a cancer state, of a subject based on the mitotic profile of a clonal population of cells, as determined using single cell sequencing. In some embodiments, the method includes deconvolving a mitotic profile for a first clonal population comprising a first plurality of cells from a first biological sample, e.g., a tumor biopsy, from the subject that have been treated with a candidate therapeutic agent. The deconvolving includes obtaining a set of nucleic acid sequence reads from each cell in the first plurality of cells of the first clonal population through a single cell sequencing process, thereby obtaining a first plurality of sets of nucleic acid sequence reads, wherein each respective set of nucleic acid sequence reads in the first plurality of sets of nucleic acid sequence reads is from a single cell in the first plurality of cells. The deconvolving then includes mapping a nucleic acid sequence of each respective sequence read in each respective set of sequence reads onto a corresponding bin in a plurality of bins, wherein each respective bin in the plurality of bins represents a different portion of a reference genome of the species, thereby obtaining a nucleic acid sequence read count for each respective bin in the plurality of bins for each respective cell in the first plurality of cells. The deconvolving then includes for each respective cell in the first plurality of cells, assigning the respective cell into one of a plurality of groups based upon a pattern of sequence read counts of the respective cell across the plurality of bins, wherein a first group in the plurality of groups represents a first mitotic stage, a second group in the plurality of groups represents a non-mitotic stage, and the assigning determines whether the respective cell is to be assigned to the first group by applying a first mitotic filter to the nucleic acid read count of respective bins in the plurality of bins obtained for the respective cell, thereby deconvolving the mitotic profile for the first clonal population. The method then includes determining whether the deconvolved mitotic profile for the first clonal population resembles a mitotic profile for a population of cancerous cells that are sensitive to the candidate therapeutic agent.

In one aspect, the disclosure provides a method for providing a prognosis for a disease state, e.g., a cancer state, of a subject based on the mitotic profile of a clonal population of cells, as determined using single cell sequencing. In some embodiments, the method includes deconvolving a mitotic profile for a first clonal population comprising a first plurality of cells from a first biological sample, e.g., a tumor biopsy, from the subject that have been treated with a candidate therapeutic agent. The deconvolving includes obtaining a set of nucleic acid sequence reads from each cell in the first plurality of cells of the first clonal population through a single cell sequencing process, thereby obtaining a first plurality of sets of nucleic acid sequence reads, wherein each respective set of nucleic acid sequence reads in the first plurality of sets of nucleic acid sequence reads is from a single cell in the first plurality of cells. The deconvolving then includes mapping a nucleic acid sequence of each respective sequence read in each respective set of sequence reads onto a corresponding bin in a plurality of bins, wherein each respective bin in the plurality of bins represents a different portion of a reference genome of the species, thereby obtaining a nucleic acid sequence read count for each respective bin in the plurality of bins for each respective cell in the first plurality of cells. The deconvolving then includes for each respective cell in the first plurality of cells, assigning the respective cell into one of a plurality of groups based upon a pattern of sequence read counts of the respective cell across the plurality of bins, wherein a first group in the plurality of groups represents a first mitotic stage, a second group in the plurality of groups represents a non-mitotic stage, and the assigning determines whether the respective cell is to be assigned to the first group by applying a first mitotic filter to the nucleic acid read count of respective bins in the plurality of bins obtained for the respective cell, thereby deconvolving the mitotic profile for the first clonal population. The method then includes determining whether the deconvolved mitotic profile for the first clonal population resembles a mitotic profile for a population of cancerous cells that are sensitive to the candidate therapeutic agent. When the deconvolved mitotic profile for the first clonal population resembles a mitotic profile for a population of cancerous cells that are sensitive to the candidate therapeutic agent, the method optionally includes assigning and/or administering the candidate therapeutic agent to the subject. When the deconvolved mitotic profile for the first clonal population does not resemble a mitotic profile for a population of cancerous cells that are sensitive to the candidate therapeutic agent, the method optionally includes assigning and/or administering a second type of therapy, other than the candidate therapeutic agent, to the subject.

Various embodiments of systems, methods and devices within the scope of the appended claims each have several aspects, no single one of which is solely responsible for the desirable attributes described herein. Without limiting the scope of the appended claims, some prominent features are described herein. After considering this discussion, and particularly after reading the section entitled "Detailed Description" one will understand how the features of various embodiments are used.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The implementations disclosed herein are illustrated by way of example, and not by way of limitation, in the figures of the accompanying drawings. Like reference numerals refer to corresponding parts throughout the several views of the drawings.

FIGS. 2A, 2B, 2C, 2D, 2E, 2F, 2G, and 2H collectively illustrate example methods in accordance with various embodiments of the present disclosure, in which optional steps are indicated by broken lines.

DETAILED DESCRIPTION

Figure 1:
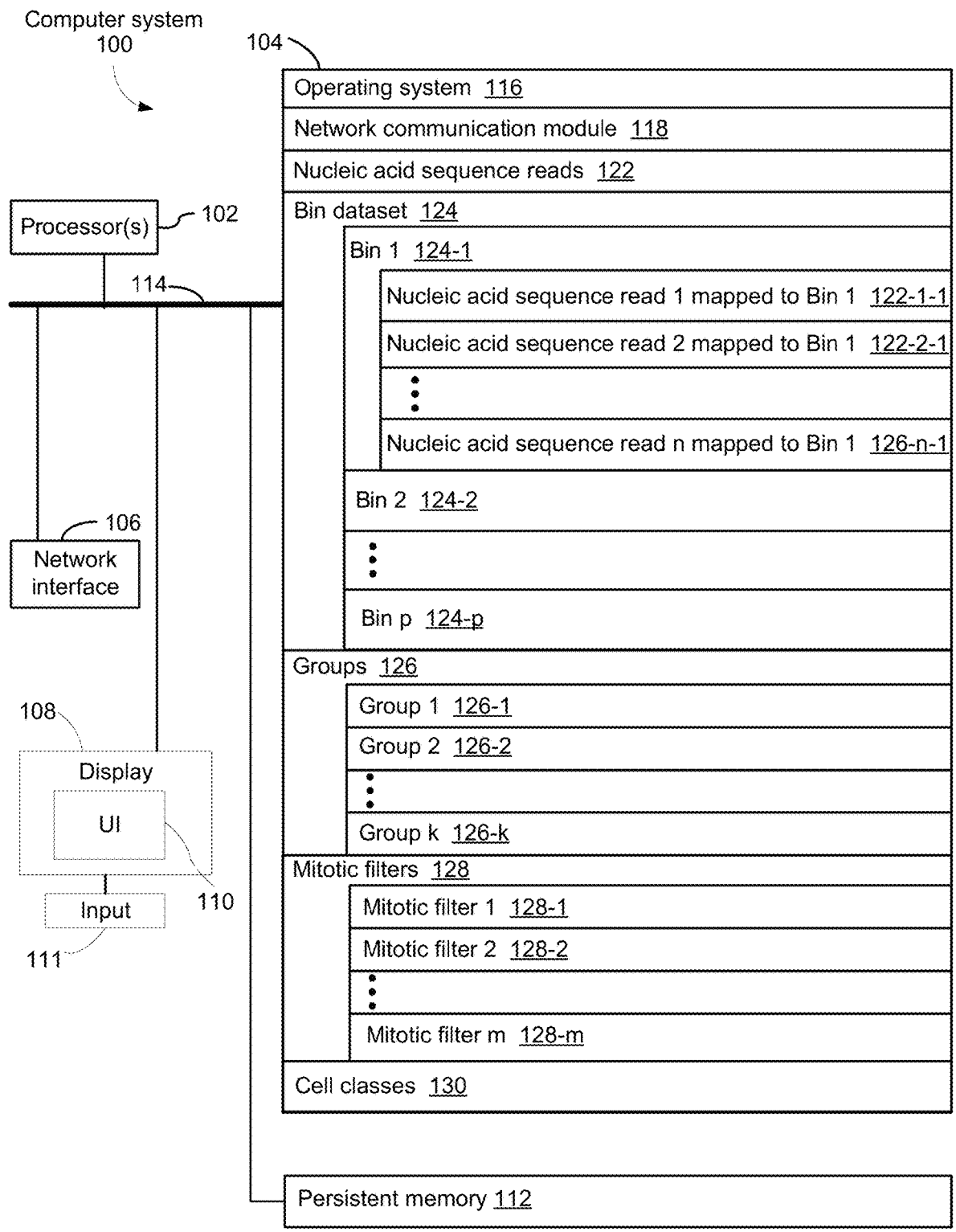
FIG. 1 is an example block diagram illustrating a computing device in accordance with some implementations.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

The implementations described herein provide various technical solutions to detect a pattern in datasets acquired based on processing and analysis of biological, medical, forensic and other samples. The sample can be processed using a single cell sequencing technology. An example of such datasets are datasets arising from whole transcriptome shotgun sequencing pipelines that quantify gene expression in single cells in counts of transcript reads mapped to genes. More particularly, as discussed in detail below, the present disclosure addresses the problem of determining a mitotic status or stage of a cell in a sample, and applying the result of the determination to characterize the sample and make decisions regarding a source or state of the sample.

Determining a mitotic status of cells in a sample is typically complicated because different cells may behave differently during mitosis and because various cells in the sample may be at different mitotic stages. This is exacerbated by the difficulty of interpreting variations in the cells behavior. Accordingly, the present disclosure improves the technology of medical diagnostics and monitoring by providing techniques for inferring status of cells in a sample (e.g., a heterogeneous population of cells from a single subject) and for presenting the inferred information on a user interface of a computing device in the form of various visualizations. The inferred information is presented on the user interface in a manner that allows evaluation of the sample cell status and that allows for making adjustments and modifications to the visualization. In this way, the determination of cell status of the sample sheds light on the mitotic status of the sample and the sample's response to various factors that could not be obtained using conventional sample analysis approaches.

The inference of a cell status of the sample can be used in determining what actions are to be taken with respect to the sample and/or its source (e.g., a patient from which the sample was obtained). For example, tumor cells undergo mitosis in the manner (e.g., random, uncontrolled proliferation) that is different from non-diseased cells, and the described techniques allow determining whether the sample includes cancerous or pre-cancerous cells. A treatment progress of the patient can be monitored using the techniques in accordance with the present disclosure. Moreover, because the single cell sequencing technology is used in the described approach, even if a small subset of the cell population in a sample is cancerous, such subsets can be inferred, and early measures can be taken to prevent further tumor development.

In some embodiments, the cell or the sample from which the cell is obtained can be subjected to a perturbation such that the effect of that perturbation on the cell or the sample can be evaluated. The perturbation can be a compound (e.g., an anti-cancer agent candidate) or another type of interference with the natural state of the cell and/or sample. The anti-cancer agent can be an agent that specifically targets cancer cell mitosis, or it can be any other type of agent. An effect of the perturbation on a mitotic stage of cells in the sample can then be determined. For example, a compound or another perturbation can be evaluated for its ability to affect the cell mitotic state. In this way, the techniques in accordance with the present disclosure improve drug discovery technology.

Details of implementations are now described in conjunction with the Figures.

FIG. 1 is a block diagram illustrating a computer system 100 in accordance with some implementations. The computer system 100 in some implementations includes one or more processing units CPU(s) 102 (also referred to as processors), a non-persistent memory 104 (also referred to herein as "memory"), one or more network interfaces 106, a display 108, a persistent memory 112, and one or more communication buses 114 for interconnecting these components. The one or more communication buses 114 optionally include circuitry (sometimes called a chipset) that interconnects and controls communications between system components.

The non-persistent memory 104 typically includes high-speed random access memory, such as DRAM, SRAM, DDR RAM, ROM, EEPROM, flash memory, etc., whereas the persistent memory 112 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The persistent memory 112 optionally includes one or more storage devices remotely located from the CPU(s) 102. The persistent memory 112, and the non-volatile memory device(s) within the non-persistent memory 104, comprise non-transitory computer readable storage medium. In some implementations, the memory 104, or non-transitory computer readable storage hardware, stores various programs, modules and data structures, or a subset thereof, sometimes in conjunction with the persistent memory 112.

In the described embodiments, as shown in FIG. 1, the memory 104 stores an operating system 116, a network communication module 118, a nucleic acid sequence reads dataset 122 comprising nucleic acid sequence reads, a bin dataset 124 comprising a plurality of bins, a groups module 126 comprising a plurality of groups, a mitotic filters module 128 comprising mitotic filters, and a cell classes module 130 comprising cell classes. It should be appreciated that the memory 104 can store other module(s) encompassing various other information, as the described embodiments are not limited to the implementation shown in FIG. 1.

The operating system 116 includes procedures for handling various system services and for performing hardware dependent tasks. The network communication module 118 is configured to connect the computer system 100 with other devices, or a communication network. The display 108, which can be any type of a display including a touch screen, is configured to present a user interface 110 that can display representation of data in accordance with the described embodiments. As shown schematically in FIG. 1, the display 108 can be associated with an input device 111 configured to receive user input. The input device 111 can be one or more of a keyboard, a computer mouse, a joystick, or another control device. It should be appreciated that in embodiments in which the computer system 100 is a smartphone, tablet, laptop or another mobile device, the input device 111 may be part of the display 108 such as, e.g., a touch screen device.

In some embodiments, one or more clonal populations can be deconvolved, using nucleic acid sequences obtained from cells from the clonal population(s) using a single cell sequencing process, as discussed in more detail below. Accordingly, as shown in FIG. 1, the nucleic acid sequence reads dataset 122 comprises a set of n nucleic acid sequence reads 122 from each cell in the first plurality of cells of a first clonal population of nucleic acid sequence reads. In some embodiments, the nucleic acid sequence reads comprise a first plurality of sets of nucleic acid sequence reads, with each respective set of nucleic acid sequence reads in the first plurality of sets of nucleic acid sequence read is from a single cell in the first plurality of cells. The nucleic acid sequences can be RNA or DNA sequences and they can be stored in the memory 104 in a suitable format.

The bin dataset 124 also stored in the memory 104 comprises a plurality of bins (p bins, in this example), where each bin in the plurality of bins has one or more nucleic acid sequence reads mapped onto that bin. The bins can be defined as portions along a reference genome or a portion of the reference genome. A suitable number of bins can be defined along at least a portion of the reference genomes. A nucleic acid sequence read is considered mapped onto a bin when it is determined that the nucleic acid sequence read matches the portion of the reference genome corresponding to that bin. In the example illustrated in FIG. 1, a first bin 124-1 comprises a first nucleic acid sequence read 122-1-1, a second nucleic acid sequence read 122-2-1, and an $n^{th}$-nucleic acid sequence read 122-n-1 mapped onto the first bin 124-1. It should be noted that "n" represents any number of nucleic acid sequence reads, including zero. The bin dataset 124 further comprises a second bin 124-2, and one or more subsequent bins up to the $p^{th}$ bin 124-p. Each of the plurality of bins in the bin dataset 124 can have one or more nucleic acid sequence reads mapped thereto, and the number of nucleic acid sequence reads mapped onto a particular bin is referred to herein as a sequence read count.

The groups module 126 comprises a plurality of groups including a first group 126-1, a second group 126-2, and subsequent groups up to the $k^{th}$ group 126-k. Each group can have a respective cell assigned thereto based upon a pattern of sequence read counts of that respective cell across the plurality of bins, as discussed in more detail below. The mitotic filters module 128 comprises a plurality of mitotic filters including a first mitotic filter 128-1, a second mitotic filter 128-2, and subsequent mitotic filter up to the $m^{th}$ mitotic filter 128-m. Any number of mitotic filters can be defined. In some embodiments in accordance with the present disclosure, the memory 104 also stores a cell classes module 130 comprising cell classes and discussed in more detail below.

In some implementations, one or more of the above identified elements and modules are stored in one or more of the previously mentioned memory devices, and correspond to a set of instructions for performing operations in accordance with implementations of the present disclosure. The above identified modules, data, or programs (e.g., sets of instructions) need not be implemented as separate software programs, procedures, datasets, or modules, and thus various subsets of these modules and data may be combined or otherwise rearranged in various implementations. In some implementations, the memory 104 optionally stores a subset of the modules and data structures identified above. Furthermore, in some embodiments, the memory stores additional modules and data structures not described above. In some embodiments, one or more of the above identified elements are stored in a computer system other than the system 100, that can communicate with the computer system 100 so that computer system 100 may access all or a portion of data stored in connection with these elements when needed.

It should be appreciated that FIG. 1 illustrates the computer system 100 by way of example, as the computer system 100 is intended more as functional description of the various features which may be present in computer systems than as a structural schematic of the implementations described herein. In practice, and as recognized by those of ordinary skill in the art, items shown separately could be combined and some items could be separated. Moreover, although FIG. 1 depicts certain data and modules in the non-persistent memory 104, some or all of these data and modules may be in the persistent memory 112. For example, while the mitotic filters module 130 is depicted as resident in the non-persistent memory 104, the mitotic filters module 130 can be entirely or in part resident in the persistent memory 112.

While an example of an implementation of a system in accordance the present disclosure has been disclosed with reference to FIG. 1, a method in accordance with the present disclosure is now detailed with reference to FIGS. 2A through 16C.

Block 202. One aspect of the present disclosure provides a computer system, a non-limiting example of which is illustrated in FIG. 1 as a computer system 100. The computer system 100 comprises one or more processing cores or processors 102 and the memory 104, which, together with the persistent memory 112, stores instructions for performing the method in accordance with the described techniques. FIGS. 2A to 2E collectively illustrate an example method in accordance with an embodiment of the present disclosure.

Block 204—Obtain a set of nucleic acid sequence reads 122 from each cell to obtain a first plurality of sets of nucleic acid sequence reads. Referring to block 204 of FIG. 2A, a method in accordance with the systems and methods of the present disclosure comprises obtaining a set of nucleic acid sequence reads 122 from each cell in the first plurality of cells of the first clonal population through a single cell sequencing process, thereby obtaining a first plurality of sets of nucleic acid sequence reads. Each respective set of nucleic acid sequence reads in the first plurality of sets of nucleic acid sequence reads is from a single cell in the first plurality of cells. The single cell sequencing process can be implemented in accordance with any suitable single cell sequencing technique. In some embodiments, the single cell sequencing process can be performed, for example, as described in U.S. Patent Application Publication No. 2015/0376609, entitled "Methods of Analyzing Nucleic Acids from Individual Cells or Cell Populations" and filed Jun. 26, 2015, the entire content of which is incorporated herein by reference.

The single cell sequencing process can vary in a number of ways, and a suitable portion of the cell's genome can be sequenced. For example, sequence reads can be acquired such that they represent at least twenty percent of the genome of the cell, or at least fifteen percent of the genome of the cell, or at least ten percent of the genome of the cell, or at least five percent of the genome of the cell, or at least four percent of the genome of the cell, or at least three percent of the genome of the cell, or at least two percent of the genome of the cell, or at least one percent of the genome of the cell. Also, in some embodiments, less than one percent of the genome of the cell is represented by the sequence reads.

In some embodiments, as shown at block 206 of FIG. 2A, the single cell sequencing process can be a single cell DNA sequence process, such that each nucleic acid sequence read in each set in the plurality of sets of nucleic acid sequence reads is a DNA sequence.

In some embodiments, as shown at block 208 of FIG. 2A, the single cell sequencing process can be a single cell RNA sequence process, such that each nucleic acid sequence read in each set in the plurality of sets of nucleic acid sequence reads is an RNA sequence.

As discussed above, the genome composition of a cell can be analyzed in accordance with the described embodiments using any suitable single cell sequencing process. The cell can be extracted using a variety of approaches.

In some embodiments, the cell or the sample from which the cell is obtained is not treated with any compound or otherwise subjected to a perturbation prior to analysis of the cell using a single cell sequencing technique. In other embodiments, however, the cell is exposed to a perturbation prior to the obtaining step in accordance with the present disclosure. An effect of the perturbation on a mitotic stage of the cell can then be determined. The perturbation can be any type of perturbation, and the cell can be exposed to the perturbation (block 210 of FIG. 2A) in various ways, and for a suitable time prior to the step of obtaining the set of nucleic acid reads from that cell. For example, in some embodiments, as shown at block 212 of FIG. 2A, the first plurality of cells are exposed to the perturbation for at least one hour prior to performing the obtaining step. It should be appreciated, however, that the first plurality of cells can be exposed to the perturbation for any other suitable period of time, which can be a time period of less than one hour.

In some embodiments, the perturbation may be a compound (block 214), which can be a compound of any suitable type (e.g., one or more drugs) that may affect a DNA or RNA replication status of the cell. Non-limiting examples of a compound comprise, as shown at block 216 in FIG. 2A, an organic compound having a molecular weight of less than 2000 Daltons. In some embodiments, the test perturbation is any organic compound having a molecular weight of less than 4000 Daltons, of less than 6000 Daltons, of less than 8000 Daltons, of less than 10000 Daltons, or less than 20000 Daltons.

In some embodiments, the perturbation is an organic compound that satisfies all four criteria of the Lipinski rule of five criteria: (i) not more than five hydrogen bond donors (e.g., OH and NH groups), (ii) not more than ten hydrogen bond acceptors (e.g., N and O), (iii) a molecular weight under 500 Daltons, and (iv) a Log P under 5. The "Rule of Five" is so called because three of the four criteria involve the number five. See, Lipinski, 1997, "Experimental and computational approaches to estimate solubility and permeability in drug discovery and development settings," Adv. Drug Del. Rev. 23, 3-26, which is hereby incorporated herein by reference in its entirety. In some embodiments, the perturbation is an organic compound that satisfies at least three criteria of the Lipinski rule of five criteria. In some embodiments, the perturbation can be an organic compound that satisfies at least two criteria of the Lipinski rule of five criteria.

In some embodiments, the compound is a checkpoint blockade immunotherapy, as shown at block 218 of FIG. 2A. Checkpoint blockade immunotherapies enable the host immune system to recognize and destroy tumor cells. Referring to block 220 of FIG. 2A, non-limiting examples of the checkpoint blockade immunotherapy include an anti-CTLA-4, anti-PD1, anti-PD-L1, anti-LAG3, anti-TIM-3, anti-GITR, anti-OX40, anti-CD40, anti-TIGIT, anti4-1BB, anti-B7-H3, anti-B7-H4, or anti-BTLA compound. In such embodiments, a checkpoint blockade immunotherapy can be administered to the first plurality of cells. For example, a subject determined to be in need of immunotherapy (e.g., a human subject diagnosed with cancer) can be administered a checkpoint blockade immunotherapy, and a biological sample comprising the first plurality of cells can be obtained from the subject. The response of the human subject to the checkpoint blockade immunotherapy can be used to develop a treatment (or a treatment regimen) for that subject. In some embodiments, the cancer is a carcinoma, a melanoma, a lymphoma/leukemia, a sarcoma, or a neuro-glial tumor. In some embodiments, the cancer is lung cancer, pancreatic cancer, colon cancer, stomach or esophagus cancer, breast cancer, ovary cancer, prostate cancer, or liver cancer.

In the described embodiments, the cells can be any type of cells, and they can be obtained from any suitable source. The cells analyzed using the systems and methods of the present disclosure can be from a sample encompassing a homogeneous cell population or from a heterogeneous cell population. Thus, in some embodiments, as shown at block 222 of FIG. 2A, the first plurality of cells is heterogeneous. For example, a cancerous cell population is heterogeneous such that it includes different cell subpopulations.

In some embodiments, as shown at block 224, the first plurality of cells are from a tumor biopsy. Thus, a response of a cell obtained from a tumor biopsy to an immunotherapy (e.g., a checkpoint blockade immunotherapy or another type of a therapy) can be determined using the systems and methods in accordance with the present disclosure. The tumor biopsy can include cells forming any type of solid or blood-borne tumor. Solid tumors may be benign (noncancerous), or malignant (cancerous). Non-limiting examples of solid tumors from which the tumor biopsy can be obtained include, but are not limited to, bladder cancer, breast cancer, colorectal cancer, kidney cancer, lymphoma (Non-Hodgkin), melanoma, oral and oropharyngeal cancer, pancreatic cancer, prostate cancer, thyroid cancer, uterine cancer, non-small-cell lung carcinoma (NSCLC), and carcinoma of unknown primary.

Block 226—Map a nucleic acid sequence of each respective sequence read onto a corresponding bin 124 in a plurality of bins. Referring to block 226 of FIG. 2B, the systems and methods of the present disclosure include mapping a nucleic acid sequence of each respective sequence read in each respective set of sequence reads onto a corresponding bin in a plurality of bins. Each respective bin in the plurality of bins represents a different portion of a reference genome of the species. In this way a nucleic acid sequence read count is obtained for each respective bin in the plurality of bins for each respective cell in the first plurality of cells.

Figure 6:
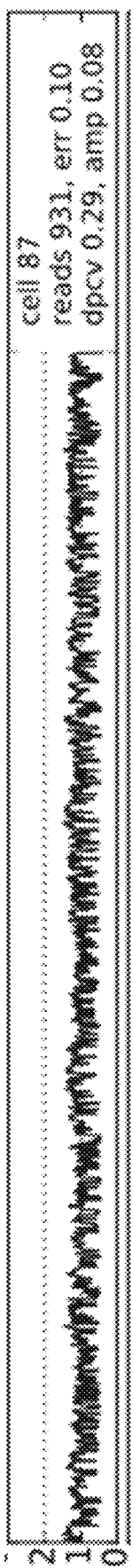
FIG. 6 illustrates mapping a nucleic acid sequence of each respective sequence read in a set of sequence reads corresponding to a replicating cell onto a corresponding bin in a plurality of bins, where each respective bin in the plurality of bins represents a different portion of a reference genome of the species, thereby obtaining a nucleic acid sequence read count for each respective bin in the plurality of bins for the replicating cell in accordance with an embodiment of the present disclosure.

FIG. 6 illustrates an example of a visualization of sequence reads (931 reads, in this example) obtained from a cell (cell 87, in this example) mapped into a plurality of bins. In particular, FIG. 6 illustrates mapping a nucleic acid sequence of each respective sequence read in a set of sequence reads corresponding to a replicating cell onto a corresponding bin in a plurality of bins, where each respective bin in the plurality of bins represents a different portion of a reference genome of the species.

Any suitable number of bins can be selected, each representing a certain portion of a reference genome. For example, in some embodiments, the method of deconvolving the first clonal population in accordance with the present disclosure includes deconvolving the first clonal population comprising a first plurality of cells of the species that is human (block 228). In such embodiments, each bin in the plurality of bins is the same size and the plurality of bins collectively encompass at least three percent of the entire human genome, and the plurality of bins consists of between one hundred and two thousand bins. However, it should be appreciated that the bins in the plurality of bins can be of a different size. For example, in some embodiments, at least one of the bins can have a different that is different from a size of at least one other bin in the plurality of bins. Furthermore, additionally or alternatively, the plurality of bins can encompass any suitable number of bins, including less than one hundred bins and greater than two thousand bins. The size of the bin can be selected prior to the mapping step (block 226) in accordance with the present disclosure. In some implementations, however, a size of the bin (or more than one size, since bins may have different sizes, as mentioned above), can be dynamically selected using operation of the computer system performing the method described herein.

Each bin can have a certain number of nucleic acid sequence reads (zero or more) acquired from a cell mapped thereto, such that collectively the distribution of the nucleic acid sequence reads among the bins demonstrates a pattern of sequence read counts of the cell. A different pattern of sequence read counts may correspond to a respective different degree of replication of the cell. For example, the cell can be a non-replicating cell, a replicating cell, or a cell undergoing what is referred to herein as a non-replication event, such as, e.g., abnormally frequent, tumorous replication.

Figure 8:
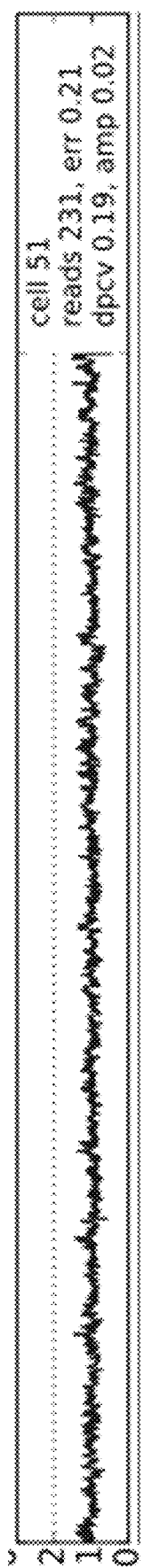
FIG. 8 illustrates mapping a nucleic acid sequence of each respective sequence read in a set of sequence reads corresponding to a non-replicating cell onto a corresponding bin in a plurality of bins, where each respective bin in the plurality of bins represents a different portion of a reference genome of the species, thereby obtaining a nucleic acid sequence read count for each respective bin in the plurality of bins for the non-replicating cell in accordance with an embodiment of the present disclosure.
Figure 10:
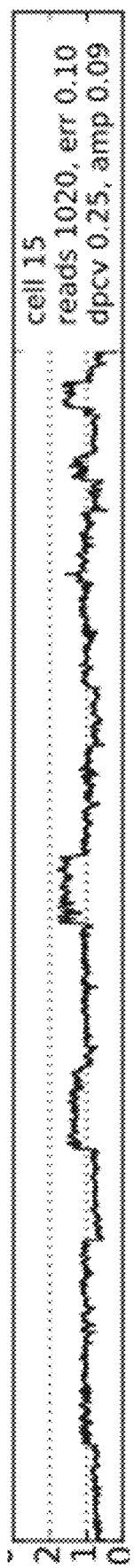
FIG. 10 illustrates mapping a nucleic acid sequence of each respective sequence read in a set of sequence reads corresponding to a cell undergoing a non-replication event onto a corresponding bin in a plurality of bins, where each respective bin in the plurality of bins represents a different portion of a reference genome of the species, thereby obtaining a nucleic acid sequence read count for each respective bin in the plurality of bins for the cell undergoing a non-replication event in accordance with an embodiment of the present disclosure.

Referring again to FIG. 6, an embodiment is shown illustrating a nucleic acid sequence read count that is obtained for each respective bin in the plurality of bins for the replicating cell. FIG. 8 illustrates mapping a nucleic acid sequence of each respective sequence read in a set of sequence reads corresponding to a non-replicating cell (cell 51) onto a corresponding bin in a plurality of bins. FIG. 10 illustrates mapping a nucleic acid sequence of each respective sequence read in a set of sequence reads corresponding to a cell (cell 15) undergoing a non-replication event onto a corresponding bin in a plurality of bins. The comparison of the jigsaw-like patterns of sequence read counts shown in FIGS. 6 and 8, respectively, reveals that amplitudes of the peaks of the respective pattern of FIG. 6 are higher than amplitudes of the peaks of the respective pattern of FIG. 8. The pattern of the sequence read counts shown in FIG. 10, on the other hand, illustrates variations in that pattern along a chromosome region, and the pattern of FIG. 10 is different from the respective patterns shown in FIGS. 6 and 8. The examples illustrated in FIGS. 6, 8, and 10 are further discussed below.

Block 230—Assign each cell in the first plurality of cells into one of a plurality of groups 126 based upon a pattern of sequence read counts of the respective cell across the plurality of bins. A pattern of sequence read counts determined for a cell across the plurality of bins can be used to assign that cell into one of a plurality of groups, as shown at block 230 of FIG. 2B. The plurality of groups can include any suitable number of groups representing a replication, non-replication, or otherwise characterized status of a cell. For example, in some embodiments, the plurality of groups encompass at least a first group in the plurality of groups that represents a first mitotic stage and a second group in the plurality of groups that represents a non-mitotic stage. In such embodiments, the assigning determines whether the respective cell is to be assigned to the first group by applying a first mitotic filter to the nucleic acid read count of respective bins in the plurality of bins obtained for the respective cell. In the techniques in accordance with the present disclosure, assigning the respective cell to the group (e.g., the first group) allows deconvolving the first clonal population. A mitotic status of the cell can thus be determined by assigning that cell to a group in a plurality of groups.

Figure 3:
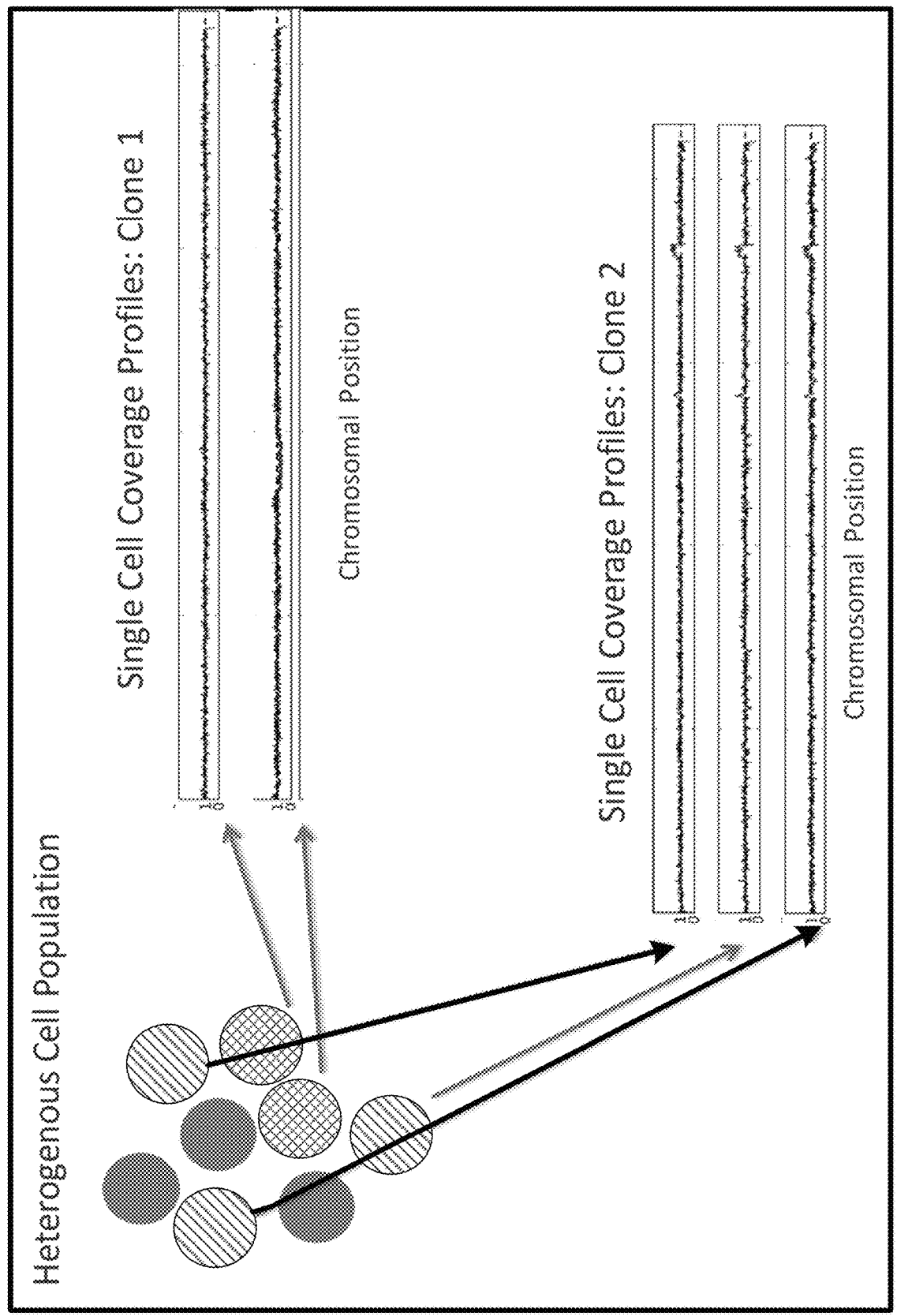
FIG. 3 illustrates, for each respective cell in a plurality of cells, assigning the respective cell into one of a plurality of groups based upon a pattern of sequence read counts of the respective cell across a plurality of bins in accordance with an embodiment of the present disclosure.

FIG. 3 illustrates an example where each respective cell in a plurality of cells is assigned into one of a plurality of groups based upon a pattern of sequence read counts of the respective cell across a plurality of bins in accordance with an embodiment of the present disclosure. In particular, FIG. 3 illustrates schematically a heterogeneous cell population, where cells belonging to respective different clonal populations are marked differently. The heterogeneous cell population (e.g., a cancer cell population) can be deconvolved in accordance with embodiments of the present disclosure by assigning each cell to a group in a plurality of groups. In this way, FIG. 3 illustrates that a pattern of sequence read counts (referred to as a single cell coverage profile) for each cell from the heterogeneous cell population is used to assign some cells (marked with a crosshatch pattern) from that heterogeneous population to a first group (Clone 1) and to assign some cells (marked with a diagonal parallel lines pattern) from that heterogeneous population to a second group (Clone 2). As shown in FIG. 3, the cells assigned to the first group (Clone 1) have a pattern of sequence read counts (in bins along a chromosome) that is generally different than a pattern of sequence read counts of the cell assigned to the second group (Clone 2). It should be noted that, within the group or the clonal population, the cells may not have identical respective patterns of sequence read counts, but collectively these patterns will differ from pattern(s) of sequence read counts of cells assigned to another group.

As discussed above, in the described embodiments, for a respective cell, each bin in a plurality of bins has a sequence read count assigned thereto, which indicates a number of sequence reads detected at a region of a reference genome represented by that bin. For example, FIGS. 6, 8, and 10 illustrate, for a respective cell, respective results of mapping of nucleic acid sequence reads onto a plurality of bins. A pattern of sequence read counts of the cell across the plurality of bins is used to determine a group to which the cell is assigned. In some embodiments, to determine which group a certain pattern of sequence read counts represents, a mitotic filter is applied to the nucleic acid read counts assigned to respective bins.

A mitotic filter can be defined in various ways in accordance with the systems and methods of the present disclosure. In some embodiments, as shown at block 232, the mapping of nucleic acid sequences in a set of sequence reads onto a corresponding bin 124 in a plurality of bins (discussed in connection with block 226 in FIG. 2B), normalizes the nucleic acid sequence read count for each respective bin in the plurality of bins for each respective cell in the first plurality of cells. In such embodiments, the first mitotic filter is a first predetermined pattern of read counts across a first subset of the plurality of bins that has been previously associated with the first mitotic stage. In other words, the mitotic filter can be a predetermined pattern that is known to represent a mitotic stage. In some embodiments, the mitotic filter can be a dynamically updatable filter such that the corresponding pattern can be adjusted. Regardless of the specific way in which the first mitotic filter is defined, a respective cell in the first plurality of cells is assigned to the first group when the predetermined pattern of read counts across the first subset of the bins of the first mitotic filter is exhibited by the normalized nucleic acid sequence read counts for the respective cell across the first subset of the plurality of bins.

In some embodiments, as shown at block 234 in FIG. 2B, a third group in the plurality of groups represents a second mitotic stage. Further, in these embodiments, the assigning at block 230 determines whether the respective cell is to be assigned to the third group by applying a second mitotic filter to the nucleic acid read count of respective bins in the plurality of bins obtained for the respective cell. The second mitotic filter can be defined in various ways. For example, in some embodiments, the second mitotic filter is a second predetermined pattern of read counts across a second subset of the plurality of bins that has been previously associated with the second mitotic stage. Thus, a respective cell in the first plurality of cells can be assigned to the second group when the predetermined pattern of read counts across the subset of the bins of the second mitotic filter is exhibited by the normalized nucleic acid sequence read counts for the respective cell across the second subset of the plurality of bins.

Figure 4:
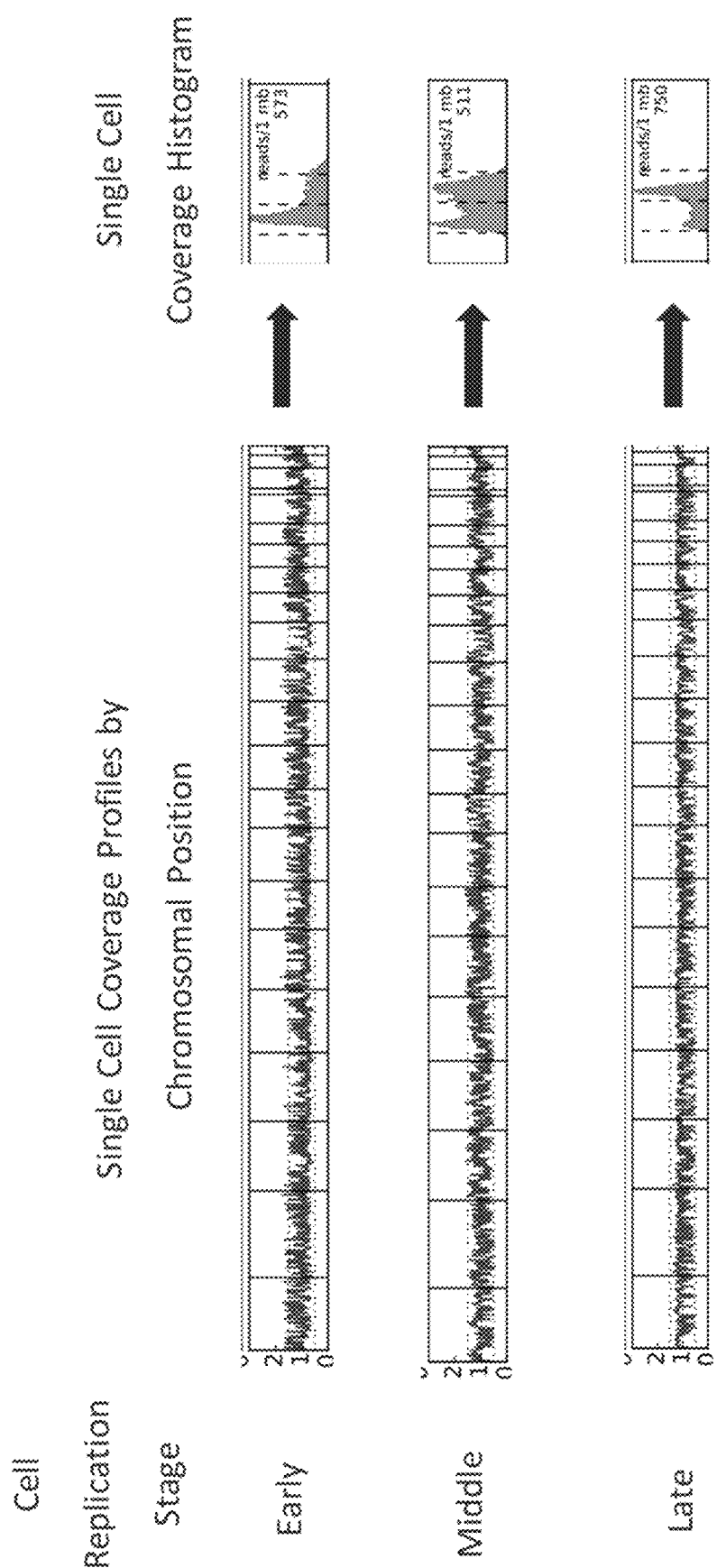
FIG. 4 illustrates for each respective cell in the first plurality of cells, assigning the respective cell into one of a plurality of groups based upon a pattern of sequence read counts of the respective cell across the plurality of bins, where a first group in the plurality of groups represents a first mitotic stage, a second group in the plurality of groups a second mitotic stage, and a third group in the plurality of groups represents a third mitotic stage; where the assigning determines whether the respective cell is to be assigned to the first, second or third group by applying a mitotic filter to the nucleic acid read count of respective bins in a plurality of bins obtained for the respective cell in accordance with an embodiment of the present disclosure.

FIG. 4 illustrates, for each respective cell in the first plurality of cells, assigning the respective cell into one of a plurality of groups based upon a pattern of sequence read counts of the respective cell across the plurality of bins. As shown in FIG. 4, a first group in the plurality of groups represents a first mitotic stage ("early"), a second group in the plurality of groups a second mitotic stage ("middle"), and a third group in the plurality of groups represents a third mitotic stage ("late"). In the example of FIG. 4, the assigning determines whether the respective cell is to be assigned to the first, second or third group by applying a mitotic filter to the nucleic acid read count of respective bins in a plurality of bins obtained for the respective cell in accordance with an embodiment of the present disclosure.

As discussed above, FIGS. 6, 8 and 10 illustrate respective different distributions of a number of sequence reads in a replicating cell (cell 87), a non-replicating cell (cell 51), and a cell undergoing a non-replicating event (cell 15). The DNA replication status of individual cells in a clonal population can be determined based on a fraction of the genome that is at different ploidies. For example, in a typical diploid sample that is undergoing replication, the fraction of the genome can have an average ploidy of 2, 3, or 4.

In some embodiments, a visual representation of a distribution of a number of sequence reads of a cell versus a number of bins representing at least a portion of a reference genome provides a histogram illustrating a coverage distribution for that cell. The distribution of the number of sequence reads can be analyzed using a statistical technique (e.g., a Gaussian mixture model approach or another technique) to determine whether the distribution follows a replication profile, a non-replicating profile, or whether the distribution does not follow either of these profiles. Accordingly, the results of the analysis reveal a number of ploidy bin populations among the plurality of bins. For example, in FIG. 7, which illustrates the distribution of the number of sequence reads in the replicating cell (cell 87) of FIG. 6 across the plurality of bins, the number of sequence reads is displayed on the x-axis, and the total number of bins that has the respective number of sequence reads mapped thereto are displayed on the y-axis. In this example, a small number of bins have about 400 sequence reads mapped thereto, whereas most bins have about 1200 sequence reads mapped thereto.

Figure 7:
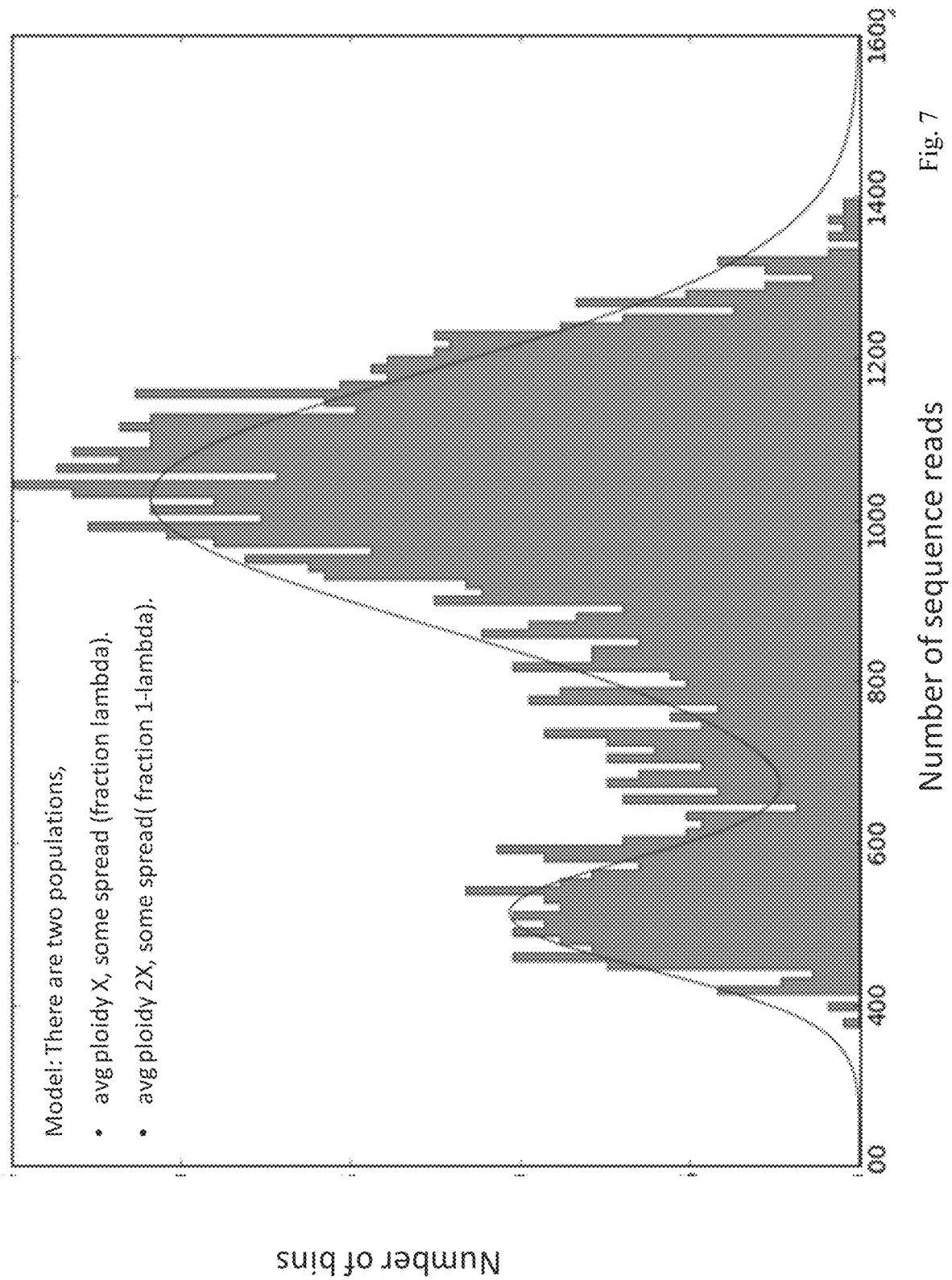
FIG. 7 illustrates how the distribution of the number of sequence reads in the replicating cell (cell 87) of FIG. 6 across the plurality of bins indicates that there are two ploidy bin populations among the plurality of bins, one that has an average ploidy of X, and another than has an average ploidy of 2X, in accordance with an embodiment of the present disclosure.

As further shown in FIG. 7, an appropriate statistical model, such as, e.g., a Gaussian mixture model, can be fitted to the frequency of occurrence of each sequence read across the plurality of bins, and a result can reveal a number of ploidy bin populations among the plurality of bins. In this way, a curve in FIG. 7, shown along with the histogram, demonstrates that there are two peaks each corresponding to a respective sub-population or population present in the replicating cell 87. In particular, FIG. 7 shows that the replicating cell (cell 87) has two ploidy bin populations among the plurality of bins—one (left, as shown in FIG. 7) that has an average ploidy of X, and another (right, as shown in FIG. 7) that has an average ploidy of 2X. The peak on the right corresponds to a number of sequence reads from a portion of the cell's genome that is near replication points, while the peak on the left corresponds to a portion of the genome that is farther away from the replication points. FIG. 7 thus illustrates that the cell is undergoing replication.

Figure 9:
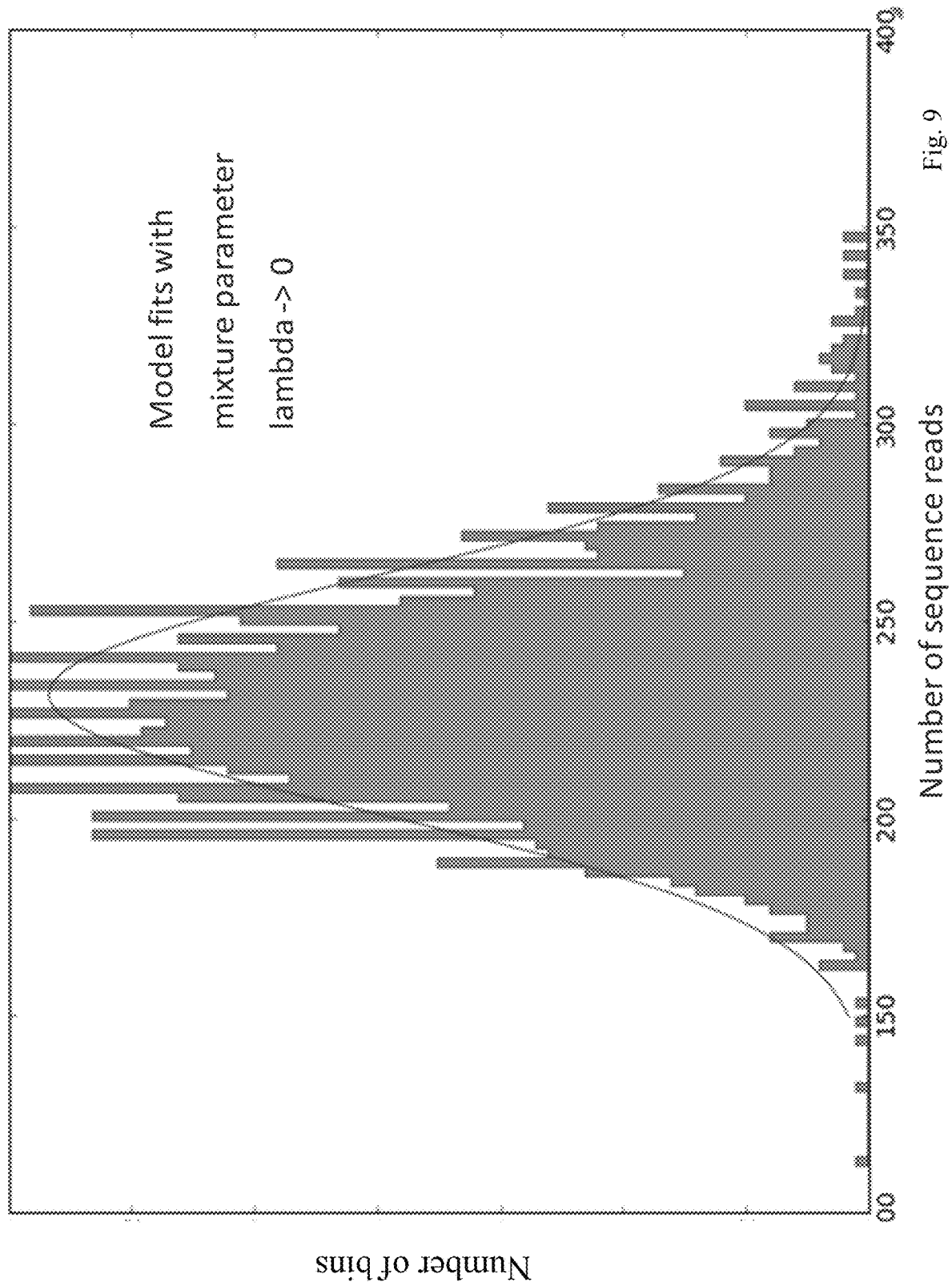
FIG. 9 illustrates how the distribution of the number of sequence reads in the non-replicating cell (cell 51) of FIG. 8 across the plurality of bins indicates that there is a singly ploidy bin population among the plurality of bins, having an average ploidy of 1, in accordance with an embodiment of the present disclosure.

FIG. 8 illustrates a distribution of a number of sequence reads in a non-replicating cell (cell 51), in accordance with an embodiment of the present disclosure. FIG. 9 illustrates that the distribution of the number of sequence reads in the non-replicating cell (cell 51) of FIG. 8 across the plurality of bins indicates that there is a single ploidy bin population among the plurality of bins, having an average ploidy of 1. In particular, in the example of FIGS. 8 and 9, the distribution of the number of sequence reads, visualized in the form of a histogram and a bell-shaped curve overlaying the histogram, has a single peak detected at about 240 sequence reads. This indicates a single ploidy bin population, which corresponds to the non-replicating status of the cell (cell 51).

Figure 11:
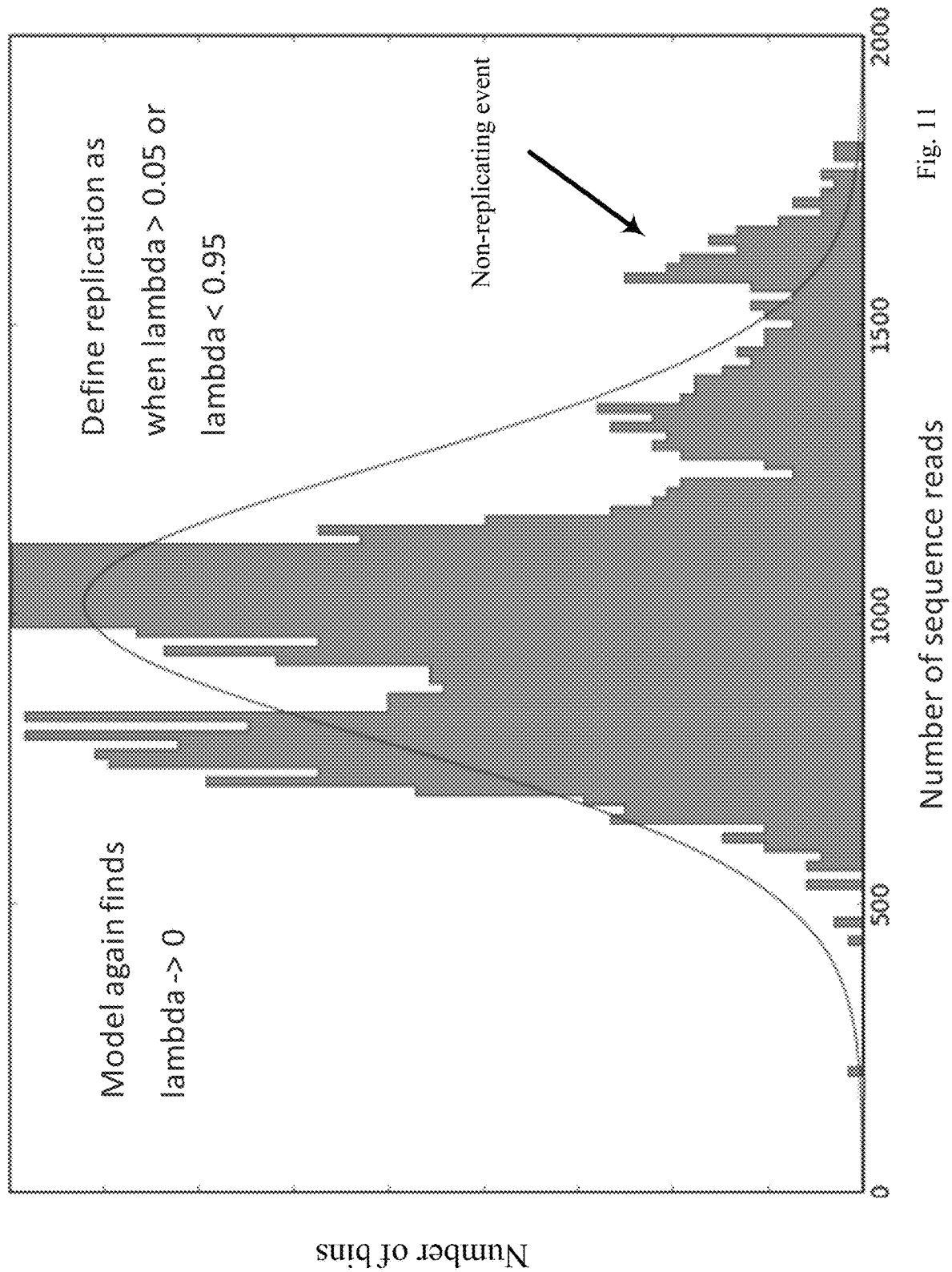
FIG. 11 illustrates how the distribution of the number of sequence reads in the cell undergoing a non-replicating event (cell 15) of FIG. 10 across the plurality of bins indicates that there is non-replicating event occurring in view of the fact that there is a peak that is not explained by the replication and non-replicating profiles, in accordance with an embodiment of the present disclosure.

In a similar manner to FIGS. 7 and 9, FIG. 11 illustrates how the distribution of the number of sequence reads in the cell undergoing a non-replicating event (cell 15) of FIG. 10 across the plurality of bins indicates that there is non-replicating event occurring. In the example of FIG. 11, the peak in the plot generated as a result of an application of a statistical modeling technique is not explained by the replication and non-replicating profiles. In this way, the peak's characteristics are indicative of a non-replicating event, which can be, for example, a tumorous growth which often manifests itself in a chaotic replication. As shown in FIG. 11, although, like in FIG. 9, the processing identifies a single "population" (shown with a bell curve) with a mixture parameter (lambda) approaching 0, the pattern of the sequence reads in FIG. 11 is indicative of the non-replicating event. In particular, in at least one embodiment, the replication can be determined when the mixture parameter is greater than 0.05 or less than 0.95.

As another example, referring back to FIG. 4, a histogram (Single Cell Coverage Histogram) having a certain shape can be displayed based on analysis of a single cell coverage profile (represented by a number of sequence reads) along a chromosome, in accordance with some embodiments of the present disclosure. As shown in FIG. 4, a different respective type of a histogram represents the cell in the early, middle and late replication stages. In particular, in the illustrated example, the histogram representing the early replication stage has one most prominent peak on the left and shows only a hint of a beginning of the cell replication by the slight hump on the right. In the middle replication stage, however, there are two peaks, with the right peak now being distinct. In the late replication stage, the right peak is prominent.

Figure 12A:
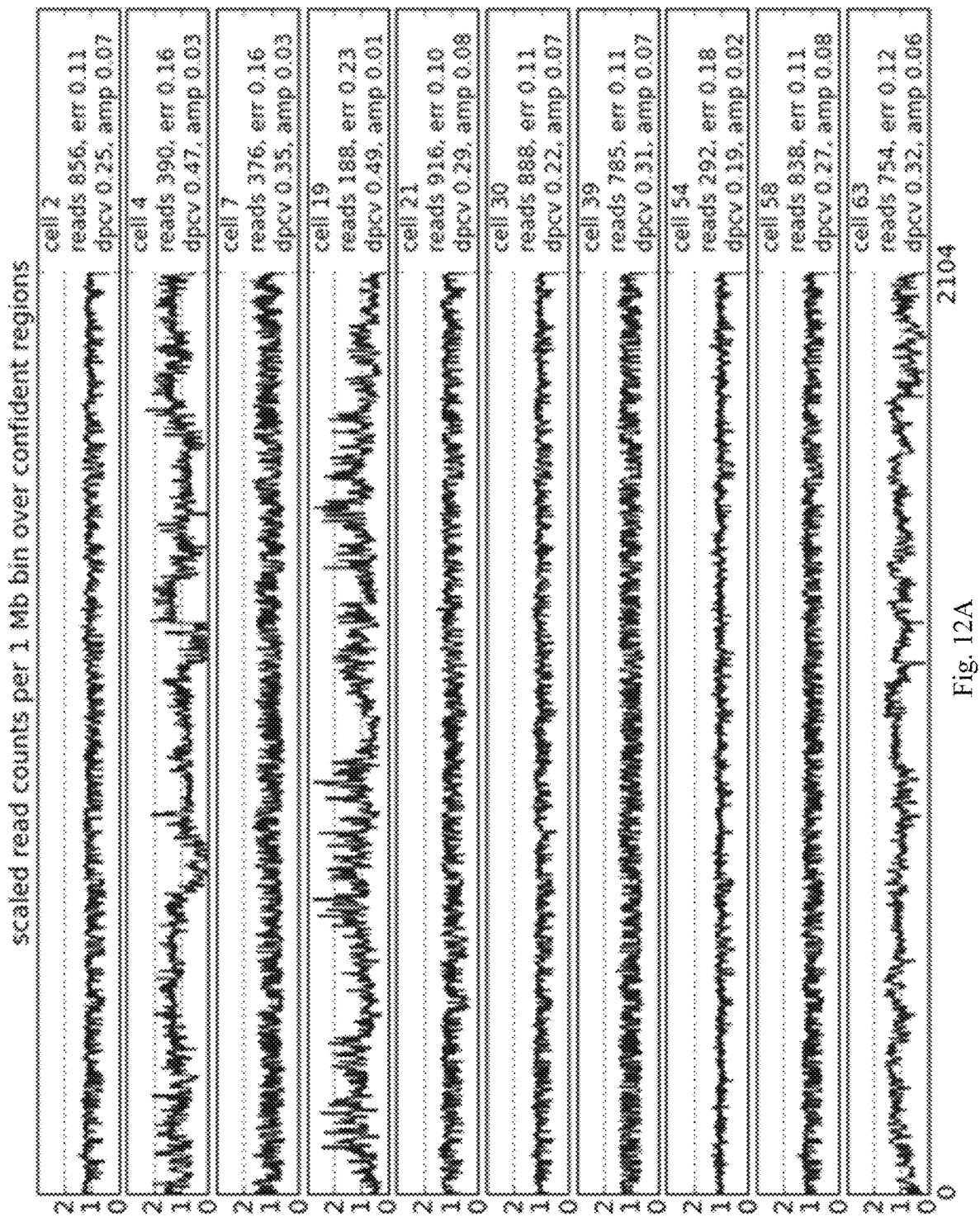
FIGS. 12A and 12B illustrate 17 cells that are identified as replicating in accordance with an embodiment of the present disclosure.
Figure 12B:
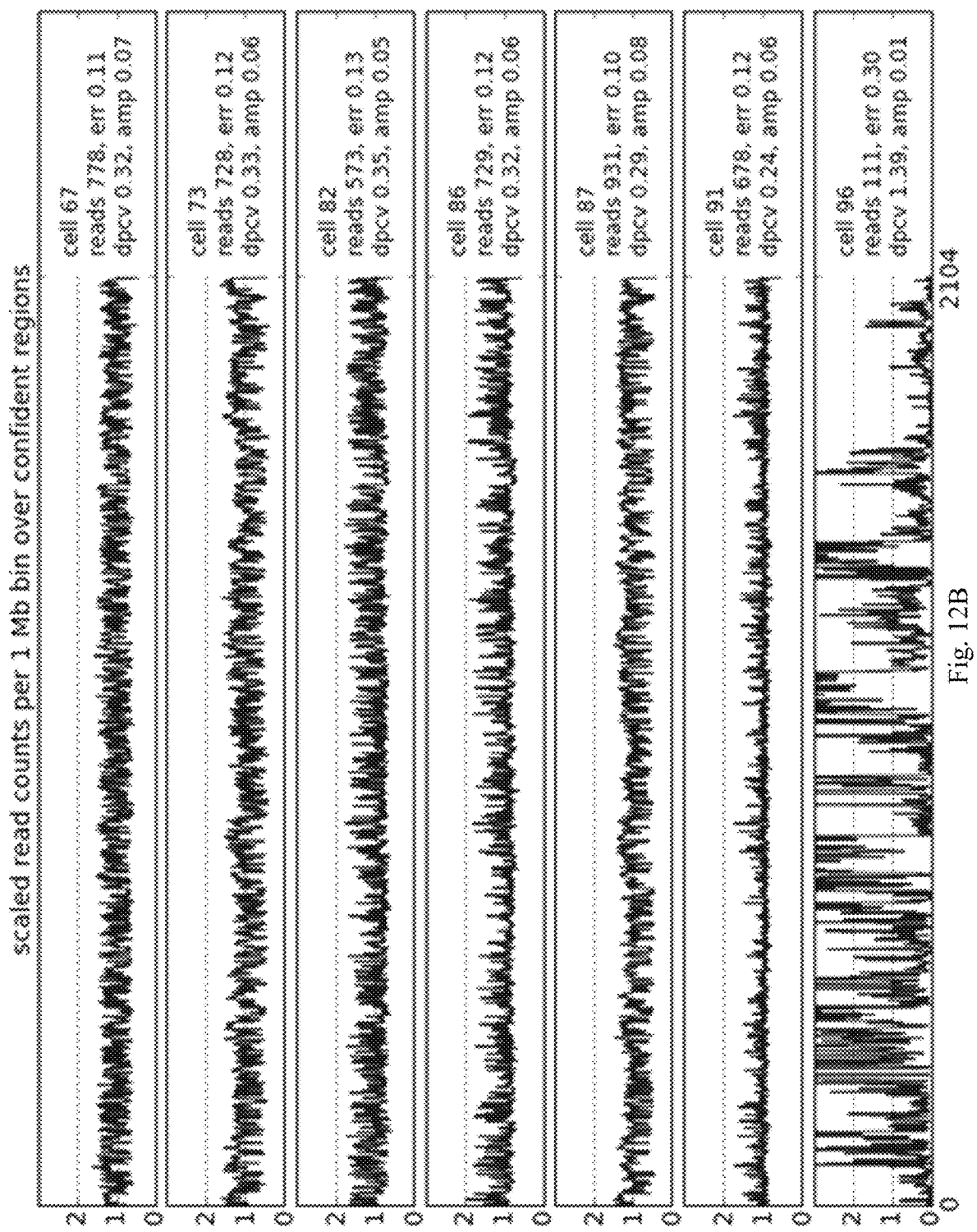

FIGS. 12A to 16B further illustrate examples of visual representations of cells determined to undergo or not to undergo replication. Thus, FIGS. 12A and 12B illustrate 17 cells that are identified as replicating in accordance with an embodiment of the present disclosure. In these figures, scaled nucleic acid read counts per 1 Mb bin over confident regions are shown.

The methods of the present disclosure can be applied to deconvolve heterogeneous cell samples which can encompass somatic cells. Furthermore, the methods can likewise be applied to germ line cells in a sample obtained from any sexually reproducing subject (e.g., a human). The germ line cells can be, for example, primordial germ cells, stem cells, or germ line cells of other types. The stem cells are pluripotent and self-replicating, and the ability to identify a replication status of each cell in a sample of stem cells has many applications, including gene therapy. Also, timing of replication of germ line cells affects mutation rates and can thus define a genome makeup of a mammalian subject. A mutation in germline cell (egg or sperm) can be inherited by an offspring and affect genomic composition of the offspring, resulting, in, for example, a predisposition to a certain type of cancer in the offspring.

Figure 13A:
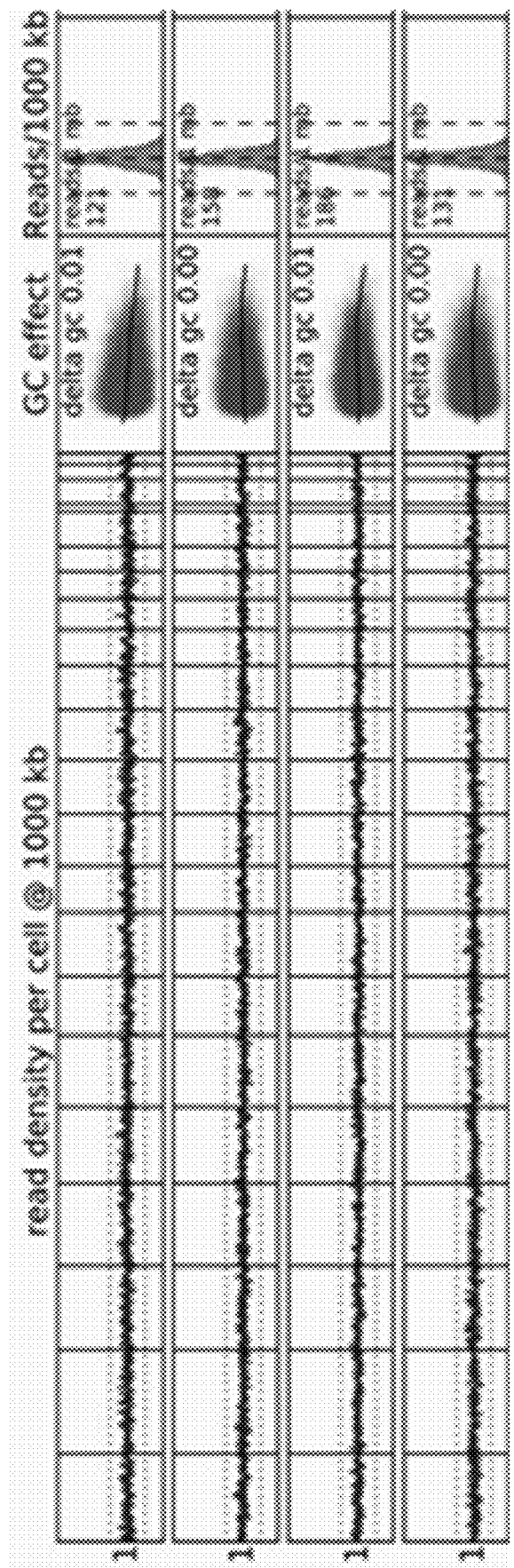
FIG. 13A illustrates mapping, for germ line cells that are not undergoing replication, a nucleic acid sequence of each respective sequence read for each set of sequence reads (each set of sequence reads from a germ line cell that is not undergoing replication) onto a corresponding bin in a plurality of bins, where each respective bin in the plurality of bins represents a different portion of a reference genome of the species, thereby obtaining a nucleic acid sequence read count for each respective bin in the plurality of bins for the germ line cells in accordance with an embodiment of the present disclosure.
Figure 13B:
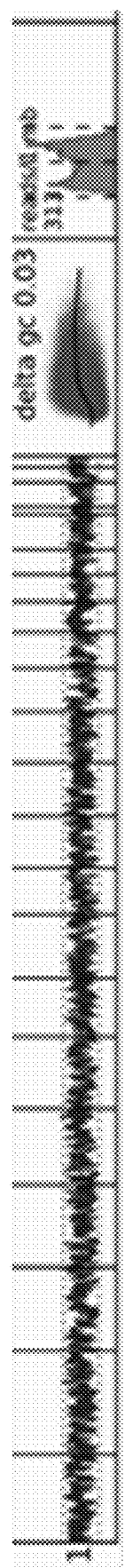
FIG. 13B illustrates mapping, for a germ line cell that is undergoing replication, a nucleic acid sequence of each respective sequence read in a set of sequence reads from the germ line cell that is undergoing replication onto a corresponding bin in a plurality of bins, where each respective bin in the plurality of bins represents a different portion of a reference genome of the species, thereby obtaining a nucleic acid sequence read count for each respective bin in the plurality of bins for the cell in accordance with an embodiment of the present disclosure.

FIG. 13A illustrates mapping, for germ line cells that are not undergoing replication, a nucleic acid sequence of each respective sequence read for each set of sequence reads (each set of sequence reads from a germ line cell that is not undergoing replication) onto a corresponding bin in a plurality of bins. Each respective bin in the plurality of bins represents a different portion of a reference genome of the species. In this way, a nucleic acid sequence read count is obtained for each respective bin in the plurality of bins for the germ line cells in accordance with some embodiments of the present disclosure. As another example, FIG. 13B illustrates mapping, for a germ line cell that is undergoing replication, a nucleic acid sequence of each respective sequence read in a set of sequence reads from the germ line cell that is undergoing replication onto a corresponding bin in a plurality of bins.

Figure 16A:
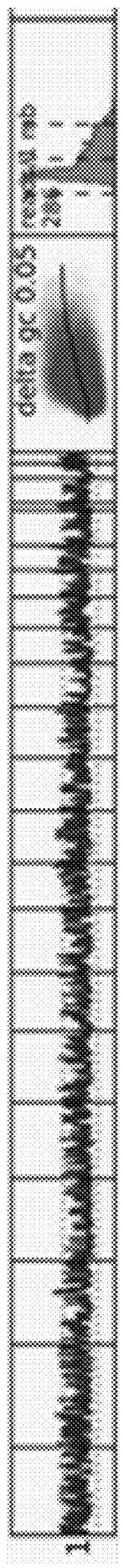
FIG. 16A illustrates mapping, for a germ line cell in an early stage of replication, a nucleic acid sequence of each respective sequence read in a set of sequence reads from the germ line cell onto a corresponding bin in a plurality of bins, where each respective bin in the plurality of bins represents a different portion of a reference genome of the species, thereby obtaining a nucleic acid sequence read count for each respective bin in the plurality of bins for the germ line cell in the early stage of replication in accordance with an embodiment of the present disclosure.
Figure 16B:
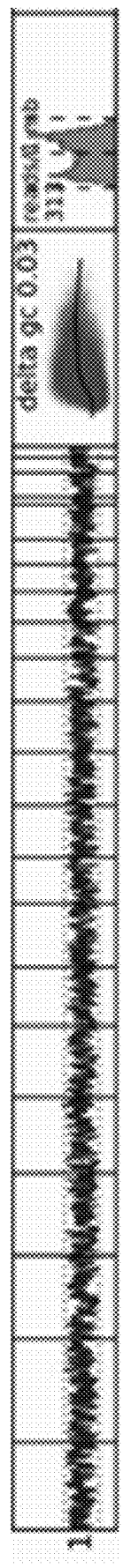
FIG. 16B illustrates mapping, for a germ line cell in a middle stage of replication, a nucleic acid sequence of each respective sequence read in a set of sequence reads from the germ line cell onto a corresponding bin in a plurality of bins, where each respective bin in the plurality of bins represents a different portion of a reference genome of the species, thereby obtaining a nucleic acid sequence read count for each respective bin in the plurality of bins for the germ line cell in the middle stage of replication in accordance with an embodiment of the present disclosure.
Figure 16C:
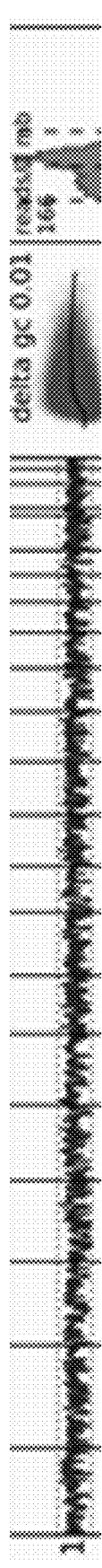
FIG. 16C illustrates mapping, for a germ line cell in a late stage of replication, a nucleic acid sequence of each respective sequence read in a set of sequence reads from the germ line cell onto a corresponding bin in a plurality of bins, where each respective bin in the plurality of bins represents a different portion of a reference genome of the species, thereby obtaining a nucleic acid sequence read count for each respective bin in the plurality of bins for the germ line cell in the late stage of replication in accordance with an embodiment of the present disclosure.

FIGS. 16A, 16B, and 16C illustrate respective examples of visual representation of a result of mapping nucleic acid sequence reads from a germ line cell into bins. In particular, FIG. 16A illustrates an embodiment that involves mapping, for a germ line cell in an early stage of replication, a nucleic acid sequence of each respective sequence read in a set of sequence reads from the germ line cell onto a corresponding bin in a plurality of bins. In this way, a nucleic acid sequence read count is obtained for each respective bin in the plurality of bins for the germ line cell in the early stage of replication in accordance with an embodiment of the present disclosure. FIG. 16B illustrates an embodiment of mapping, for a germ line cell in a middle stage of replication, a nucleic acid sequence of each respective sequence read in a set of sequence reads from the germ line cell onto a corresponding bin in a plurality of bins, thereby obtaining a nucleic acid sequence read count for each respective bin in the plurality of bins for the germ line cell in the middle stage of replication in accordance with an embodiment of the present disclosure. FIG. 16C illustrates mapping, for a germ line cell in a late stage of replication, a nucleic acid sequence of each respective sequence read in a set of sequence reads from the germ line cell onto a corresponding bin in a plurality of bins, thereby obtaining a nucleic acid sequence read count for each respective bin in the plurality of bins for the germ line cell in the late stage of replication in accordance with an embodiment of the present disclosure.

In FIGS. 16A to 16C, each respective bin in the plurality of bins represents a different portion of a reference genome of the species. The techniques in accordance with the present disclosure allow determining additional genomic features that facilitate evaluation of a (non)replication stage of a cell. The features can include, for example, GC content, which is typically higher in replicating regions. See Woodfine et al., 2004, Hum Mol Genet., 13(2), pp. 191-202. Thus, as shown in each of FIGS. 16A, 16B, and 16C, the respective pattern of nucleic acid read counts is shown (e.g., on a user interface of a display of a computing device) in conjunction with the correlation of read counts within a bin with the GC content of a bin ("delta gc"). Also, respective histograms each representing a corresponding computational analysis of a pattern of sequence read counts are shown, as shown in right panels on each of FIGS. 16A-16C. For example, the histogram in FIG. 16A is skewed to the left and is thereby indicative of a pattern of sequence read counts for a germ line cell in an early stage of replication. The histogram in FIG. 16B includes two peaks which are indicative of a pattern of sequence read counts for a germ line cell in a middle stage of replication. FIG. 16C includes the histogram that is skewed to the right and is therefore indicative of a pattern of sequence read counts for a germ line cell in a late stage of replication.

Cancer cells are typically characterized by aneuploidy, which can result from an abnormal mitosis. Many aneuploid cancer cells are polyploid, and polyploidy may occur due to abnormal events such as, for example, disrupted cytokinesis, defective mitotic entry (e.g., skipping or aborting mitosis), or cell fusion. Krajcovic & Overholtzer, 2012, "Mechanisms of ploidy increase in human cancers: a new role for cell cannibalism," Cancer Research, 72(7), pp. 1596-1601. The techniques in accordance with the described embodiments allow distinguishing between stages of cancer development by determining, for example, whether and when a certain event affecting cell ploidy occurs.

Figure 14A:
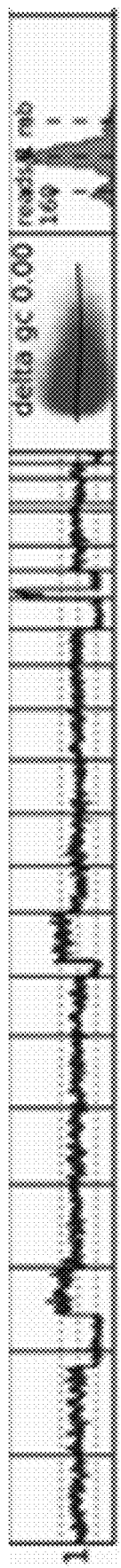
FIG. 14A illustrates mapping, for a cancer cell that is not undergoing replication, a nucleic acid sequence of each respective sequence read in a set of sequence reads from the cancer cell onto a corresponding bin in a plurality of bins, where each respective bin in the plurality of bins represents a different portion of a reference genome of the species, thereby obtaining a nucleic acid sequence read count for each respective bin in the plurality of bins for the cancer cell in accordance with an embodiment of the present disclosure.
Figure 14B:
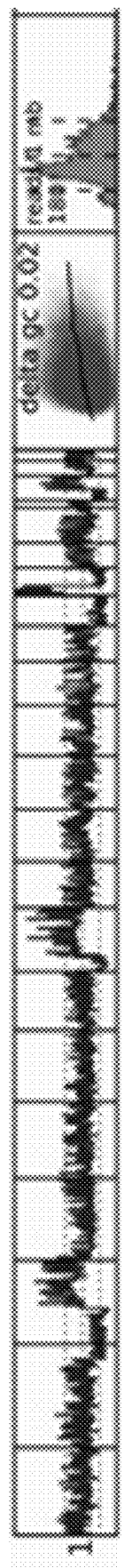
FIG. 14B illustrates mapping, for a cancer cell having the same underlying events as the cell of FIG. 14A with the exception that the cancer cell is undergoing replication, a nucleic acid sequence of each respective sequence read in a set of sequence reads from the cancer cell onto a corresponding bin in a plurality of bins, where each respective bin in the plurality of bins represents a different portion of a reference genome of the species, thereby obtaining a nucleic acid sequence read count for each respective bin in the plurality of bins for the cancer cell in accordance with an embodiment of the present disclosure.

In some embodiments, a sample including one or more cancer cells can be deconvolved in accordance with embodiments of the present disclosure. The described techniques allow determining whether or not a cancer cell is undergoing a normal replication. For example, FIG. 14A illustrates mapping, for a cancer cell that is not undergoing replication, a nucleic acid sequence of each respective sequence read in a set of sequence reads from the cancer cell onto a corresponding bin in a plurality of bins, thereby obtaining a nucleic acid sequence read count for each respective bin in the plurality of bins for the cancer cell in accordance with an embodiment of the present disclosure. In contrast, FIG. 14B illustrates mapping, for a cancer cell having the same underlying events as the cell of FIG. 14A with the exception that the cancer cell is undergoing replication, a nucleic acid sequence of each respective sequence read in a set of sequence reads from the cancer cell onto a corresponding bin in a plurality of bins. In this way, a nucleic acid sequence read count for each respective bin in the plurality of bins for the cancer cell is obtained in accordance with an embodiment of the present disclosure. In FIGS. 14A and 14B, each respective bin in the plurality of bins represents a different portion of a reference genome of the species. Similar to the examples in FIGS. 16A-16C, the GC content and the respective histograms are shown in FIGS. 14A and 14B along with the visual representation of the nucleic acid sequences mapped onto the plurality of bins.

Figure 15A:
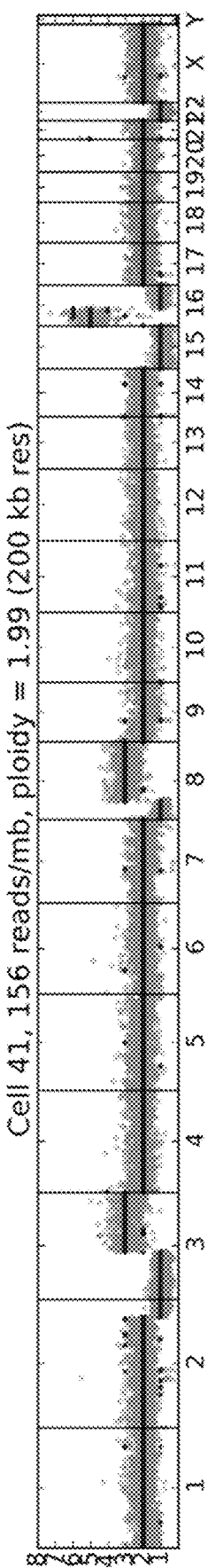
FIG. 15A illustrates mapping, for a cancer cell that is not undergoing replication, a nucleic acid sequence of each respective sequence read in a set of sequence reads from the cancer cell onto a corresponding bin in a plurality of bins, where each respective bin in the plurality of bins represents a different portion of a reference genome of the species, thereby obtaining a nucleic acid sequence read count for each respective bin in the plurality of bins for the cancer cell in accordance with an embodiment of the present disclosure.
Figure 15B:
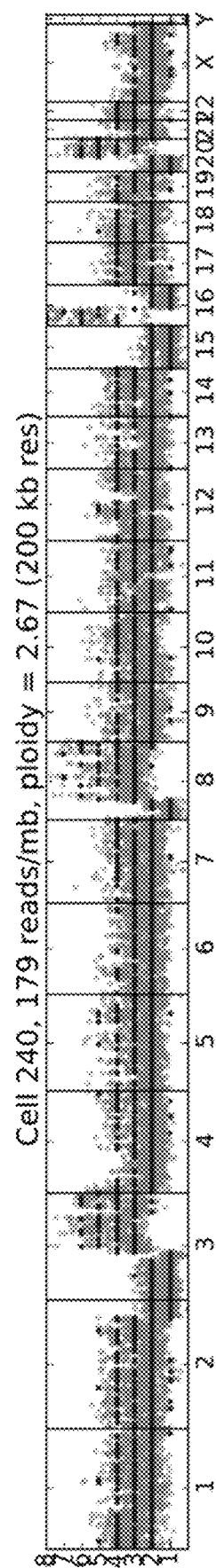
FIG. 15B illustrates mapping, for a cancer cell having the same underlying events as the cell of FIG. 15A with the exception that the cancer cell is undergoing replication, a nucleic acid sequence of each respective sequence read in a set of sequence reads from the cancer cell onto a corresponding bin in a plurality of bins, where each respective bin in the plurality of bins represents a different portion of a reference genome of the species, thereby obtaining a nucleic acid sequence read count for each respective bin in the plurality of bins for the cancer cell in accordance with an embodiment of the present disclosure.

FIG. 15A illustrates mapping, for a cancer cell that is not undergoing replication, a nucleic acid sequence of each respective sequence read in a set of sequence reads from the cancer cell onto a corresponding bin in a plurality of bins, thereby obtaining a nucleic acid sequence read count for each respective bin in the plurality of bins for the cancer cell in accordance with an embodiment of the present disclosure. FIG. 15B illustrates mapping, for a cancer cell having the same underlying events as the cell of FIG. 15A with the exception that the cancer cell is undergoing replication, a nucleic acid sequence of each respective sequence read in a set of sequence reads from the cancer cell onto a corresponding bin in a plurality of bins, thereby obtaining a nucleic acid sequence read count for each respective bin in the plurality of bins for the cancer cell in accordance with an embodiment of the present disclosure.

As shown in FIGS. 15A and 15B, respective visual representation of a plurality of bins illustrate certain patterns of nucleic acid sequence read counts. Mitotic filters can be applied to each of the patterns to determine whether the pattern is indicative of a cell undergoing replication and/or what stage of the replication is inferred.

In some embodiments, a distribution of nucleic acid reads is compared to a distribution characteristic of an unperturbed clonal population. The DNA replication status among cells in a clone or clonal population can be used to indicate a cell cycle status of each of those cells. The collective distribution of the cell cycle statuses allows for the inference of characteristics of the cellular replication of these clonal populations. For example, it can be determined what fraction of cells is replicating and/or how the cell replication is affected by a perturbation (e.g., a drug or other treatment). As discussed above, the systems and methods in accordance with the present disclosure allow identifying non-replicating events (e.g., cancer), as shown, e.g., in connection with FIGS. 10 and 11.

Accordingly, the described embodiments can be used to determine, by detecting non-replication events in a clonal population, a cancer status of the clonal population, as well as to determine how perturbations (e.g., anti-cancer drugs or other treatment(s)) affect such non-replicating events. In this way, the systems and methods in accordance with the present disclosure can be used to determine the efficacy of anti-cancer drugs, the progress of the treatment, and other features that are associated with a replication status of a cell. Any other characteristics of the cell population can be determined based on the determining of cell cycle statuses of the cells in the clonal population.

Block 236—Obtain a set of nucleic acid sequence reads from each cell in a second clonal population, thereby obtaining a second plurality of sets of nucleic acid sequence reads. Referring to block 236 of FIG. 2C, the method in accordance with some embodiments of the present disclosure further includes obtaining a set of nucleic acid sequence reads from each cell in a second clonal population comprising a second plurality of cells of the species through a single cell sequencing process, thereby obtaining a second plurality of sets of nucleic acid sequence reads. Each respective set of nucleic acid sequence reads in the second plurality of sets of nucleic acid sequence reads is from a single cell in the second plurality of cells. This process can be performed similar to the process at block 204 of FIG. 2A.

At block 236, the method includes mapping a nucleic acid sequence of each respective sequence read in each respective set of sequence reads in the second plurality of sets of nucleic acid sequence reads onto a corresponding bin in the plurality of bins. The mapping can be performed similar to the mapping at block 226 of FIG. 2B. The method further includes, for each respective cell in the second plurality of cells, assigning the respective cell into one of the plurality of groups based upon a pattern of sequence read counts of the respective cell across the plurality of bins, where the assigning determines whether the respective cell is to be assigned to the first group by applying the first mitotic filter to the nucleic acid read count of respective bins in the plurality of bins obtained for the respective cell.

Furthermore, the method further includes comparing a relative assignment of cells in the first plurality of cells and the second plurality of cells to individual groups in the plurality of groups. In this way, trends in the relative assignment of cells in the first and second plurality of cells can be compared. For instance, the first and second plurality of cells can be from the same subject at different time points. In such instances, the relative assignment of the cells is informative of a change in status of the subject between the two time points. As another example, the first and second plurality of cells can be respectively from a first and second subject, where the first subject is afflicted with a disease condition and the second subject is not. In such instances, differences in the relative assignment of the cells between the first and second subject is informative as to whether the relative assignment is diagnostic (or causal for) the disease condition, particularly if this analysis is performed across a cohort of subjects, some of which have the disease condition, and some of which do not have the disease condition. As still another example, the first and second plurality of cells can be respectively from a first and second subject, where the first subject has been exposed to a perturbation (e.g., a candidate drug) and the second subject has not. In such instances, differences in the relative assignment of the cells between the first and second subject is informative as to whether the perturbation has an effect, particularly if this analysis is performed across a cohort of subjects, some of which have been exposed to the perturbation, and some of which have not been exposed to the perturbation.

In some embodiments, a method is provided that allows evaluating an effect of a DNA repair inhibitor on a status of replication of cells in a biological sample from an organism. An organism normally tends to remain in an equilibrium state, such that any defect or abnormality in the DNA structure results in activation of a DNA repair mechanism to maintain genomic stability. Various endogenous and exogenous factors can cause a damage of the DNA structure. Human DNA, for example, is subjected to a large number of factors, both external and internal, that are potentially carcinogenic. DNA repair is therefore an important function of any cell of an organism.

Defects in a DNA repair mechanism can lead to instability of a genome, and such defects are often a cause and/or a manifestation of a cancer. In fact, cancer is typically defined as a disease of DNA repair. At the same time, for cancer cells to replicate their DNA and divide, the cancer cells require multiple DNA repair pathways. Cancerous cell populations thus become dependent on a specific, defective DNA repair mechanism that allows the cancer cells to survive and proliferate. Cancer cells undergo a continuous proliferation, and the specific DNA repair pathways that sustain the cancer become prevalent in the cells. DNA repair pathways of cancers can include DNA repair mutations or reliance on alternative mechanisms. A significant fraction of cancers is characterized by DNA repair defects, as described, for example, by Nickoloff et al., 2017, "Drugging the Cancers Addicted to DNA Repair," J. Natl. Cancer Inst. 109(11). One prominent example of cancer dependence on an alternative DNA repair mechanism is in breast or ovarian cancers with mutated BRCA1 or BRCA2 genes. The BRCA1 and BRCA2 genes normally produce tumor suppressor proteins that participate in repairing DNA double-strand breaks. But when either of these genes is mutated, the damaged DNA in a cell is not properly repaired. Moreover, for the mutated BRCA1 or BRCA2 genes to persist, these genes become dependent on another DNA repair component, PARP1. See Shaheen et al., 2011, "Synthetic lethality: exploiting the addiction of cancer to DNA repair," Blood 117(23), pp. 6074-6082.

Accordingly, an inhibition of such "imposter" DNA repair pathways in cancer cells allows preventing these cells from replicating. An anti-cancer drug or another treatment can be used to disrupt or inhibit a DNA repair pathway of a cancer cell. For example, PARP inhibitors represent therapeutic agents directed at targeting cancers with defective DNA-damage repair. Non-limiting examples of PARP inhibitors include iniparib, PARPi, and olaparib. DNA repair inhibitors may target PARP, DNA-PK, MGMT, or other proteins. Another example of a DNA repair inhibitor includes an ATR inhibitor.

Development of DNA repair inhibitors, particularly small-molecule inhibitors, is a promising area of discovering ways to damage tumor cells. A therapy involving DNA repair inhibitors depends on biomarkers or markers which allow evaluating the efficacy of the potential DNA repair inhibitor, monitoring progress of a treatment, determining a patient's condition, and evaluating other factors and events related to cancer prevention and treatment.

Accordingly, referring to FIG. 2D, in some aspects, a method of evaluating a DNA repair inhibitor is provided. In some embodiments, the method is performed as follows:

Block 302. One aspect of the present disclosure provides a computer system, a non-limiting example of which is illustrated in FIG. 1 as a computer system 100. The computer system 100 comprises one or more processing cores or processors 102 and memory 104, which stores one or more programs for execution by the one or more processors, for performing the one or more programs method in accordance with the present disclosure. The memory 104 can store at least a portion of the one or more programs in the persistent memory 112 (FIG. 1). FIG. 2D illustrates an example method in accordance with an embodiment of the present disclosure.

Block 30—Obtain a set of nucleic acid sequence reads from each cell in the first plurality of cells through a single cell sequencing process. The first plurality of cells can be from an organism of a species that has been exposed to the DNA repair inhibitor. In this way, a first plurality of sets of nucleic acid sequence reads is obtained, where each respective set of nucleic acid sequence reads in the first plurality of sets of nucleic acid sequence reads is from a single cell in the first plurality of cells.

As discussed above, the DNA repair inhibitor can be any suitable compound. Non-limiting examples of the compound include an organic compound having a molecular weight of less than 2000 Daltons. In some embodiments, the compound is an organic compound that satisfies the Lipinski rule of five criteria can be an organic compound that satisfies at least two criteria of the Lipinski rule of five criteria. The compound can also be a poly ADP ribose polymerase (PARP) inhibitor, or any other type of a compound having properties (or suspected having properties) of a DNA repair inhibitor.

The organism of a species can be exposed to the DNA repair inhibitor for a certain time period prior to the obtaining step at block 304. For example, in some embodiments, the organism is exposed to the DNA repair inhibitor for at least one hour prior to performing the obtaining step. The organism can alternatively be exposed to the DNA repair inhibitor for less than one hour prior to performing the obtaining step. Various doses of the DNA repair inhibitor can be administered to the organism to evaluate the DNA repair inhibitor. Any other parameter(s) related to exposing the organism of a species to the DNA repair inhibitor being evaluated can be varied additionally or alternatively.

Block 306—Map a nucleic acid sequence of each respective sequence read in each respective set of sequence reads onto a corresponding bin 124 in a plurality of bins. Each respective bin in the plurality of bins represents a different portion of a reference genome of the species. In this way a nucleic acid sequence read count is obtained for each respective bin in the plurality of bins for each respective cell in the first plurality of cells.

Block 308—Independently segregate each respective cell in the first plurality of cells into one of a plurality of cell classes 130. A cell can be segregated into a class based on a presence, absence, or amount of a marker or a marker set in the respective cell. Single cell DNA sequencing allows for inference of a state of a cell. Thus, each cell within the total set of cells in a sample can be mapped to a clonal subpopulation that this cell belongs to. The clonal subpopulation can be defined, for example, by mutational events that are common to that subpopulation. Non-limiting examples of mutational events include copy number variants (CNVs), single nucleotide variants (SNVs), and other mutational events. Predictive markers, which can be in the form of mutations or mutational events, serve as indicators of the cell's state and allow determining the effect of a DNA repair inhibitor on the cell.

Figure 5:
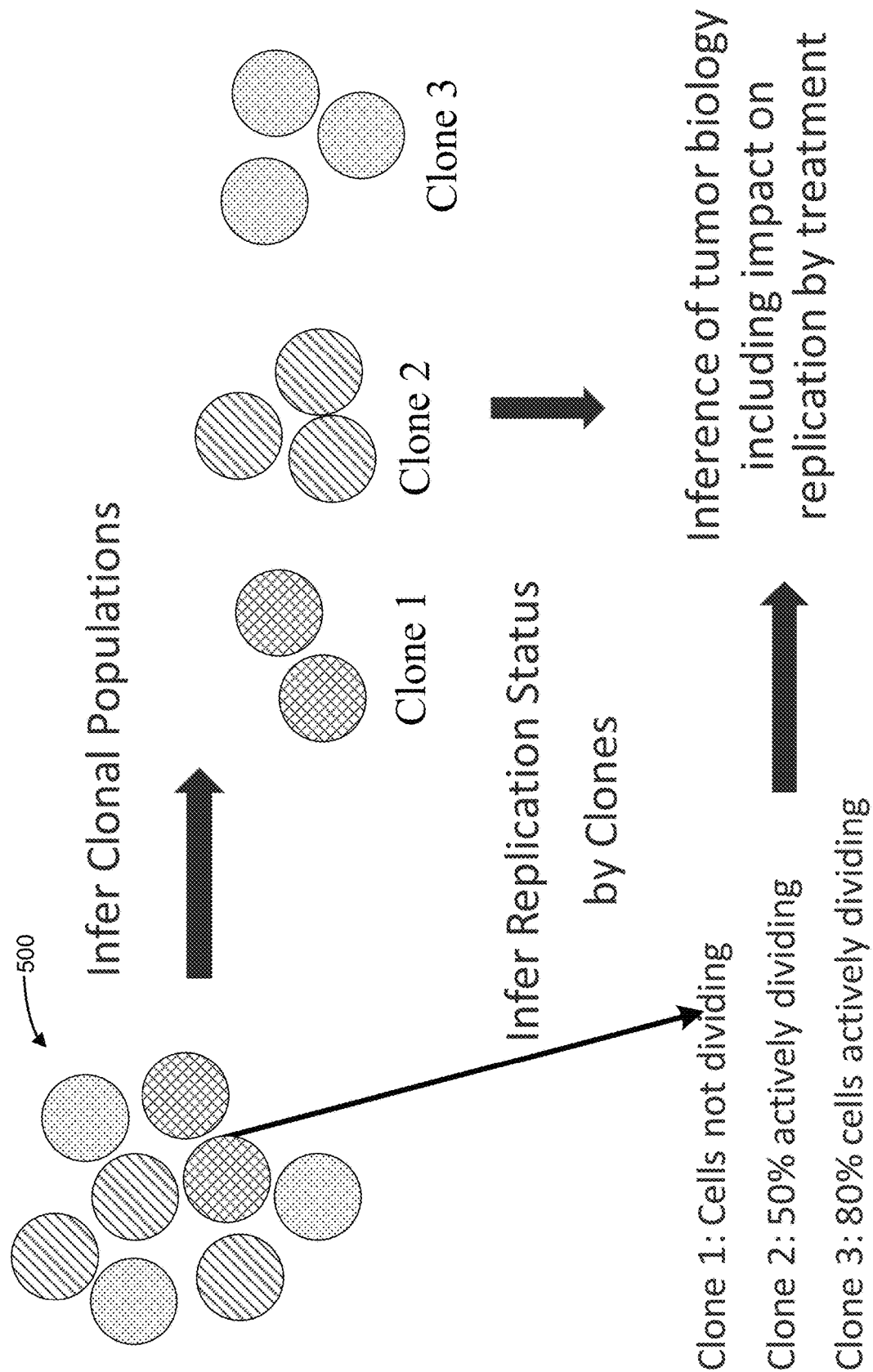
FIG. 5 illustrates independently segregating each respective cell in a plurality of cells into one of a plurality of cell classes based on a presence, absence, or amount of a marker or a marker set in the respective cell and, for each respective cell in each respective cell class in the plurality of cell classes, assigning the respective cell into one of a plurality of groups based upon a pattern of sequence read counts of the respective cell across the plurality of bins, where a first group in the plurality of groups represents a first mitotic stage, a second group in the plurality of groups represents a non-mitotic stage in accordance with an embodiment of the present disclosure.

FIG. 5 illustrates a sample 500 comprising a plurality of cells which form a heterogeneous population. In the embodiment of FIG. 5, the sample 500 is treated with an anti-cancer agent such as, e.g., a DNA repair inhibitor. The cells in the heterogeneous population of the sample 500 can respond (or not) differently to the DNA repair inhibitor. Each respective cell in a plurality of cells in the sample 500 is independently segregated into one of a plurality of cell classes based on a presence, absence, or amount of a marker or a marker set in the respective cell. Further, for each respective cell in each respective cell class in the plurality of cell classes, the respective cell is assigned into one of a plurality of groups based upon a pattern of sequence read counts of the respective cell across the plurality of bins. The plurality of groups can correspond to respective different mitotic stages. For example, a first group in the plurality of groups can represent a first mitotic stage and a second group in the plurality of groups can represent a non-mitotic stage in accordance with some embodiments of the present disclosure.

It should be appreciated that the first mitotic stage and the second mitotic stage can each be more than one respective first and second mitotic stages. Thus, FIG. 5 illustrates schematically that three clonal populations can be inferred from the sample 500. In this example, a first clonal population ("Clone 1," marked with a crosshatch pattern) includes cells that are dividing, a second clonal population ("Clone 2," marked with a diagonal parallel lines pattern) includes cells 50% of which are actively dividing, and a third clonal population ("Clone 3," marked with a dotted pattern) includes cells 80% of which are actively dividing. As a result, the plurality of cells in the sample 500 are characterized that such that inference on tumor biology is made, which can include determination of the impact of administered treatment on the cells in the sample 500.

Referring back to FIG. 2D, in some embodiments, the method of evaluating the DNA repair inhibitor further includes:

Block 310—For each respective cell class, evaluate an average sequence read count for a predetermined subset of the plurality of bins across the cells of that cell class. The average sequence read count can be used as a collective indicator of the gene expression in cells in the cell class. It should be appreciated, however, that another collective measure of the sequence read counts for a subset of bins across cells segregated into a respective cell class can be used additionally or alternatively.

Block 312 —Compare the average sequence read count for the predetermined subset of the plurality of bins across the plurality of cell classes, thereby evaluating the DNA repair inhibitor. With reference to block 312 of FIG. 2D, the comparison of respective average sequence read counts among cell classes allows determining the effect of the DNA repair inhibitor on the plurality of cells. In this way, for example, the efficacy of the DNA repair inhibitor in suppressing abnormal DNA repair mechanism in cancer cells can be evaluated. It should be appreciated that, as referred herein, the DNA repair inhibitor can be any suitable agent that may have a potential in arresting proliferation of cancer cells. Thus, the DNA repair inhibitor can be an agent that is not yet proven to be an acceptable DNA repair inhibitor but the agent that is being tested for such potential.

Regardless of the specific type of the DNA repair inhibitor evaluated in accordance with certain embodiments of the present disclosure, the evaluation of the DNA repair inhibitor can be followed by an action taken based on the evaluation. A decision can be made regarding use of the DNA repair inhibitor depending on its effectiveness that is in turn determined as a result of the evaluation. For example, a treatment regimen can be developed which involves administering the DNA repair inhibitor to a subject in need of cancer treatment. Various aspects of a treatment, e.g., a suitable dosage, frequency of treatment, etc., can be determined based on results of the evaluation of the DNA repair inhibitor in accordance with the present disclosure In some embodiments, the single cell sequencing process is a single cell DNA sequencing process and each nucleic acid sequence read in each set in the first plurality of sets of nucleic acid sequence reads is a DNA sequence. In other embodiments, the single cell sequencing process is a single cell RNA sequencing process and each nucleic acid sequence read in each set in the first plurality of sets of nucleic acid sequence reads is an RNA sequence. In some embodiments, regardless of whether the single cell sequencing process is a single cell DNA sequencing process or a single cell RNA sequencing process, each respective set of nucleic acid sequence reads can collectively represent at least one percent of the genome of the cell corresponding to the respective set of nucleic acid sequence reads. Any portion of the cell genome can be represented by the nucleic acid sequence reads, and less than one percent of the genome of the cell can be thereby represented.

In some embodiments, in the method described in connection with FIG. 2D, the marker or the marker set comprises a predetermined genetic mutation and the segregating of each cell into one of a plurality of cell classes determines whether the respective cell includes the predetermined genetic mutation. When the respective cell includes the predetermined genetic mutation, the respective cell is deemed to belong to a first class in the plurality of cell classes. Alternatively, when the respective cell does not include the predetermined genetic mutation, the respective cell is deemed to belong in a class in the plurality of cell classes other than the first class. For example, cells with a genetic mutation can be cancerous cells, whereas cells without that mutation can be non-cancerous cells. As another example, cells having a genetic mutation can be cancerous cells, and cells without the mutation can be a portion of the cancerous cell that are exhibiting a response to a certain DNA repair inhibitor.

In some embodiments, the predetermined genetic mutation is a single nucleotide polymorphism, an insertion, a deletion, or an inversion. The genetic mutation can be any type of a mutation. For example, the genetic mutation can be in the form of a cell marker indicative of a stage of cancer, such as, e.g., BRCA1- or BRCA2-mutated breast cancer. See Kelley et al., 2014, "Targeting DNA repair pathways for cancer treatment: what's new?", Future Oncol. 10(7), pp. 1215-1237.

In some embodiments, the marker or the marker set is a plurality of predetermined genetic mutations and the segregating (at block 308 in FIG. 2D) determines whether the respective cell includes each predetermined genetic mutation in the plurality of predetermined genetic mutations. In such embodiments, when the respective cell includes each predetermined genetic mutation in the plurality of predetermined genetic mutations, the respective cell is deemed to belong to a first class in the plurality of cell classes. When the respective cell does not include each predetermined genetic mutation in the plurality of predetermined genetic mutations, the respective cell is deemed to belong in a class in the plurality of cell classes other than the first class.

The predetermined genetic mutation can be any type of a mutation. For example, in some embodiments, each predetermined genetic mutation in the plurality of predetermined genetic mutations is a single nucleotide polymorphism, an insertion, a deletion, or an inversion.

In some embodiments, the marker is a threshold number of genetic mutations mapping to one or more predetermined portions of the reference genome. In such embodiments, the segregating (at block 308 in FIG. 2D) determines whether the respective cell includes the threshold number of genetic mutations. In this way, the respective cell is deemed to belong either to a first class in the plurality of cell classes or to in a class in the plurality of cell classes other than the first class, based on whether or not the cell includes the threshold number of genetic mutations.

The threshold number of genetic mutations can be determined in various ways. For example, in some embodiments, the threshold number is determined by evaluating an average number and the standard deviation of the average number of mutations in the one or more predetermined portions of the reference genome across a population of cells of the species that have not been exposed to the DNA repair inhibitor. The threshold number can therefore represent a certain number of standard deviations above an average number of mutations in a reference population. As another example, in some embodiments, the threshold number is determined by evaluating an average number and standard deviation of the average number of mutations in the one or more predetermined portions of the reference genome across the first plurality of cells. The threshold number can therefore represent a certain number of standard deviations above the average number of mutations in the first plurality of cells. Each genetic mutation mapping to the one or more predetermined portions of the reference genome can be a single nucleotide polymorphism, an insertion, a deletion, an inversion, or any other type of mutation in the one or more predetermined portions of the reference genome.

The one or more predetermined portions of the reference genome can be any gene or more than one gene. In some embodiments, the gene(s) can be involved in DNA repair and can therefore play role in cancer detection and treatment. Thus, the one or more predetermined portions of the reference genome can consist of, for example, the X-Ray Repair Cross Complementing 2 (XRCC2) gene, the X-Ray Repair Cross Complementing 3 (XRCC3) gene, the RAD54 gene, the H2AX gene the phosphatase and tensin homolog gene, and/or the ATM gene. A mutation in the genes can be indicative of a degree of DNA damage in a cell. For example, the XRCC2 and XRCC3 genes are involved in the repair of DNA double-strand breaks by homologous recombination and maintain chromosome stability. The RAD54 gene (in *Saccharomyces cerevisiae*) and similar RAD54L gene (in *Homo sapiens*) encodes a protein that is involved in DNA repair and homologous recombination.

The ATM gene encodes ATM serine/threonine kinase that assists cells in recognizing damaged or broken DNA strands. The ATM serine/threonine is recruited and activated by DNA double-strand breaks, and it initiates DNA repair. Phosphorylation of H2AX to thereby form γ-H2AX is a marker for DNA damage (formation of double-stranded brakes), and the level of γ-H2AX in a cell therefore correlates with a degree of DNA damage in the cell. Ji et al. (2017). Mutations in the phosphatase and tensin homolog (PTEN) are associated with a spectrum of clinical disorders and an increased risk of cancers. An anti-cancer agent (e.g., a DNA repair inhibitor) can thus be evaluated using the techniques of the present disclosure, by assessing DNA damage response of a cell as a result of application of the agent.

In the method of evaluating a DNA repair inhibitor, the species can be human. Each bin in the plurality of bins can be the same size, and the plurality of bins can collectively encompass at least three percent of the entire human genome. In some embodiments, the plurality of bins consists of between one hundred and two thousand bins. However, the plurality of bins can include any other number of bins, including less than one hundred bins or greater than two thousand bins.

In some aspects, the method of evaluating a DNA repair inhibitor in accordance with some embodiments of the present disclosure includes comparing a clonal population that was exposed to the DNA repair inhibitor to another clonal population comprising a second plurality of cells. The another clonal population can be, for example, an unperturbed clonal cell population that was not exposed to any therapeutic agent.

The second plurality of cells, which can be from the same species, can be processed similar to the first plurality of cells from an organism of a species that has been exposed to the DNA repair inhibitor. Thus, in some embodiments, the method includes obtaining a set of nucleic acid sequence reads from each cell in a second plurality of cells of the species through a single cell sequencing process, thereby obtaining a second plurality of sets of nucleic acid sequence reads. Each respective set of nucleic acid sequence reads in the second plurality of sets of nucleic acid sequence reads is from a single cell. The method further involves mapping a nucleic acid sequence of each respective sequence read in each respective set of sequence reads in the second plurality of sets of nucleic acid sequence reads onto a corresponding bin in the plurality of bins, and, for each respective cell in the second plurality of cells, independently segregating the respective cell into one of the plurality of cell classes based on the presence, absence, or amount of the marker or the marker set in the respective cell. Further, for each respective cell class in the plurality of classes, an average sequence read count is evaluated for a predetermined subset of the plurality of bins across the cells of the respective cell class in the second plurality of cells. The average sequence read counts can be normalized. For example, for each respective cell class in the plurality of cell classes, an average sequence read count can be compared for the respective cell class for the predetermined subset of the plurality of bins obtained from the first plurality of cells versus the second plurality of cells. In some implementations, additionally or alternatively, the average sequence read count can be processed in other ways.

In some embodiments, cells in a heterogeneous cell population, or in cell population that is suspected to be heterogeneous, are segregated into classes based on a presence, absence, or amount of a marker or a marker set. Each cell within a class is then assigned into a group based upon a pattern of sequence read counts for that cell. In this way, for example, it can be determined that, in a certain cell class, a group (e.g., percentage) of the cells is in a first mitotic stage, and another group of the cells in that class is in a different mitotic stage.

FIG. 2E illustrates a method of deconvolving a heterogeneous population of cells comprising a first plurality of cells. The method comprises the following steps:

402. A computer system 100 having one or more processors 102 and memory 104 storing one or more programs for execution by the one or more processors. The one or more programs comprising instructions for performing the following method of evaluating a DNA repair inhibitor.

404—Obtain a set of nucleic acid sequence reads from each cell in a first plurality of cells through a single cell sequencing process. The first plurality of cells is from an organism of a species that has been exposed to the DNA repair inhibitor. In this way, a first plurality of sets of nucleic acid sequence reads is obtained, where each respective set of nucleic acid sequence reads in the first plurality of sets of nucleic acid sequence reads is from a single cell in the first plurality of cells.

406—Map a nucleic acid sequence of each respective sequence read in each respective set of sequence reads onto a corresponding bin 124 in a plurality of bins. Each respective bin in the plurality of bins represents a different portion of a reference genome of the species. In this way, a nucleic acid sequence read count is obtained for each respective bin in the plurality of bins for each respective cell in the first plurality of cells.

408—Independently segregate each respective cell in the first plurality of cells into one of a plurality of cell classes 130. In this example, each cell is segregated into a class based on a presence, absence, or amount of a marker or a marker set in the respective cell. The cell can be segregated into one class. In some implementations, a cell can be assigned, with a certain probability or in association with another value characterizing cell assignment to a class, to more than one class. The marker or marker set can be any type of a marker, as discussed above. For example, the marker or marker set can be one or more genetic mutations, a threshold number of genetic mutations, or a maker of any other type. A genetic mutation can be a single nucleotide polymorphism, an insertion, a deletion, or an inversion.

410—For each respective cell in each respective cell class, assign the respective cell into one of a plurality of groups based upon a pattern of sequence read counts of that cell across the plurality of bins. A first group in the plurality of groups represents a first mitotic stage, and a second group in the plurality of groups represents a non-mitotic stage. In this way, it is determined whether the respective cell is to be assigned to the first group by applying a first mitotic filter to the nucleic acid read count of respective bins in the plurality of bins obtained for the respective cell. FIG. 5, discussed above, illustrates assignment of cells to respective clonal populations.

412—Compare a proportion of cells in each cell class in the plurality of cell classes that are in the first mitotic stage. The first mitotic stage can be any stage of mitosis. For example, it can be an early mitotic stage, a middle mitotic stage, a late mitotic stage, or any other mitotic stage. In some cases, the mitotic stage can be characterized, for example, by a percentage of cells in a group/class that are undergoing mitosis. Also, the first mitotic stage can be a stage where no mitosis is detected.

In some embodiments, the cells are independently segregated into cell classes based on markers or absence of markers. In some embodiments, the marker or the marker set comprises a predetermined genetic mutation, and the segregating (at block 408 in FIG. 2E) determines whether the respective cell includes one or more predetermined genetic mutations. When the respective cell includes the predetermined genetic mutation(s), the cell is deemed to belong to a first class in the plurality of cell classes. When the respective cell does not include the predetermined genetic mutation(s), the cell is deemed to belong in a class in the plurality of cell classes other than the first class. The predetermined genetic mutation can be a single nucleotide polymorphism, an insertion, a deletion, or an inversion.

In some embodiments, the marker is a threshold number of genetic mutations mapping to one or more predetermined portions of the reference genome, and the segregating (at block 408 in FIG. 2E) determines whether the respective cell includes the threshold number of genetic mutations. The respective cell is deemed to belong to a first class in the plurality of cell classes or to a class in the plurality of cell classes other than the first class, based on whether or not the respective cell includes the threshold number of genetic mutations. The threshold number of genetic mutations can be selected in any suitable ways, and it can be preselected or selected dynamically, during the performance of the method. In some embodiments, the threshold number is determined by evaluating an average number and standard deviation of the average number of mutations in the one or more predetermined portions of the reference genome across the first plurality of cells.

The one or more predetermined portions of the reference genome can be any portion(s) of the genome. In some embodiments, for example, the one or more portions include the XRCC2 gene, the XRCC) gene, the RAD54 gene, the RAD54L gene, the H2AX gene, the phosphatase and tensin homolog gene, the ATM gene, and/or any other type of a gene.

In some embodiments, the first plurality of cells obtained, e.g., at block 404 of FIG. 2E, belong to an unperturbed clonal population, meaning that the first plurality of cells was not exposed to any compound that can affect cell's mitotic status. The unperturbed (first) plurality of cells can be compared to a perturbed (second) clonal population from the same species but that has been exposed to a compound. The compound can be, e.g., one or more of a DNA repair inhibitor, an organic compound (e.g., a compound that satisfies at least three criteria of the Lipinski rule of five criteria), or any other compound. In this way, the compound can be evaluated.

Accordingly, in some embodiments, the method of deconvolving the heterogeneous population of cells, illustrated in FIG. 2E, further comprises obtaining a set of nucleic acid sequence reads from each cell in a second plurality of cells of the species through a single cell sequencing process, thereby obtaining a second plurality of sets of nucleic acid sequence reads. Each respective set of nucleic acid sequence reads in the second plurality of sets of nucleic acid sequence reads is from a single cell in the second plurality of cells and the second plurality of cells has been exposed to a compound.

The method further comprises mapping a nucleic acid sequence of each respective sequence read in each respective set of sequence reads in the second plurality of sets of nucleic acid sequence reads onto a corresponding bin in the plurality of bins, and independently segregating each cell in the second plurality of cells into one of the plurality of cell classes based on the presence, absence, or amount of the marker or the marker set in the respective cell. Each cell in each respective cell class in the plurality of cell classes for the second plurality of cell is assigned into one of the plurality of groups based upon a pattern of sequence read counts of the respective cell across the plurality of bins by applying the first mitotic filter to the nucleic acid read count of respective bins in the plurality of bins obtained for the respective cell. A proportion of cells in each cell class in the plurality of cell classes that are in the first mitotic stage is then compared between the first plurality of cells and the second plurality of cells.

One or both of the first and second plurality of cells can be from a tumor biopsy. Thus, the response of the cells in the tumor biopsy to the compound can be evaluated by comparing the cells that were not treated with the compound and the treated cells.

In some embodiments, nucleic acid sequence reads are obtained from each cell in a plurality of cells through a single cell sequencing process. Any single cell sequencing technology can be employed in the present disclosure, and non-limiting examples of such technology are described herein below.

In some embodiments, the disclosure provides methods for diagnosing a disease state, e.g., a cancer state, of a subject based on the mitotic profile of a clonal population of cells, as determined using single cell sequencing. For instance, in some embodiments, a clonal population of cells is obtained from the subject, e.g., in the form of a tumor biopsy, and the mitotic stage of each cells in the clonal population is determined using single cell sequencing. The aggregate of each mitotic stage determined the cells in the clonal population provides a mitotic profile for the clonal population, as determined by the distribution of mitotic states in the various cells of the clonal population. Biological characteristics of the clonal population can then be determined based on the mitotic profile, e.g., by comparing the mitotic profile of the clonal population to known or theorized mitotic profiles for clonal populations with various biological states. In this fashion, for example, a benign tumor can be differentiated from a malignant tumor, a likelihood of a tumor metastasizing can be determined, a type of cancer can be identified, a stage of cancer can be determined, a predicted response to therapy can be determined, etc.

In some embodiments, treatment decisions and/or therapeutic administration is directed based on the disease state and/or biological characteristics identified for the clonal population using the mitotic profile. In this fashion, in some embodiments, the methods provided herein allow for precision therapy, e.g., precision oncology, by matching an appropriate type of therapy for a particular disease state, e.g., cancer state, as determined through elucidation of the mitotic profile for a clonal population of cells from the subject.

Accordingly, FIG. 2F illustrates a method 500 of deconvolving (504) a mitotic profile for a first clonal population comprising a first plurality of cells from a first biological sample, e.g., a tumor biopsy, from a subject. In some embodiments, all or a portion of method 500 is performed at a computer system 100 having one or more processors 102 and memory 104 storing one or more programs for execution by the one or more processors. The one or more programs comprising instructions for performing all or a portion of the following method.

In some embodiments, method 500 includes a step of sequencing 502 nucleic acids from a first plurality of cells in a first clonal population, by single cell sequencing, thereby generating a set of nucleic acid sequence reads from each cell in the first plurality of cells of the first clonal population. In some embodiments, the single cell sequencing process is a single cell DNA sequencing process and each nucleic acid sequence read in each set in the plurality of sets of nucleic acid sequence reads is a DNA sequence. However, in some embodiments, method 500 begins after the set of nucleic acid sequence reads has already been generated, e.g., a device connected with method 500 receives single cell sequencing results, e.g., over a local or distributed communications network, and the method proceeds by analyzing the results of the sequencing reaction to determine a mitotic profile for the clonal population, as described in the steps below.

Method 500 includes obtaining (506) a set of nucleic acid sequence reads from each cell in the first plurality of cells of the first clonal population through a single cell sequencing process. In this way, a first plurality of sets of nucleic acid sequence reads is obtained, where each respective set of nucleic acid sequence reads in the first plurality of sets of nucleic acid sequence reads is from a single cell in the first plurality of cells. In some embodiments, nucleic acid sequence reads are obtained from each cell in a plurality of cells through a single cell sequencing process. Any single cell sequencing technology can be employed in the present disclosure, and non-limiting examples of such technology are described herein below.

Method 500 then includes mapping (508) a nucleic acid sequence of each respective sequence read in each respective set of sequence reads onto a corresponding bin 124 in a plurality of bins. Each respective bin in the plurality of bins represents a different portion of a reference genome of the species. In this way, a nucleic acid sequence read count is obtained for each respective bin in the plurality of bins for each respective cell in the first plurality of cells. In some embodiments, the species is human, each bin in the plurality of bins is the same size and the plurality of bins collectively encompass at least three percent of the entire human genome, and the plurality of bins consists of between one hundred and two thousand bins. In some embodiments, the plurality of bins collectively encompasses at least 4%, 5%, 6%, 7%, 8%, 9%, 10%, 15%, 20%, 25%, 30%, 40%, 50%, 60%, 70%, 80%, or 90% of the entire human genome.

In some embodiments, the mapping normalizes the nucleic acid sequence read counts for each respective bin in the plurality of bins for each respective cell in the first plurality of cells, the first mitotic filter is a first predetermined pattern of read counts across a first subset of the plurality of bins that has been previously associated with the first mitotic stage, and a respective cell in the first plurality of cells is assigned to the first group when the predetermined pattern of read counts across the first subset of the bins of the first mitotic filter is exhibited by the normalized nucleic acid sequence read counts for the respective cell across the first subset of the plurality of bins.

Method 500 then includes assigning (510) each cell in the first plurality of cells into one of a plurality of groups 126 based upon a pattern of sequence read counts of the respective cell across the plurality of bins. A pattern of sequence read counts determined for a cell across the plurality of bins can be used to assign that cell into one of a plurality of groups, as shown at block 510 of FIG. 2F. The plurality of groups can include any suitable number of groups representing a replication, non-replication, or otherwise characterized status of a cell. For example, in some embodiments, the plurality of groups encompass at least a first group in the plurality of groups that represents a first mitotic stage and a second group in the plurality of groups that represents a non-mitotic stage. In such embodiments, the assigning determines whether the respective cell is to be assigned to the first group by applying a first mitotic filter to the nucleic acid read count of respective bins in the plurality of bins obtained for the respective cell. In the techniques in accordance with the present disclosure, assigning the respective cell to the group (e.g., the first group) allows deconvolving the first clonal population. A mitotic status of the cell can thus be determined by assigning that cell to a group in a plurality of groups. FIG. 5, discussed above, illustrates assignment of cells to respective clonal populations. In this way, a mitotic profile, e.g., the aggregate of the individual assignments of cells to one of the plurality of groups, for the first clonal population is deconvolved. The first mitotic stage can be any stage of mitosis. For example, it can be an early mitotic stage, a middle mitotic stage, a late mitotic stage, or any other mitotic stage. In some cases, the mitotic stage can be characterized, for example, by a percentage of cells in a group/class that are undergoing mitosis. Also, the first mitotic stage can be a stage where no mitosis is detected.

In some embodiments, a third group in the plurality of groups represents a second mitotic stage, the assigning determines whether the respective cell is to be assigned to the third group by applying a second mitotic filter to the nucleic acid read count of respective bins in the plurality of bins obtained for the respective cell, the second mitotic filter is a second predetermined pattern of read counts across a second subset of the plurality of bins that has been previously associated with the second mitotic stage, and a respective cell in the first plurality of cells is assigned to the second group when the predetermined pattern of read counts across the subset of the bins of the second mitotic filter is exhibited by the normalized nucleic acid sequence read counts for the respective cell across the second subset of the plurality of bins.

In some embodiments, the cells are independently segregated into cell classes based on markers or absence of markers. In some embodiments, the marker or the marker set comprises a predetermined genetic mutation, and the segregating determines whether the respective cell includes one or more predetermined genetic mutations. When the respective cell includes the predetermined genetic mutation(s), the cell is deemed to belong to a first class in the plurality of cell classes. When the respective cell does not include the predetermined genetic mutation(s), the cell is deemed to belong in a class in the plurality of cell classes other than the first class. The predetermined genetic mutation can be a single nucleotide polymorphism, an insertion, a deletion, or an inversion.

Method 500 then includes determining (512) whether the deconvolved mitotic profile for the first clonal population resembles a mitotic profile associated with a first disease state, e.g., cancer state, or a mitotic state associated with a second disease state, e.g., cancer state. In some embodiments, determining whether the mitotic profile resembles any particular profile associated with a disease state, e.g., a cancer state, includes comparing metrics associated with the mitotic profile to metrics for one or more profiles associated with one or more cancer states, and determining whether the metrics for the mitotic profile for the subject are sufficiently similar to any particular reference mitotic profile, e.g., whether a measure of similarity between the metrics for the mitotic profile for the subject and the metrics for the reference mitotic profile satisfies a threshold level of similarity. In some embodiments, determining whether the mitotic profile resembles any particular profile associated with a cancer state includes comparing metrics associated with the mitotic profile to metrics for a plurality of reference mitotic profiles, and determining which of the reference mitotic profiles is most similar to the mitotic profile for the subject. Non-limiting examples of metrics that can be used to make these comparisons include percentages of cells in a particular group, ratios of the percentage of cells in two or more particular groups, and other metrics associated with the distribution of cell types identified in the patient sample.

In some embodiments, determining whether the mitotic profile resembles any particular profile associated with a cancer state includes inputting one or more characteristics of the mitotic profile for the subject into an algorithm, e.g., a learning algorithm, trained to distinguish between different mitotic profiles associated with different cancer states. Non-limited examples of classification algorithms useful for this purpose include a neural network algorithm, a support vector machine algorithm, a Naive Bayes algorithm, a nearest neighbor algorithm, a boosted trees algorithm, a random forest algorithm, a convolutional neural network algorithm, a decision tree algorithm, a regression algorithm, and a clustering algorithm. Generally, the classifier algorithm is trained based on a training set that includes mitotic profiles of clonal cell populations from a plurality of test subjects whose disease state, e.g., cancer state, is known. In this fashion, the mitotic profiles are used as independent variables and the known disease states are used as dependent variables, for training the classification algorithm according to known methods.

In some embodiments, the methods described herein differentiate between the presence of a disease, e.g., cancer, and the absence of the disease. That is, for example, the first disease state is the presence of a disease and the second disease state is the absence of a disease state. In some embodiments, the method described herein differentiate between different types of a disease, e.g., different types of cancer. That is, for example, the first disease state is a first type of cancer and the second disease state is a second type of cancer. In some embodiments, the methods described herein differentiate between stages of a disease, e.g., cancer. That is, for example, the first disease state is a first stage of cancer (e.g., stage 0, 1, 2, 3, or 4) and the second disease state is a second stage of cancer. In some embodiments, the methods described herein differentiate between different prognoses for a disease, e.g., cancer. That is, for example, in some embodiments, the disease state is a cancerous state with a first prognosis (e.g., a first estimated survival rate, a first estimated disease-free survival rate, a first estimated recurrence rate, a first predicted response to a therapy, etc.) and the second disease state is a cancerous state with a second prognosis. Accordingly, in one embodiment, the first cancer state is a first type of cancer, and the second cancer state is a second type of cancer. Similarly, in some embodiments, the first cancer state is a first prognosis for cancer in the subject, and the second cancer state is a second prognosis for cancer in the subject In some embodiments, method 500 also includes a step of assigning therapy and/or administering therapy to the subject, based on the classification of the disease state in determining step 512. In this fashion, the subject is treated in a manner that is specific to their individual biology, e.g., the particular state of their disease. Accordingly, in some embodiments, method 500 includes, when the deconvolved mitotic profile for the first clonal population resembles a mitotic profile associated with a first disease state, e.g., cancer state, administering (514) a therapy for treatment of the first cancer state to the subject, and when the deconvolved mitotic profile for the first clonal population resembles a mitotic profile associated with a second disease state, e.g., cancer state, administering (516) a second therapy for treatment of the second cancer state to the subject. For example, in one embodiment where the mitotic profile of a clonal population of a tumor sample is used to classify the disease state of the subject, a first disease state is a classification that the tumor is benign and a second disease state is a classification that the tumor is malignant. Accordingly, in some embodiments, a tumor classified as benign may be treated by surgical removal without associated chemotherapy or not treated at all, while a tumor classified as malignant may be treated with a chemotherapeutic agent, e.g., instead of or in combination with surgical removal. Thus, in one embodiment, the first cancer state is a malignant state for the tumor, the first therapy for treatment of the first cancer state is a chemotherapeutic agent, the second cancer state is a benign state for the tumor, and the second therapy for treatment of the second cancer state is a therapy other than a chemotherapeutic agent.

In some embodiments, the first plurality of cells from the first clonal population belong to an unperturbed clonal population, meaning that the first plurality of cells was not exposed to any compound that can affect cell's mitotic status. The unperturbed (first) plurality of cells can be compared to a perturbed (second) clonal population from the same species but that has been exposed to a compound. The compound can be, e.g., one or more of a DNA repair inhibitor, an organic compound (e.g., a compound that satisfies at least three criteria of the Lipinski rule of five criteria), or any other compound. In this way, the compound can be evaluated.

Accordingly, in some embodiments, the method of deconvolving the heterogeneous population of cells, illustrated in FIG. 2F, further comprises obtaining a set of nucleic acid sequence reads from each cell in a second plurality of cells of the species through a single cell sequencing process, thereby obtaining a second plurality of sets of nucleic acid sequence reads. Each respective set of nucleic acid sequence reads in the second plurality of sets of nucleic acid sequence reads is from a single cell in the second plurality of cells and the second plurality of cells has been exposed to a compound. The method further comprises mapping a nucleic acid sequence of each respective sequence read in each respective set of sequence reads in the second plurality of sets of nucleic acid sequence reads onto a corresponding bin in the plurality of bins, and independently segregating each cell in the second plurality of cells into one of the plurality of cell classes based on the presence, absence, or amount of the marker or the marker set in the respective cell. Each cell in each respective cell class in the plurality of cell classes for the second plurality of cell is assigned into one of the plurality of groups based upon a pattern of sequence read counts of the respective cell across the plurality of bins by applying the first mitotic filter to the nucleic acid read count of respective bins in the plurality of bins obtained for the respective cell. A proportion of cells in each cell class in the plurality of cell classes that are in the first mitotic stage is then compared between the first plurality of cells and the second plurality of cells.

In some embodiments, the compound is an organic compound having a molecular weight of less than 2000 Daltons. In some embodiments, the compound is an organic compound that satisfies the Lipinski rule of five criteria. In some embodiments, the compound is an organic compound that satisfies at least three criteria of the Lipinski rule of five criteria. In some embodiments, the compound is a checkpoint blockade immunotherapy. In some embodiments, the checkpoint blockade immunotherapy is an anti-CTLA-4, anti-PD1, anti-PD-L1, anti-LAG3, anti-TIM-3, anti-GITR, anti-OX40, anti-CD40, anti-TIGIT, anti4-1BB, anti-B7-H3, anti-B7-H4, or anti-BTLA compound.

One or both of the first and second plurality of cells can be from a tumor biopsy. Thus, the response of the cells in the tumor biopsy to the compound can be evaluated by comparing the cells that were not treated with the compound and the treated cells.

In some embodiments, the disclosure provides methods for predicting whether a disease state, e.g., a cancer state, of a subject with respond to one or more therapeutic approaches, based on the mitotic profile of a clonal population of cells, as determined using single cell sequencing. For instance, in some embodiments, a clonal population of cells is obtained from the subject, e.g., in the form of a tumor biopsy, and the mitotic stage of each cells in the clonal population is determined using single cell sequencing. The aggregate of each mitotic stage determined the cells in the clonal population provides a mitotic profile for the clonal population, as determined by the distribution of mitotic states in the various cells of the clonal population. A prediction of whether the clonal population will respond favorably to a given therapeutic approach can then be determined based on the mitotic profile, e.g., by comparing the mitotic profile of the clonal population to known or theorized mitotic profiles for clonal populations whose response to one or more therapeutic approach is known. In this fashion, for example, it can be determined whether a cancer in a subject will be sensitive to a particular chemotherapy drug and/or therapeutic regime.

In some embodiments, treatment decisions and/or therapeutic administration is directed based on the disease state and/or biological characteristics identified for the clonal population using the mitotic profile. In this fashion, in some embodiments, the methods provided herein allow for precision therapy, e.g., precision oncology, by matching an appropriate type of therapy for a particular disease state, e.g., cancer state, as determined through elucidation of the mitotic profile for a clonal population of cells from the subject.

Accordingly, FIG. 2G illustrates a method 600 of deconvolving (604) a mitotic profile for a first clonal population comprising a first plurality of cells from a first biological sample, e.g., a tumor biopsy, from a subject. In some embodiments, all or a portion of method 600 is performed at a computer system 100 having one or more processors 102 and memory 104 storing one or more programs for execution by the one or more processors. The one or more programs comprising instructions for performing all or a portion of the following method.

In some embodiments, method 600 includes a step of sequencing 602 nucleic acids from a first plurality of cells in a first clonal population, by single cell sequencing, thereby generating a set of nucleic acid sequence reads from each cell in the first plurality of cells of the first clonal population. In some embodiments, the single cell sequencing process is a single cell DNA sequencing process and each nucleic acid sequence read in each set in the plurality of sets of nucleic acid sequence reads is a DNA sequence. However, in some embodiments, method 600 begins after the set of nucleic acid sequence reads has already been generated, e.g., a device connected with method 600 receives single cell sequencing results, e.g., over a local or distributed communications network, and the method proceeds by analyzing the results of the sequencing reaction to determine a mitotic profile for the clonal population, as described in the steps below.

Method 600 includes obtaining (606) a set of nucleic acid sequence reads from each cell in the first plurality of cells of the first clonal population through a single cell sequencing process. In this way, a first plurality of sets of nucleic acid sequence reads is obtained, where each respective set of nucleic acid sequence reads in the first plurality of sets of nucleic acid sequence reads is from a single cell in the first plurality of cells. In some embodiments, nucleic acid sequence reads are obtained from each cell in a plurality of cells through a single cell sequencing process. Any single cell sequencing technology can be employed in the present disclosure, and non-limiting examples of such technology are described herein below.

Method 600 then includes mapping (608) a nucleic acid sequence of each respective sequence read in each respective set of sequence reads onto a corresponding bin 124 in a plurality of bins. Each respective bin in the plurality of bins represents a different portion of a reference genome of the species. In this way, a nucleic acid sequence read count is obtained for each respective bin in the plurality of bins for each respective cell in the first plurality of cells. In some embodiments, the species is human, each bin in the plurality of bins is the same size and the plurality of bins collectively encompass at least three percent of the entire human genome, and the plurality of bins consists of between one hundred and two thousand bins. In some embodiments, the plurality of bins collectively encompasses at least 4%, 5%, 6%, 7%, 8%, 9%, 10%, 15%, 20%, 25%, 30%, 40%, 50%, 60%, 70%, 80%, or 90% of the entire human genome.

In some embodiments, the mapping normalizes the nucleic acid sequence read counts for each respective bin in the plurality of bins for each respective cell in the first plurality of cells, the first mitotic filter is a first predetermined pattern of read counts across a first subset of the plurality of bins that has been previously associated with the first mitotic stage, and a respective cell in the first plurality of cells is assigned to the first group when the predetermined pattern of read counts across the first subset of the bins of the first mitotic filter is exhibited by the normalized nucleic acid sequence read counts for the respective cell across the first subset of the plurality of bins.

Method 600 then includes assigning (610) each cell in the first plurality of cells into one of a plurality of groups 126 based upon a pattern of sequence read counts of the respective cell across the plurality of bins. A pattern of sequence read counts determined for a cell across the plurality of bins can be used to assign that cell into one of a plurality of groups, as shown at block 610 of FIG. 2G. The plurality of groups can include any suitable number of groups representing a replication, non-replication, or otherwise characterized status of a cell. For example, in some embodiments, the plurality of groups encompass at least a first group in the plurality of groups that represents a first mitotic stage and a second group in the plurality of groups that represents a non-mitotic stage. In such embodiments, the assigning determines whether the respective cell is to be assigned to the first group by applying a first mitotic filter to the nucleic acid read count of respective bins in the plurality of bins obtained for the respective cell. In the techniques in accordance with the present disclosure, assigning the respective cell to the group (e.g., the first group) allows deconvolving the first clonal population. A mitotic status of the cell can thus be determined by assigning that cell to a group in a plurality of groups. FIG. 5, discussed above, illustrates assignment of cells to respective clonal populations. In this way, a mitotic profile, e.g., the aggregate of the individual assignments of cells to one of the plurality of groups, for the first clonal population is deconvolved. The first mitotic stage can be any stage of mitosis. For example, it can be an early mitotic stage, a middle mitotic stage, a late mitotic stage, or any other mitotic stage. In some cases, the mitotic stage can be characterized, for example, by a percentage of cells in a group/class that are undergoing mitosis. Also, the first mitotic stage can be a stage where no mitosis is detected.

In some embodiments, a third group in the plurality of groups represents a second mitotic stage, the assigning determines whether the respective cell is to be assigned to the third group by applying a second mitotic filter to the nucleic acid read count of respective bins in the plurality of bins obtained for the respective cell, the second mitotic filter is a second predetermined pattern of read counts across a second subset of the plurality of bins that has been previously associated with the second mitotic stage, and a respective cell in the first plurality of cells is assigned to the second group when the predetermined pattern of read counts across the subset of the bins of the second mitotic filter is exhibited by the normalized nucleic acid sequence read counts for the respective cell across the second subset of the plurality of bins.

In some embodiments, the cells are independently segregated into cell classes based on markers or absence of markers. In some embodiments, the marker or the marker set comprises a predetermined genetic mutation, and the segregating determines whether the respective cell includes one or more predetermined genetic mutations. When the respective cell includes the predetermined genetic mutation(s), the cell is deemed to belong to a first class in the plurality of cell classes. When the respective cell does not include the predetermined genetic mutation(s), the cell is deemed to belong in a class in the plurality of cell classes other than the first class. The predetermined genetic mutation can be a single nucleotide polymorphism, an insertion, a deletion, or an inversion.

Method 600 then includes determining (612) whether the deconvolved mitotic profile for the first clonal population resembles a mitotic profile for a population of cells, e.g., cancerous cells, that are sensitive to a first type of therapy, e.g., to a particular class of chemotherapeutic agent, to a particular chemotherapeutic agent, to a particular combination of chemotherapeutic agents, or a particular treatment regime, etc. In some embodiments, determining whether the mitotic profile resembles any particular profile associated with a therapeutic sensitivity includes comparing metrics associated with the mitotic profile to metrics for one or more profiles associated with one or more therapeutic sensitivities, and determining whether the metrics for the mitotic profile for the subject are sufficiently similar to any particular reference mitotic profile, e.g., whether a measure of similarity between the metrics for the mitotic profile for the subject and the metrics for the reference mitotic profile satisfies a threshold level of similarity. In some embodiments, determining whether the mitotic profile resembles any particular profile associated with a therapeutic sensitivity includes comparing metrics associated with the mitotic profile to metrics for a plurality of reference mitotic profiles, and determining which of the reference mitotic profiles is most similar to the mitotic profile for the subject. Non-limiting examples of metrics that can be used to make these comparisons include percentages of cells in a particular group, ratios of the percentage of cells in two or more particular groups, and other metrics associated with the distribution of cell types identified in the patient sample.

In some embodiments, determining whether the mitotic profile resembles any particular profile associated with a therapeutic sensitivity includes inputting one or more characteristics of the mitotic profile for the subject into an algorithm, e.g., a learning algorithm, trained to distinguish between different therapeutic sensitivities. Non-limited examples of classification algorithms useful for this purpose include a neural network algorithm, a support vector machine algorithm, a Naive Bayes algorithm, a nearest neighbor algorithm, a boosted trees algorithm, a random forest algorithm, a convolutional neural network algorithm, a decision tree algorithm, a regression algorithm, and a clustering algorithm. Generally, the classifier algorithm is trained based on a training set that includes mitotic profiles of clonal cell populations from a plurality of test subjects whose therapeutic sensitivity is known. In this fashion, the mitotic profiles are used as independent variables and the known therapeutic sensitivities are used as dependent variables, for training the classification algorithm according to known methods.

In some embodiments, method 600 also includes a step of assigning therapy and/or administering therapy to the subject, based on the classification of the therapeutic sensitivity in determining step 612. In this fashion, the subject is treated in a manner that is specific to their individual biology, e.g., the particular sensitivity of their disease, e.g., their particular cancer, to one or more therapeutics. Accordingly, in some embodiments, method 600 includes, when the deconvolved mitotic profile for the first clonal population resembles a mitotic profile for a population of cancerous cells that are sensitive to a first type of therapy, administering (614) the first type of therapy to the subject, and when the deconvolved mitotic profile for the first clonal population does not resemble a mitotic profile for a population of cancerous cells that are sensitive to a first type of therapy, administering (616) a second type of therapy to the subject.

For example, in one embodiment, the first type of therapy is a DNA repair inhibitor chemotherapeutic agent, the second type of therapy is a chemotherapeutic agent other than a DNA repair inhibitor, and the mitotic profile for a population of cancerous cells that are sensitive to the first type of therapy indicates a homologous recombination repair deficiency. In some embodiments, the DNA repair inhibitor chemotherapeutic inhibitor is a PARP inhibitor.

In some embodiments, the first plurality of cells from the first clonal population belong to an unperturbed clonal population, meaning that the first plurality of cells was not exposed to any compound that can affect cell's mitotic status. The unperturbed (first) plurality of cells can be compared to a perturbed (second) clonal population from the same species but that has been exposed to a compound. The compound can be, e.g., one or more of a DNA repair inhibitor, an organic compound (e.g., a compound that satisfies at least three criteria of the Lipinski rule of five criteria), or any other compound. In this way, the compound can be evaluated.

Accordingly, in some embodiments, the method of deconvolving the heterogeneous population of cells, illustrated in FIG. 2G, further comprises obtaining a set of nucleic acid sequence reads from each cell in a second plurality of cells of the species through a single cell sequencing process, thereby obtaining a second plurality of sets of nucleic acid sequence reads. Each respective set of nucleic acid sequence reads in the second plurality of sets of nucleic acid sequence reads is from a single cell in the second plurality of cells and the second plurality of cells has been exposed to a compound. The method further comprises mapping a nucleic acid sequence of each respective sequence read in each respective set of sequence reads in the second plurality of sets of nucleic acid sequence reads onto a corresponding bin in the plurality of bins, and independently segregating each cell in the second plurality of cells into one of the plurality of cell classes based on the presence, absence, or amount of the marker or the marker set in the respective cell. Each cell in each respective cell class in the plurality of cell classes for the second plurality of cell is assigned into one of the plurality of groups based upon a pattern of sequence read counts of the respective cell across the plurality of bins by applying the first mitotic filter to the nucleic acid read count of respective bins in the plurality of bins obtained for the respective cell. A proportion of cells in each cell class in the plurality of cell classes that are in the first mitotic stage is then compared between the first plurality of cells and the second plurality of cells.

In some embodiments, the compound is an organic compound having a molecular weight of less than 2000 Daltons. In some embodiments, the compound is an organic compound that satisfies the Lipinski rule of five criteria. In some embodiments, the compound is an organic compound that satisfies at least three criteria of the Lipinski rule of five criteria. In some embodiments, the compound is a checkpoint blockade immunotherapy. In some embodiments, the checkpoint blockade immunotherapy is an anti-CTLA-4, anti-PD1, anti-PD-L1, anti-LAG3, anti-TIM-3, anti-GITR, anti-OX40, anti-CD40, anti-TIGIT, anti4-1BB, anti-B7-H3, anti-B7-H4, or anti-BTLA compound.

One or both of the first and second plurality of cells can be from a tumor biopsy. Thus, the response of the cells in the tumor biopsy to the compound can be evaluated by comparing the cells that were not treated with the compound and the treated cells.

In some embodiments, the disclosure provides methods for monitoring the efficacy of therapy for a disease state, e.g., a cancer state, of a subject, based on the mitotic profile of a clonal population of cells, as determined using single cell sequencing. For instance, in some embodiments, a first clonal population of cells is obtained from the subject, e.g., in the form of a tumor biopsy, prior to beginning a therapy or at a first time point during therapy, and the mitotic stage of each cells in the clonal population is determined using single cell sequencing. A second clonal population of cells is then obtained from the subject, e.g., in the form of a tumor biopsy, after therapy has begun or at a second time point (after the first time point) during therapy, and the mitotic stage of each cells in the clonal population is determined using single cell sequencing. The aggregate of each mitotic stage determined the cells in each of the clonal population provides a mitotic profile for the clonal population, as determined by the distribution of mitotic states in the various cells of the clonal population. The two mitotic profiles are then compared, to evaluate the efficacy of the therapy, e.g., by determining whether a change in the mitotic profile of the clonal population consistent with efficacious therapy has occurred. In this fashion, for example, it can be determined whether a particular therapy is working for a subject, and thus should be continued, or not working, and thus should be changed.

In some embodiments, treatment decisions and/or therapeutic administration is directed based on the characteristics of the mitotic profile identified for the clonal population using the mitotic profile over time. In this fashion, in some embodiments, the methods provided herein allow for precision therapy, e.g., precision oncology, by matching an appropriate type of therapy for a particular disease state, e.g., cancer state, as determined through elucidation of the mitotic profile for a clonal population of cells from the subject.

Accordingly, FIG. 2H illustrates a method 700 of deconvolving (704) a mitotic profile for a first clonal population comprising a first plurality of cells from a first biological sample, e.g., a tumor biopsy, from a subject being treated for a disease state, e.g., cancer, with a first type of therapy. In some embodiments, all or a portion of method 700 is performed at a computer system 100 having one or more processors 102 and memory 104 storing one or more programs for execution by the one or more processors. The one or more programs comprising instructions for performing all or a portion of the following method.

In some embodiments, method 700 includes a step of sequencing 702 nucleic acids from a first plurality of cells in a first clonal population, by single cell sequencing, thereby generating a set of nucleic acid sequence reads from each cell in the first plurality of cells of the first clonal population. In some embodiments, the single cell sequencing process is a single cell DNA sequencing process and each nucleic acid sequence read in each set in the plurality of sets of nucleic acid sequence reads is a DNA sequence. However, in some embodiments, method 700 begins after the set of nucleic acid sequence reads has already been generated, e.g., a device connected with method 700 receives single cell sequencing results, e.g., over a local or distributed communications network, and the method proceeds by analyzing the results of the sequencing reaction to determine a mitotic profile for the clonal population, as described in the steps below.

Method 700 includes obtaining (706) a set of nucleic acid sequence reads from each cell in the first plurality of cells of the first clonal population through a single cell sequencing process. In this way, a first plurality of sets of nucleic acid sequence reads is obtained, where each respective set of nucleic acid sequence reads in the first plurality of sets of nucleic acid sequence reads is from a single cell in the first plurality of cells. In some embodiments, nucleic acid sequence reads are obtained from each cell in a plurality of cells through a single cell sequencing process. Any single cell sequencing technology can be employed in the present disclosure, and non-limiting examples of such technology are described herein below.

Method 700 then includes mapping (708) a nucleic acid sequence of each respective sequence read in each respective set of sequence reads onto a corresponding bin 124 in a plurality of bins. Each respective bin in the plurality of bins represents a different portion of a reference genome of the species. In this way, a nucleic acid sequence read count is obtained for each respective bin in the plurality of bins for each respective cell in the first plurality of cells. In some embodiments, the species is human, each bin in the plurality of bins is the same size and the plurality of bins collectively encompass at least three percent of the entire human genome, and the plurality of bins consists of between one hundred and two thousand bins. In some embodiments, the plurality of bins collectively encompasses at least 4%, 5%, 6%, 7%, 8%, 9%, 10%, 15%, 20%, 25%, 30%, 40%, 50%, 60%, 70%, 80%, or 90% of the entire human genome.

In some embodiments, the mapping normalizes the nucleic acid sequence read counts for each respective bin in the plurality of bins for each respective cell in the first plurality of cells, the first mitotic filter is a first predetermined pattern of read counts across a first subset of the plurality of bins that has been previously associated with the first mitotic stage, and a respective cell in the first plurality of cells is assigned to the first group when the predetermined pattern of read counts across the first subset of the bins of the first mitotic filter is exhibited by the normalized nucleic acid sequence read counts for the respective cell across the first subset of the plurality of bins.

Method 700 then includes assigning (710) each cell in the first plurality of cells into one of a plurality of groups 126 based upon a pattern of sequence read counts of the respective cell across the plurality of bins. A pattern of sequence read counts determined for a cell across the plurality of bins can be used to assign that cell into one of a plurality of groups, as shown at block 710 of FIG. 2H. The plurality of groups can include any suitable number of groups representing a replication, non-replication, or otherwise characterized status of a cell. For example, in some embodiments, the plurality of groups encompass at least a first group in the plurality of groups that represents a first mitotic stage and a second group in the plurality of groups that represents a non-mitotic stage. In such embodiments, the assigning determines whether the respective cell is to be assigned to the first group by applying a first mitotic filter to the nucleic acid read count of respective bins in the plurality of bins obtained for the respective cell. In the techniques in accordance with the present disclosure, assigning the respective cell to the group (e.g., the first group) allows deconvolving the first clonal population. A mitotic status of the cell can thus be determined by assigning that cell to a group in a plurality of groups. FIG. 5, discussed above, illustrates assignment of cells to respective clonal populations. In this way, a mitotic profile, e.g., the aggregate of the individual assignments of cells to one of the plurality of groups, for the first clonal population is deconvolved. The first mitotic stage can be any stage of mitosis. For example, it can be an early mitotic stage, a middle mitotic stage, a late mitotic stage, or any other mitotic stage. In some cases, the mitotic stage can be characterized, for example, by a percentage of cells in a group/class that are undergoing mitosis. Also, the first mitotic stage can be a stage where no mitosis is detected.

In some embodiments, a third group in the plurality of groups represents a second mitotic stage, the assigning determines whether the respective cell is to be assigned to the third group by applying a second mitotic filter to the nucleic acid read count of respective bins in the plurality of bins obtained for the respective cell, the second mitotic filter is a second predetermined pattern of read counts across a second subset of the plurality of bins that has been previously associated with the second mitotic stage, and a respective cell in the first plurality of cells is assigned to the second group when the predetermined pattern of read counts across the subset of the bins of the second mitotic filter is exhibited by the normalized nucleic acid sequence read counts for the respective cell across the second subset of the plurality of bins.

In some embodiments, the cells are independently segregated into cell classes based on markers or absence of markers. In some embodiments, the marker or the marker set comprises a predetermined genetic mutation, and the segregating determines whether the respective cell includes one or more predetermined genetic mutations. When the respective cell includes the predetermined genetic mutation(s), the cell is deemed to belong to a first class in the plurality of cell classes. When the respective cell does not include the predetermined genetic mutation(s), the cell is deemed to belong in a class in the plurality of cell classes other than the first class. The predetermined genetic mutation can be a single nucleotide polymorphism, an insertion, a deletion, or an inversion.

Method 700 then includes comparing (712) the deconvolved mitotic profile for the first clonal population to a deconvolved mitotic profile for a second clonal population comprising a second plurality of cells from a second biological sample, e.g., tumor biopsy, obtained from the subject prior to being treated for the disease state, e.g., cancer, or at an earlier point during the therapy, with the first type of therapy. In some embodiments, the comparison is between metrics associated with the mitotic profiles and determines whether the metrics for the first mitotic profile for the subject are sufficiently different to the metrics for the second mitotic profile for the subject, whether a measure of dissimilarity between the metrics satisfies a threshold level of dissimilarity. Non-limiting examples of metrics that can be used to make these comparisons include percentages of cells in a particular group, ratios of the percentage of cells in two or more particular groups, and other metrics associated with the distribution of cell types identified in the patient sample.

In some embodiments, determining whether the mitotic profile indicates that the first type of therapy is producing at least a threshold level of therapeutic efficacy includes inputting one or more characteristics of the first and/or second mitotic profile for the subject, and/or one or more metrics associated with a change in the mitotic profile over time, into an algorithm, e.g., a learning algorithm, trained to distinguish between levels of therapeutic efficacy. Non-limited examples of classification algorithms useful for this purpose include a neural network algorithm, a support vector machine algorithm, a Naive Bayes algorithm, a nearest neighbor algorithm, a boosted trees algorithm, a random forest algorithm, a convolutional neural network algorithm, a decision tree algorithm, a regression algorithm, and a clustering algorithm. Generally, the classifier algorithm is trained based on a training set that includes first and/or second mitotic profiles, or changes between first and second mitotic profiles over time, of clonal cell populations from a plurality of test subjects whose response to a therapy is known. In this fashion, the mitotic profiles, or differences thereof, are used as independent variables and the known therapeutic responses are used as dependent variables, for training the classification algorithm according to known methods.

In some embodiments, method 700 also includes a step of assigning therapy and/or administering therapy to the subject, based on the determination of the efficacy of the first therapy in step 712. In this fashion, the subject is treated in a manner that is specific to their individual biology, e.g., which may or may not be responding adequately to the first type of therapy. As such, adjustments or changes to the patient's therapy can be made to provide better therapeutic efficacy. Accordingly, in some embodiments, method 700 includes, when a change in the deconvolved mitotic profile for the first clonal population, relative to the deconvolved mitotic profile for the second clonal population, indicates that the first type of therapy is not producing at least a threshold level of efficacy, administering (714) a second type of therapy to the subject (e.g., adjusting or changing the patient's therapy), and when a change in the deconvolved mitotic profile for the first clonal population, relative to the deconvolved mitotic profile for the second clonal population, indicates that the first type of therapy is producing at least a threshold level of efficacy, continue administering (716) the first type of therapy to the subject.

For example, in one embodiment, when the first type of therapy is a DNA repair inhibitor chemotherapeutic agent, the second type of therapy is a chemotherapeutic agent other than a DNA repair inhibitor, and a change in the deconvolved mitotic profile for the first clonal population, relative to the deconvolved mitotic profile for the second clonal population, indicates that the first type of therapy is not producing at least a threshold level of efficacy, changing the therapy for the subject from the first type of therapy to the second type of therapy, e.g., administer the second type of therapy to the subject, rather than the first type of therapy. In some embodiments, the DNA repair inhibitor chemotherapeutic inhibitor is a PARP inhibitor.

In some embodiments, the first plurality of cells from the first clonal population belong to an unperturbed clonal population, meaning that the first plurality of cells was not exposed to any compound that can affect cell's mitotic status. The unperturbed (first) plurality of cells can be compared to a perturbed (second) clonal population from the same species but that has been exposed to a compound. The compound can be, e.g., one or more of a DNA repair inhibitor, an organic compound (e.g., a compound that satisfies at least three criteria of the Lipinski rule of five criteria), or any other compound. In this way, the compound can be evaluated.

Accordingly, in some embodiments, the method of deconvolving the heterogeneous population of cells, illustrated in FIG. 2H, further comprises obtaining a set of nucleic acid sequence reads from each cell in a second plurality of cells of the species through a single cell sequencing process, thereby obtaining a second plurality of sets of nucleic acid sequence reads. Each respective set of nucleic acid sequence reads in the second plurality of sets of nucleic acid sequence reads is from a single cell in the second plurality of cells and the second plurality of cells has been exposed to a compound. The method further comprises mapping a nucleic acid sequence of each respective sequence read in each respective set of sequence reads in the second plurality of sets of nucleic acid sequence reads onto a corresponding bin in the plurality of bins, and independently segregating each cell in the second plurality of cells into one of the plurality of cell classes based on the presence, absence, or amount of the marker or the marker set in the respective cell. Each cell in each respective cell class in the plurality of cell classes for the second plurality of cell is assigned into one of the plurality of groups based upon a pattern of sequence read counts of the respective cell across the plurality of bins by applying the first mitotic filter to the nucleic acid read count of respective bins in the plurality of bins obtained for the respective cell. A proportion of cells in each cell class in the plurality of cell classes that are in the first mitotic stage is then compared between the first plurality of cells and the second plurality of cells.

In some embodiments, the compound is an organic compound having a molecular weight of less than 2000 Daltons. In some embodiments, the compound is an organic compound that satisfies the Lipinski rule of five criteria. In some embodiments, the compound is an organic compound that satisfies at least three criteria of the Lipinski rule of five criteria. In some embodiments, the compound is a checkpoint blockade immunotherapy. In some embodiments, the checkpoint blockade immunotherapy is an anti-CTLA-4, anti-PD1, anti-PD-L1, anti-LAG3, anti-TIM-3, anti-GITR, anti-OX40, anti-CD40, anti-TIGIT, anti4-1BB, anti-B7-H3, anti-B7-H4, or anti-BTLA compound.

One or both of the first and second plurality of cells can be from a tumor biopsy. Thus, the response of the cells in the tumor biopsy to the compound can be evaluated by comparing the cells that were not treated with the compound and the treated cells.

Single Cell Sequencing

In some embodiments the single cell sequencing process makes use of microfluidic partitions. A single cell is captured within each microfluidic droplet and then pools of single barcodes within each of those droplets are used to tag all of the contents (e.g., first entities 122) of a given cell. For example, in some embodiments, a pool of ~750,000 barcodes is sampled to separately index each cells' transcriptome by partitioning thousands of cells into nanoliter-scale Gel Bead-In-EMulsions (GEMs), where all generated cDNA share a common barcode. Libraries are generated and sequenced from the cDNA and the barcodes are used to associate individual reads back to the individual partitions. In other words, each respective droplet (GEM) is assigned its own barcode and all the nucleic acid contents in a respective droplet are tagged with the barcode unique to the respective droplet. In some embodiments, such droplets are formed as described in Zheng et al., 2016, Nat Biotchnol. 34(3): 303-311; or in the Chromium, Single Cell 3' Reagent Kits v2. User Guide, 2017, 10× Genomics, Pleasanton, Calif., Rev. B, page, 2, each of which is hereby incorporated by reference. In some alternative embodiments, equivalent 5' chemistry is used rather than the 3' chemistry disclosed in these references.

In some embodiments there are tens, hundreds, thousands, tens of thousands, or one hundreds of thousands of such microfluidic droplets. In some such embodiments, at least seventy percent, at least eighty percent, at least ninety percent, at least ninety percent, at least ninety-five percent, at least ninety-eight percent, or at least ninety-nine percent of the respective microfluidic droplets contain either no cell or a single cell while the remainder of the microfluidic droplets contain two or more cells. In other words, to achieve single cell resolution, the cells are delivered at a limiting dilution, such that the majority (~90-99%) of generated nanoliter-scale gel bead-in-emulsions (GEMs) contains no cell, while the remainder largely contain a single cell. See the Chromium, Single Cell 3' Reagent Kits v2. User Guide, 2017, 10× Genomics, Pleasanton, Calif., Rev. B, page, 2, which is hereby incorporated by reference. In some alternative embodiments, equivalent 5' chemistry is used rather than the 3' chemistry disclosed in this reference.

In some embodiments the single cell sequencing process is a single cell RNA sequencing process and each nucleic acid sequence read in each set in the plurality of sets of nucleic acid sequence reads is an RNA sequence. In some embodiments, each respective set of nucleic acid sequence reads collectively represents at least one percent of the genes of the cell corresponding to the respective set of nucleic acid sequence reads. In some such embodiments within an individual droplet, gel bead dissolution releases the amplification primer into the partitioned solution. In some embodiments, upon dissolution of the single cell 3' Gel Bead in a GEM, primers containing (i) an Illumina R1 sequence (read 1 sequencing primer), (ii) a 16 bp 10× Barcode, (iii) a 10 bp Unique Molecular Identifier (UMI) and (iv) a polydT primer sequence are released and mixed with cell lysate and Master Mix. Incubation of the GEMs then produces barcoded, full-length cDNA from poly-adenylated mRNA. After incubation, the GEMs are broken and the pooled fractions are recovered. See the Chromium, Single Cell 3' Reagent Kits v2. User Guide, 2017, 10× Genomics, Pleasanton, Calif., Rev. B, page, 2, which is hereby incorporated by reference. In some such embodiments, silane magnetic beads are used to remove leftover biochemical reagents and primers from the post GEM reaction mixture. Full-length, barcoded cDNA is then amplified by PCR to generate sufficient mass for library construction. In this way, the mRNA can be mapped to individual genes in the genome of a species and therefore they can be sequenced and, furthermore, the mRNA of a cell can be distinguished from the mRNA of another cell based on the unique barcoded. This contrasts to bulk sequencing techniques in which all the cells are pooled together and the measurement profile is that of the mRNA of the whole collection of the cells without the ability to distinguish the measurement signal of sequence reads by individual cells. An example of such measurement techniques is disclosed in United States Patent Application 2015/0376609, which is hereby incorporated by reference in its entirety. As such, in some embodiments, the sequence reads of each mRNA in a particular cell in the plurality of cells is barcoded with a first barcode that is unique to the particular cell. In some embodiments, the discrete attribute value of the sequence reads of each mRNA in a particular cell in the plurality of cells is determined after the particular cell has been separated from all the other cells in the plurality of cells into its own microfluidic partition. In the case where each sequence read is of an mRNA that maps to a particular gene, such embodiments provide the ability to explore the heterogeneity between cells, which is one form of pattern analysis afforded by the systems and method of the present disclosure. In some such embodiments, where mRNA abundance is being measured, it is possible that the mRNA abundance in the cell sample may vary vastly from cell to cell.

In some embodiments, this sequence information, in the form of sequence reads 1634, is obtained using a droplet based single-cell RNA-sequencing (scRNA-seq) microfluidics system that enables 3' or 5' messenger RNA (mRNA) digital counting of thousands of single second entities 126 (e.g., single cells). In such sequencing, droplet-based platform enables barcoding of cells.

In some embodiments, the scRNAseq microfluidics system builds on the GemCode technology, which has been used for genome haplotyping, structural variant analysis and de novo assembly of a human genome. See Zheng et al., 2016 "Haplotyping germline and cancer genomes with high-throughput linked-read sequencing," Nat. Biotechnol. 34, pp. 303-311; Narasimhan et al., 2016, "Health and population effects of rare gene knockouts in adult humans with related parents," Science 352, pp. 474-477 (2016); and Mostovoy et al., 2016, "A hybrid approach for de novo human genome sequence assembly and phasing," Nat. Methods 13, 587-590, each of which is incorporated by reference, for a general description of GemCode technology. Such sequencing uses a gel bead-in-emulsion (GEM).

GEM generation takes place in a multi-channel microfluidic chip that encapsulates single gel beads at a predetermined fill rates, such as approximately 80%. For the clonal datasets 1602 of the present disclosure, in some embodiments, a 5' gene expression protocol is followed rather than a 3' gene expression protocol. This provides full-length (5' UTR to constant region), paired T-cell receptor (TCR) transcripts or B-cell receptor (TCR) transcripts from a number of (e.g., 100-10,000) individual second entities 126 (e.g., lymphocytes) per sample. In some embodiments, as in the case of the 3' gene expression protocol described in Zheng et al., id., the 5' expression protocol includes partitioning the cells into GEMs. In particular, in some embodiments, single cell resolution is achieved by delivering the cells at a limiting dilution, such that the majority (~90-99%) of generated GEMs contains no single second entity 126 (e.g., lymphocyte), while the remainder largely contain a single second entity (e.g., lymphocyte). In some embodiments, upon dissolution of the single cell 5' gel bead in a GEM, oligonucleotides containing (i) a read 1 sequencing primer (e.g., ILLUMINA R1 sequence), (ii) a barcode 1630, (iii) a unique molecular identifier (UMI) 1632, and (iv) a switch oligonucleotide are released and mixed with cell lysate and a master mix that contains poly(dT) primers. Incubation of the GEMs then produces barcoded, full-length cDNA from poly-adenylated mRNA. After incubation, the GEMs are broken and the pooled fractions are recovered. In some embodiments, magnetic beads (e.g., silane beads) are used to remove leftover biochemical reagents and primers from the post GEM reaction mixture.

Discrete Attribute Value Pipeline.

As discussed above, in some embodiments, upon dissolution of the single cell 3' gel bead in a GEM, primers containing (i) an Illumina R1 sequence (read 1 sequencing primer), (ii) a 16 bp 10× Barcode, (iii) a 10 bp Unique Molecular Identifier (UMI) and (iv) a poly-dT primer sequence are released and mixed with cell lysate and Master Mix. Incubation of the GEMs then produces barcoded, full-length cDNA from poly-adenylated mRNA. After incubation, the GEMs are broken and the pooled fractions are recovered. Further, in some embodiments, silane magnetic beads are used to remove leftover biochemical reagents and primers from the post GEM reaction mixture. Full-length, barcoded cDNA is then amplified by PCR to generate sufficient mass for library construction. As discussed above, this amplified product is divided into aliquots at least one of which is subjected to the discrete attribute value pipeline.

In some embodiments, the discrete attribute value pipeline comprises enzymatic fragmentation and size selection in order to optimize the cDNA amplicon size prior to library construction. In some embodiments, R1 (read 1 primer sequence) are added to the molecules during GEM incubation. In some embodiments, P5, P7, a sample index and R2 (read 2 primer sequence) are added during library construction via End Repair, A-tailing, Adaptor Ligation and PCR. In some embodiments, the final libraries contain the P5 and P7 primers used in ILLUMINA bridge amplification. See the Chromium, Single Cell 3' Reagent Kits v2. User Guide, 2017, 10× Genomics, Pleasanton, Calif., Rev. B, page, 2, each of which is hereby incorporated by reference. Such a protocol produces ILLUMINA-ready sequencing libraries. In some embodiments, a single cell 3' library comprises standard ILLUMINA paired-end constructs which begin and end with P5 and P7. In some embodiments, the single cell 3' 16 bp 10×™ Barcode and 10 bp UMI are encoded in Read 1, while Read 2 is used to sequence the cDNA fragment. Sample index sequences are incorporated as the i7 index read. Read 1 and Read 2 are standard ILLUMINA sequencing primer sites used in paired-end sequencing. Sequencing a single cell 3' library produces a standard ILLUMINA BCL data output folder. The BCL data will include the paired-end Read 1 (containing the 16 bp 10×™ Barcode and 10 bp UMI) and Read 2 and the sample index in the i7 index read. In some embodiments, the Cell Ranger™ analysis pipelines perform secondary analysis and visualization. In addition to performing standard analysis steps such as demultiplexing, alignment, and gene counting, Cell Ranger™ leverages the Barcodes to generate expression data with single-cell resolution in the form of the discrete attribute value dataset 120. This data type enables applications including cell clustering, cell type classification, and differential gene expression at a scale of hundreds to millions of cells. Moreover, as discussed above, because the pipeline delivers this information by indexing discrete attribute value 124 from second entities on an individual second entity basis using barcodes, the data from such single cells can be combined with the data from other pipelines that make use of barcodes to track data from single cells, such as the V(D)J Pipeline described in section above entitled "V(D)J Pipeline" to provide unique biological insight into underlying molecular mechanisms associated with cell samples as disclosed above with reference to FIGS. 17 through 24.

While this section describes 3' chemistry and 3' protocol guide, in some embodiments, the discrete attribute value pipeline makes use of 5' chemistry and a 5' protocol when forming the nanoliter-scale Gel Bead-In-EMulsions (GEMs) and subsequent sequencing.

CONCLUSION

All references cited herein are incorporated herein by reference in their entirety and for all purposes to the same extent as if each individual publication or patent or patent application was specifically and individually indicated to be incorporated by reference in its entirety for all purposes.

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation(s).

It will also be understood that, although the terms first, second, etcetera may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting (the stated condition or event (" or "in response to detecting (the stated condition or event)," depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed:

1. A method of deconvolving a first clonal population comprising a first plurality of cells of a species, the method comprising:
   at a computer system having one or more processors, and memory storing one or more programs for execution by the one or more processors:
   (A) obtaining a set of nucleic acid sequence reads, in electronic form, from each cell in the first plurality of cells of the first clonal population through a single cell sequencing process, thereby obtaining a first plurality of sets of nucleic acid sequence reads, wherein each respective set of nucleic acid sequence reads in the first plurality of sets of nucleic acid sequence reads is from a corresponding single cell in the first plurality of cells;
   (B) mapping the sequence reads of each respective set of sequence reads onto a corresponding bin of a plurality of bins, wherein each respective bin of the plurality of bins represents a different portion of a reference genome of the species, thereby obtaining a nucleic acid sequence read count for each respective bin of the plurality of bins for each respective cell in the first plurality of cells, wherein the plurality of bins collectively encompass at least three percent of the reference genome;

(C) for each respective cell in the first plurality of cells, assigning the respective cell into one of a plurality of groups based upon a pattern of sequence read counts of the respective cell across the plurality of bins, wherein a first group in the plurality of groups represents a first mitotic stage, a second group in the plurality of groups represents a non-mitotic stage, and the assigning (C) determines whether the respective cell is to be assigned to the first group by applying a first mitotic filter to the nucleic acid read count of respective bins of the plurality of bins obtained for the respective cell, thereby deconvolving the first clonal population.

2. The method of claim 1, wherein the single cell sequencing process is a single cell DNA sequencing process and each nucleic acid sequence read in each set in the plurality of sets of nucleic acid sequence reads is a DNA sequence.

3. The method of claim 1, wherein the single cell sequencing process is a single cell RNA sequencing process and each nucleic acid sequence read in each set in the plurality of sets of nucleic acid sequence reads is an RNA sequence.

4. The method of claim 1, wherein the mapping (B) normalizes the nucleic acid sequence read counts for each respective bin of the plurality of bins for each respective cell in the first plurality of cells, the first mitotic filter is a first predetermined pattern of read counts across a first subset of the plurality of bins that has been previously associated with the first mitotic stage, and a respective cell in the first plurality of cells is assigned to the first group when the predetermined pattern of read counts across the first subset of the bins of the first mitotic filter is exhibited by the normalized nucleic acid sequence read counts for the respective cell across the first subset of the plurality of bins.

5. The method of claim 4, wherein a third group in the plurality of groups represents a second mitotic stage, the assigning (C) determines whether the respective cell is to be assigned to the third group by applying a second mitotic filter to the nucleic acid read count of respective bins of the plurality of bins obtained for the respective cell, the second mitotic filter is a second predetermined pattern of read counts across a second subset of the plurality of bins that has been previously associated with the second mitotic stage, and a respective cell in the first plurality of cells is assigned to the second group when the predetermined pattern of read counts across the subset of the bins of the second mitotic filter is exhibited by the normalized nucleic acid sequence read counts for the respective cell across the second subset of the plurality of bins.

6. The method of claim 1, wherein the species is human, each bin of the plurality of bins is the same size, and the plurality of bins consists of between one hundred and two thousand bins.

7. The method of claim 1, the method further comprising exposing the first plurality of cells to a perturbation prior to the obtaining step (A).

8. The method of claim 7, wherein the first plurality of cells are exposed to the perturbation for at least one hour prior to performing the obtaining step (A).

9. The method of claim 7, wherein the perturbation is a compound.

10. The method of claim 9, wherein the compound is an organic compound having a molecular weight of less than 2000 Daltons.

11. The method of claim 9, wherein the compound is an organic compound that satisfies the Lipinski rule of five criteria.

12. The method of claim 9, wherein the compound is an organic compound that satisfies at least three criteria of the Lipinski rule of five criteria.

13. The method of claim 9, wherein the compound is a checkpoint blockade immunotherapy.

14. The method of claim 13, wherein the checkpoint blockade immunotherapy is an anti-CTLA-4, anti-PD1, anti-PD-L1, anti-LAG3, anti-TIM-3, anti-GITR, anti-0X40, anti-CD40, anti-TIGIT, anti4-1BB, anti-B7-H3, anti-B7-H4, or anti-BTLA compound.

15. The method of claim 7, the method further comprising:

(D) obtaining a set of nucleic acid sequence reads, in electronic form, from each cell in a second clonal population comprising a second plurality of cells of the species through a single cell sequencing process, thereby obtaining a second plurality of sets of nucleic acid sequence reads, wherein each respective set of nucleic acid sequence reads in the second plurality of sets of nucleic acid sequence reads is from a single cell in the second plurality of cells;

(E) mapping the sequence reads of each respective set of sequence reads of the second plurality of sets of nucleic acid sequence reads onto a corresponding bin of the plurality of bins;

(F) for each respective cell in the second plurality of cells, assigning the respective cell into one of the plurality of groups based upon a pattern of sequence read counts of the respective cell across the plurality of bins, wherein the assigning (F) determines whether the respective cell is to be assigned to the first group by applying the first mitotic filter to the nucleic acid read count of respective bins of the plurality of bins obtained for the respective cell; and (G) comparing a relative assignment of cells in (i) the first plurality of cells and (ii) the second plurality of cells to individual groups in the first plurality of groups.

16. The method of claim 1, wherein the first plurality of cells is from a tumor biopsy.

17. The method of claim 1, wherein the first plurality of cells is heterogeneous.

18. The method of claim 1, wherein the species is human.

19. The method of claim 18 wherein each bin in the plurality of bins is the same or different size.

20. A computer system having one or more processors, and memory storing one or more programs for execution by the one or more processors, the one or more programs comprising instructions for performing a method of deconvolving a first clonal population comprising a first plurality of cells of a species comprising:

(A) obtaining a set of nucleic acid sequence reads, in electronic form, from each cell in the first plurality of cells of the first clonal population through a single cell sequencing process, thereby obtaining a first plurality of sets of nucleic acid sequence reads, wherein each respective set of nucleic acid sequence reads in the first plurality of sets of nucleic acid sequence reads is from a corresponding single cell in the first plurality of cells;

(B) mapping the sequence reads of each respective set of sequence reads onto a corresponding bin of a plurality of bins, wherein each respective bin of the plurality of bins represents a different portion of a reference genome of the species, thereby obtaining a nucleic acid sequence read count for each respective bin of the plurality of bins for each respective cell in the first plurality of cells, wherein the plurality of bins collectively encompass at least three percent of the reference genome;

(C) for each respective cell in the first plurality of cells, assigning the respective cell into one of a plurality of groups based upon a pattern of sequence read counts of the respective cell across the plurality of bins, wherein a first group in the plurality of groups represents a first mitotic stage, a second group in the plurality of groups represents a non-mitotic stage, and the assigning (C) determines whether the respective cell is to be assigned to the first group by applying a first mitotic filter to the nucleic acid read count of respective bins of the plurality of bins obtained for the respective cell, thereby deconvolving the first clonal population.

21. The computer system of claim 20, wherein the mapping (B) normalizes the nucleic acid sequence read counts for each respective bin of the plurality of bins for each respective cell of the first plurality of cells, the first mitotic filter is a first predetermined pattern of read counts across a first subset of the plurality of bins that has been previously associated with the first mitotic stage, and a respective cell in the first plurality of cells is assigned to the first group when the predetermined pattern of read counts across the first subset of the bins of the first mitotic filter is exhibited by the normalized nucleic acid sequence read counts for the respective cell across the first subset of the plurality of bins.

22. A non-transitory computer readable storage medium, wherein the non-transitory computer readable storage medium stores instructions, which when executed by a computer system, cause the computer system to perform a method of deconvolving a first clonal population comprising a first plurality of cells of a species comprising:

(A) obtaining a set of nucleic acid sequence reads, in electronic form, from each cell in the first plurality of cells of the first clonal population through a single cell sequencing process, thereby obtaining a first plurality of sets of nucleic acid sequence reads, wherein each respective set of nucleic acid sequence reads in the first plurality of sets of nucleic acid sequence reads is from a single cell in the first plurality of cells and represents at least four percent of the genome of the corresponding cell;

(B) mapping the sequence reads of each respective set of sequence reads onto a corresponding bin of a plurality of bins, wherein each respective bin of the plurality of bins represents a different portion of a reference genome of the species, thereby obtaining a nucleic acid sequence read count for each respective bin of the plurality of bins for each respective cell in the first plurality of cells, wherein the plurality of bins collectively encompass at least three percent of the reference genome;

(C) for each respective cell in the first plurality of cells, assigning the respective cell into one of a plurality of groups based upon a pattern of sequence read counts of the respective cell across the plurality of bins, wherein a first group in the plurality of groups represents a first mitotic stage, a second group in the plurality of groups represents a non-mitotic stage, and the assigning (C) determines whether the respective cell is to be assigned to the first group by applying a first mitotic filter to the nucleic acid read count of respective bins of the plurality of bins obtained for the respective cell, thereby deconvolving the first clonal population.

\* \* \* \* \*